(12) United States Patent
Kahook et al.

(10) Patent No.: US 11,931,293 B2
(45) Date of Patent: Mar. 19, 2024

(54) APPARATUS AND METHOD FOR CATARACT EXTRACTION

(71) Applicant: NEW WORLD MEDICAL, INC., Rancho Cucamonga, CA (US)

(72) Inventors: Malik Y. Kahook, Denver, CO (US); Suhail Abdullah, Fontana, CA (US); Khalid Mansour, Corona, CA (US); Eric Porteous, Corona, CA (US); Joey Tran, Ontario, CA (US); Patrick Chen, Hacienda Heights, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 1096 days.

(21) Appl. No.: 15/999,465

(22) PCT Filed: Feb. 17, 2017

(86) PCT No.: PCT/US2017/018490
§ 371 (c)(1),
(2) Date: Jan. 8, 2020

(87) PCT Pub. No.: WO2017/143272
PCT Pub. Date: Aug. 24, 2017

(65) Prior Publication Data
US 2021/0121326 A1    Apr. 29, 2021

Related U.S. Application Data

(60) Provisional application No. 62/363,149, filed on Jul. 15, 2016, provisional application No. 62/297,725, filed on Feb. 19, 2016.

(51) Int. Cl.
*A61F 9/007*    (2006.01)

(52) U.S. Cl.
CPC .................. *A61F 9/00736* (2013.01)

(58) Field of Classification Search
CPC ........... A61F 9/00736; A61B 17/22031; A61B 2017/2217; A61B 2017/306;
(Continued)

(56) References Cited

U.S. PATENT DOCUMENTS 5,891,153 A     4/1999  Peterson
2007/0016225 A1*  1/2007  Nakao .................. A61B 17/221
                                                                 606/114

(Continued)

OTHER PUBLICATIONS

International Search Report and Written Opinion for Application No. PCT/US2017/018490, dated Oct. 13, 2017, 19 pages.
(Continued)

*Primary Examiner* — Ashley L Fishback
*Assistant Examiner* — Chima U Igboko
(74) *Attorney, Agent, or Firm* — Morgan, Lewis & Bockius LLP

(57) ABSTRACT

An extraction device can include a delivery shaft having a lumen and a distal end, a first wire forming a first arc and being positionable distal to the distal end of the delivery shaft while ends of the first arc are at a distalmost end of the delivery shaft, and a second wire forming a second arc and being positionable distal to the distal end of the delivery shaft while ends of the second arc are at the distalmost end of the delivery shaft. A distalmost extent of the first wire is distal to a distalmost extent of the second wire. The first wire and the second wire are separately retractable relative to the delivery shaft.

9 Claims, 35 Drawing Sheets

(58) Field of Classification Search
CPC .......... A61B 2017/32004; A61B 2017/32006; A61B 17/320016; A61B 17/32053; A61B 17/32056; A61B 17/221
See application file for complete search history.

(56) References Cited

U.S. PATENT DOCUMENTS

2013/0211415 A1     8/2013   Zerfas et al.
2014/0364868 A1*   12/2014   Dhindsa ............... A61B 17/221
                                                        606/127

OTHER PUBLICATIONS

European Office Action for Application No. 17708938.0, dated Feb. 11, 2022, 7 pages.

* cited by examiner

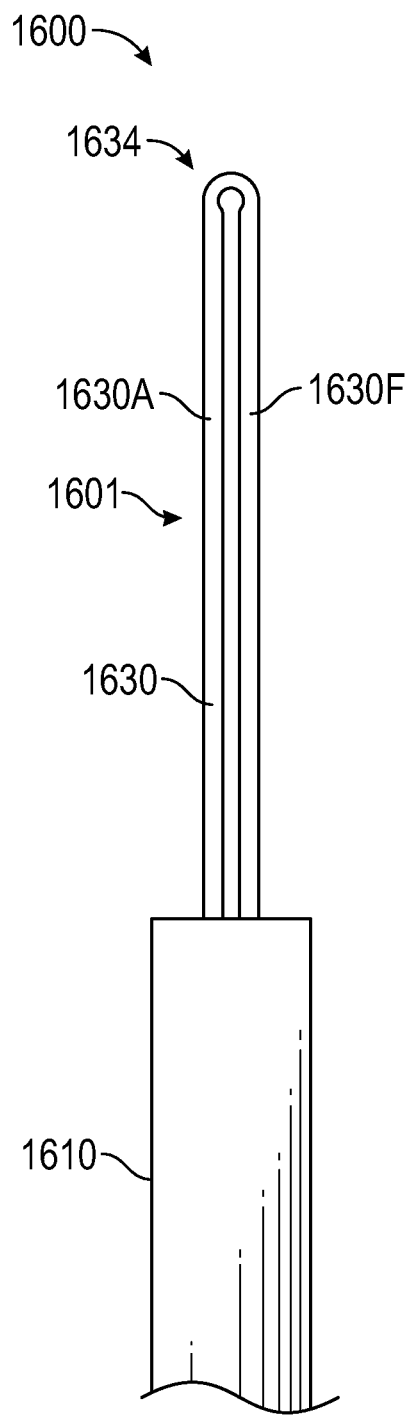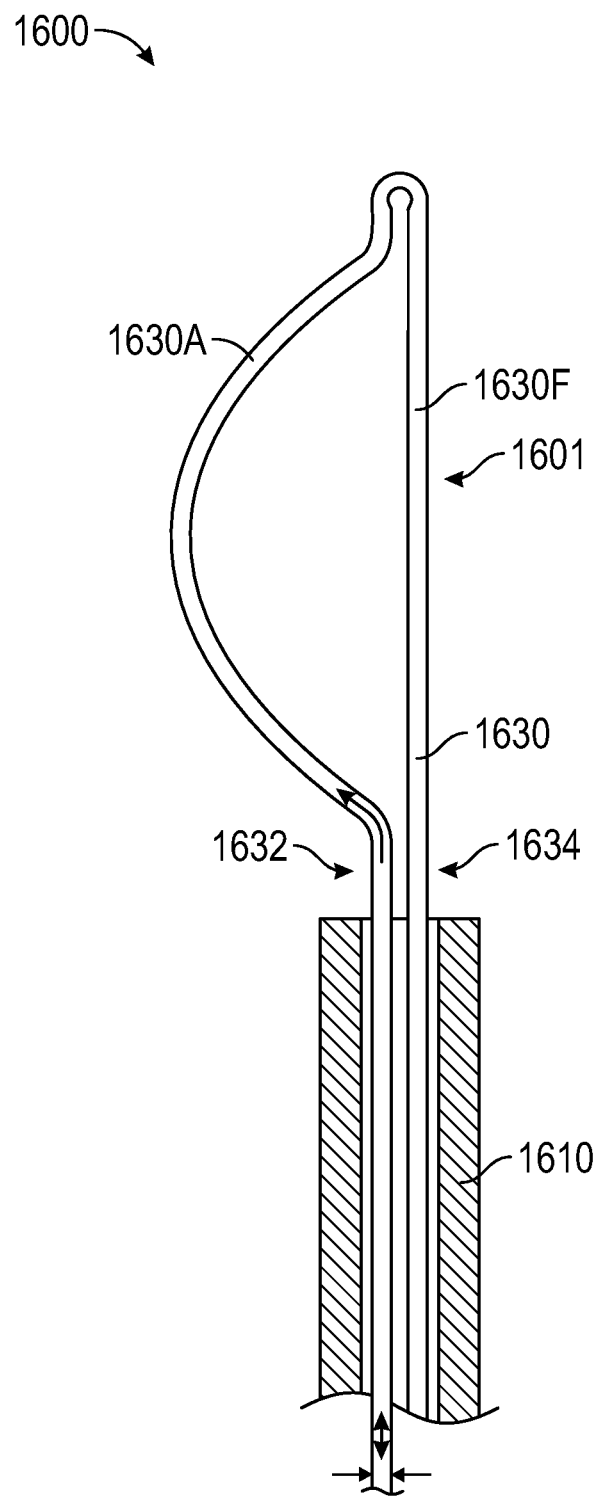
FIG. 16A  FIG. 16B

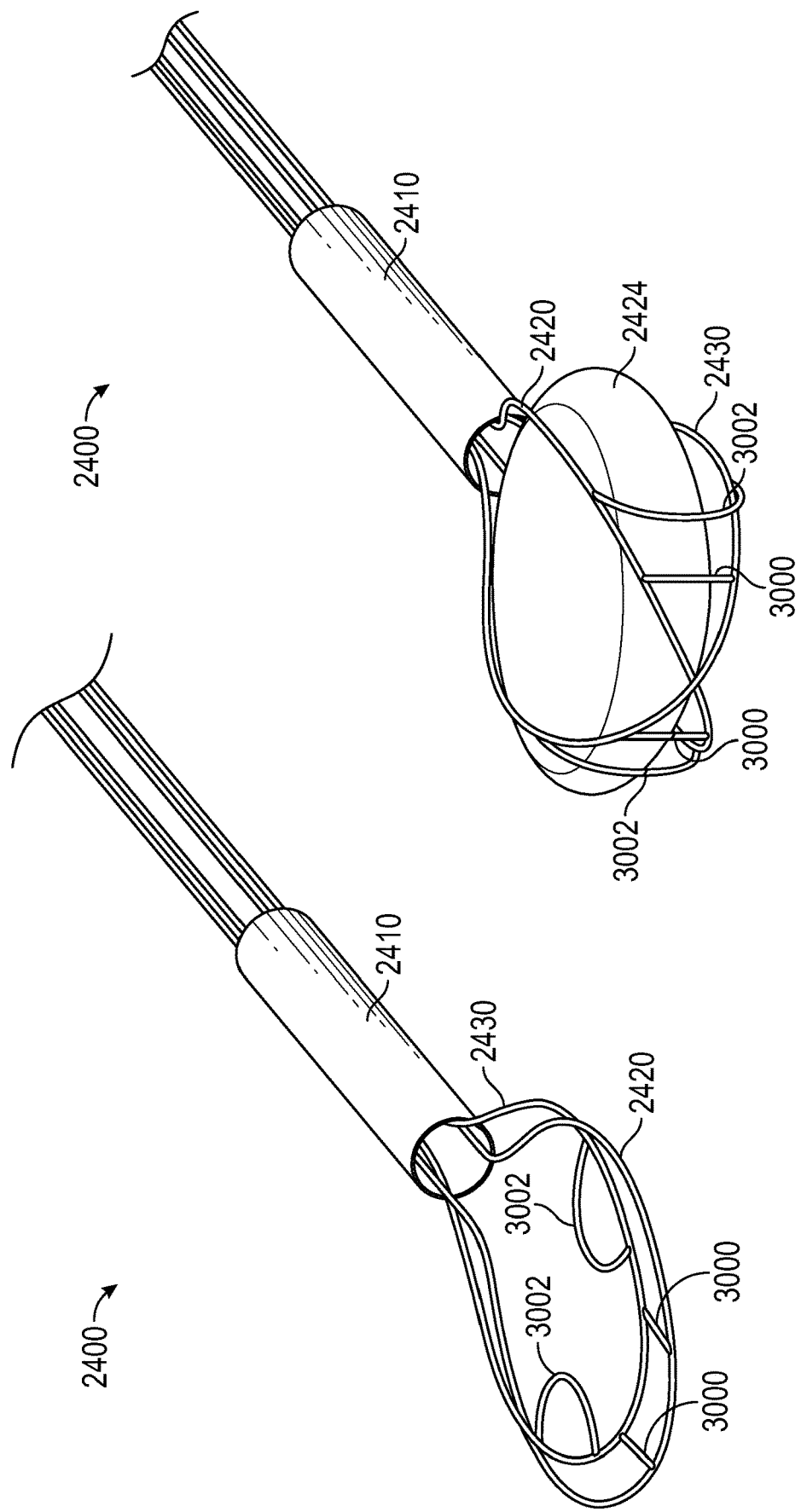

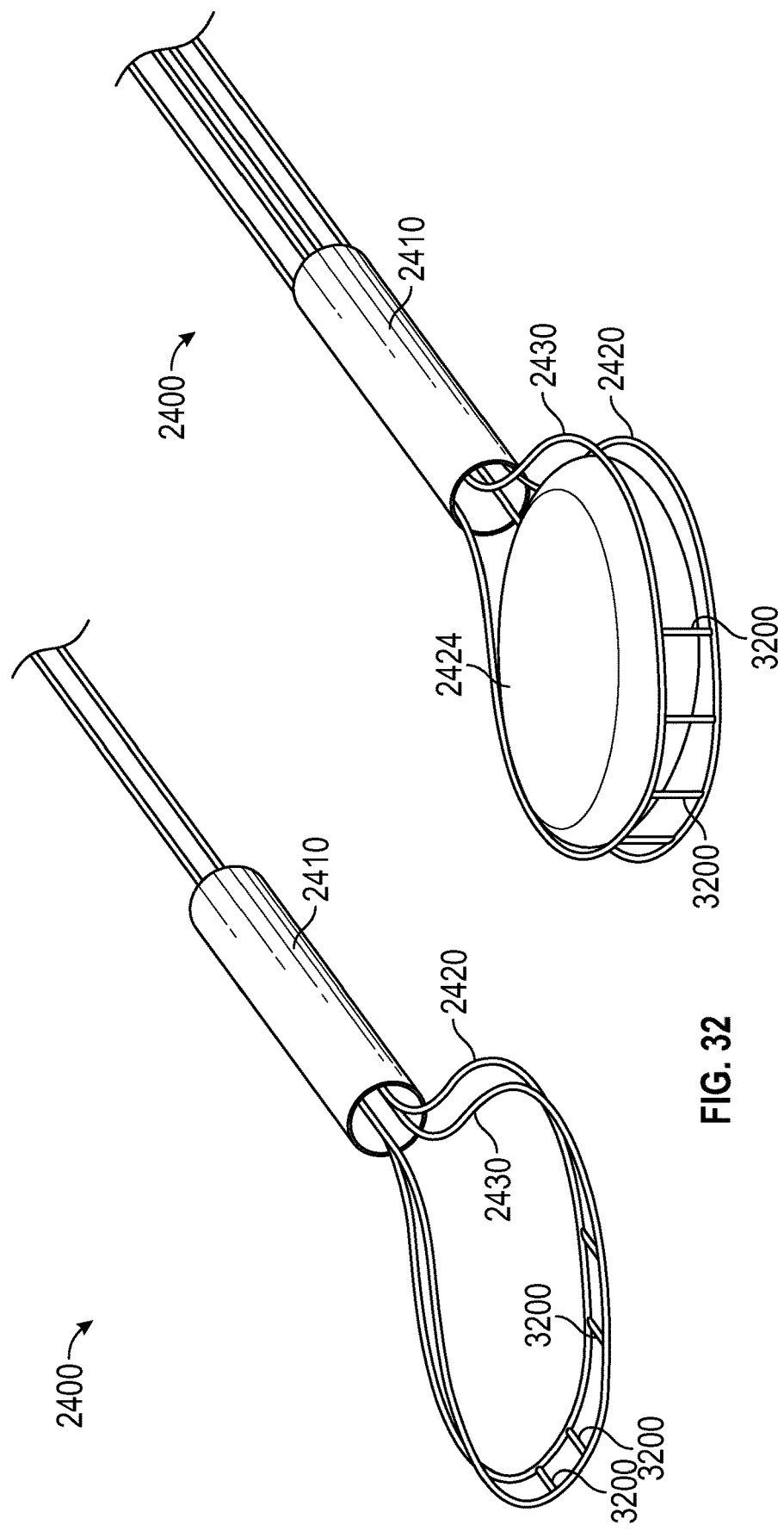

APPARATUS AND METHOD FOR CATARACT EXTRACTION

CROSS-REFERENCE TO RELATED APPLICATIONS

The present application claims the benefit of priority under 35 U.S.C. § 119 to U.S. Provisional Patent Application Ser. No. 62/363,149 entitled "APPARATUS AND METHOD FOR CATARACT EXTRACTION" filed on Jul. 15, 2016, and U.S. Provisional Patent Application Ser. No. 62/297,725 entitled "APPARATUS AND METHOD FOR CATARACT EXTRACTION" filed on Feb. 19, 2016, the disclosure of each of which is hereby incorporated by reference in its entirety for all purposes.

TECHNICAL FIELD

The present disclosure generally relates to surgical devices and, in particular, relates to cataract extraction devices.

BACKGROUND

Cataracts often cause loss of vision by clouding the lens of the eye. Cataract surgery is often performed, in which the lens is removed from the eye and replaced with a synthetic lens. However, if care is not taken, it can be difficult to remove the lens without creating a large incision or without breaking the lens into an uncontrollable number of small pieces.

SUMMARY

A handheld device, sometimes referred to herein as a cataract extraction device or an extraction device, is provided that can be used to break the lens of the eye of a patient into a desired number of pieces and remove the resulting pieces from the eye through an incision. For example, after a hydrodissection of the lens has been performed to displace the lens from its capsule, the extraction device can be moved into the eye through a corneal incision and be utilized to encapsulate or partially surround the lens and remove it in a controlled manner in one or more pieces. A second device can be used to flush the eye of any lens remnants.

The extraction device may include additional mechanisms or components to control the motion of lens elements out of the anterior chamber of the eye. The devices can be provided together as a kit. In some embodiments, the extraction device can contain at least a part of the lens during and/or after hydrodissection. If the lens is undesirably displaced during hydrodissection, the device can be used to recapture the lens or a portion thereof.

In accordance with certain aspects, an extraction device is provided that includes a delivery shaft having a lumen and a distal end. The extraction device also includes a first wire forming a first arc and being positionable distal to the distal end of the delivery shaft while ends of the first arc are at a distalmost end of the delivery shaft. The extraction device also includes a second wire forming a second arc and being positionable distal to the distal end of the delivery shaft while ends of the second arc are at the distalmost end of the delivery shaft. A distalmost extent of the first wire is distal to a distalmost extent of the second wire, and the first wire and the second wire are separately retractable relative to the delivery shaft.

In accordance with other aspects, an extraction device is provided that includes a delivery shaft having a lumen and a distal end. The extraction device also includes a dissection tool distal to the distal end of the delivery shaft. The extraction device also includes a first capture portion positionable on a first side of an axis of the delivery shaft and comprising a first cover. The extraction device also includes a second capture portion positionable on a second side of the axis, opposite the first side, and comprising a second cover. The first capture portion and the second capture portion are configured to move toward the axis upon actuation and define an enclosed space between the first cover and the second cover.

In accordance with other aspects, an extraction device is provided that includes a delivery shaft having a distal end. The extraction device also includes an irrigation port at the distal end. The extraction device also includes a loop having a fluid permeable cover. The extraction device also includes a blade being moveable from a retracted position to an actuated position across at least a portion of the loop.

In accordance with other aspects, an extraction device is provided that includes a delivery shaft having an inner cylindrical shaft structure with a distal end. The delivery shaft also includes an outer cylindrical shaft structure having a distal end with a sharp cutting edge. The sharp cutting edge of the outer cylindrical shaft structure is deployable beyond the distal end of the inner cylindrical shaft structure.

In accordance with other aspects, an extraction device is provided that includes a delivery shaft having a distal end with a sharp cutting edge. The extraction device also includes a gripping apparatus that is extendible from within a lumen of the delivery shaft and operable to grip and pull tissue against the sharp cutting edge.

In accordance with other aspects, an extraction device is provided that includes a delivery shaft having a distal end. The extraction device also includes an excision member that is extendible from within a lumen of the delivery shaft. The excision member includes a control shaft and a plurality of layered cutting and encapsulation leaves.

In accordance with other aspects, an extraction device is provided that includes a delivery shaft having a distal end. The extraction device also includes a first frame extendible from the distal end of the delivery shaft and having a flexible bag structure attached thereto. The extraction device also includes a second frame extendible from the distal end of the delivery shaft and having a lid structure attached thereto. In an extended configuration for the first frame and the second frame, the flexible bag structure and the lid structure are configured to define and enclose a cavity within which at least a portion of a lens of a patient's eye is encapsulated.

In accordance with other aspects, a method is provided that includes extending a first frame, having an attached flexible bag structure, and a second frame into an eye of a patient such that the flexible bag structure at least partially surrounds at least a portion of a lens of the eye of the patient. The method also includes extending a third frame having an attached lid structure along the first frame to encapsulate the at least the portion of the lens between the flexible bag structure and the lid structure. The method also includes withdrawing the second frame to transect the encapsulated at least the portion of the lens.

In accordance with other aspects, an extraction device is provided that includes a delivery shaft having a distal end. The extraction device also includes a first frame extendible from the distal end of the delivery shaft and having a flexible bag structure attached thereto. The flexible bag structure includes a plurality of openings. The extraction device also includes a second frame extendible from the distal end of the delivery shaft and having a lid structure attached thereto. In an extended configuration for the first frame and the second frame, the flexible bag structure and the lid structure are configured to secure at least a portion of a lens of a patient's eye therebetween.

In accordance with other aspects, a method is provided that includes extending a first frame having an attached flexible bag structure with a plurality of openings from a distal end of a delivery shaft into an anterior chamber of an eye of a patient such that the flexible bag structure at least partially surrounds at least a portion of a lens of the eye of the patient. The method also includes extending a second frame having an attached lid structure along the first frame to secure the at least the portion of the lens between the flexible bag structure and the lid structure. The method also includes withdrawing the first and second frames into the distal end of the delivery shaft to strain the at least the portion of the lens through the plurality of openings in the flexible bag structure into the anterior chamber.

In accordance with other aspects, an extraction device is provided that includes a delivery shaft having a lumen and a distal end. The extraction device also includes first, second, and third wire loops extendible from within the lumen at the distal end, wherein the first, second, and third wire loops are configured to separate upon extension from within the lumen to at least partially surround a lens of a patient's eye, and wherein the separated first, second, and third wire loops are configured to be withdrawn into the lumen to pass through and dissect the lens.

In accordance with other aspects, an extraction device is provided that includes a delivery shaft having a lumen and a distal end. The extraction device also includes first and second wire loops extendible from within the lumen at the distal end. The extraction device also includes a plurality of interconnecting wires that extend from the first wire loop to the second wire loop. The first and second wire loops are configured to separate upon extension from within the lumen to at least partially surround a lens of a patient's eye, and the separated first and second wire loops and the plurality of interconnecting wires are configured to be withdrawn into the lumen to pass through and dissect the lens.

In accordance with other aspects, an extraction device is provided that includes a delivery shaft having a lumen and a distal end. The extraction device also includes first, second, and third wire loops extendible from within the lumen at the distal end, wherein the first, second, and third wire loops are configured to separate upon extension from within the lumen and are maneuverable to at least partially surround a lens of a patient's eye. The extraction device also includes a stent extendible from within the lumen around the extended first, second, and third wire loops. The extraction device also includes an encapsulation bag extendible from within the lumen around the extended stent and the extended first, second, and third wire loops.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 16A shows a side view of an extraction device, in accordance with one or more embodiments of the present disclosure.

FIG. 16B shows a cross-sectional side view the extraction device of FIG. 16A, in accordance with one or more embodiments of the present disclosure.

FIG. 30 shows a perspective view of a portion of an extraction device having two interconnected wire loops in a flattened configuration, in accordance with one or more embodiments of the present disclosure.

FIG. 31 shows a perspective view of the portion of the extraction device of FIG. 30 with the interconnected wire loops in a rotated configuration, in accordance with one or more embodiments of the present disclosure.

FIG. 32 shows a perspective view of a portion of another extraction device having two interconnected wire loops in a flattened configuration, in accordance with one or more embodiments of the present disclosure.

FIG. 33 shows a perspective view of the portion of the extraction device of FIG. 32 with the interconnected wire loops in a separated configuration, in accordance with one or more embodiments of the present disclosure.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with various embodiments described in further detail below, an extraction device may be provided with a delivery shaft and one or more components or features that can be extended from a lumen of the delivery shaft to cut, grab, encapsulate, and/or otherwise manipulate the lens of a patient's eye for extraction.

Figure 1A:
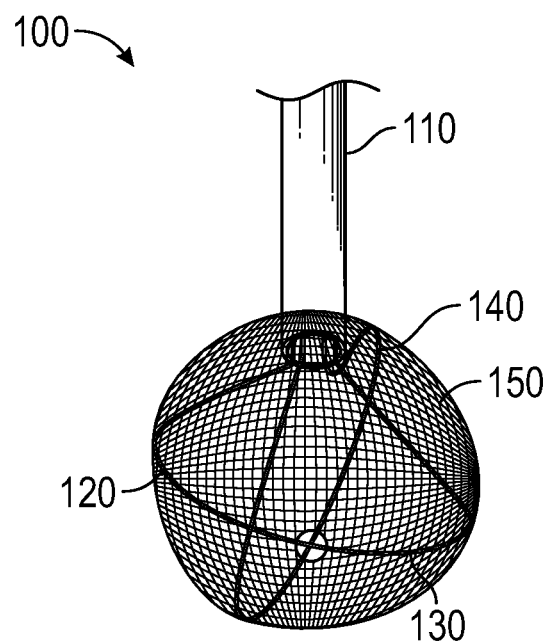
FIG. 1A shows a perspective view of an extraction device, in accordance with one or more embodiments of the present disclosure.

According to some embodiments, for example as shown in FIG. 1A, an extraction device 100 can include a delivery shaft 110 having a lumen and a distal end. A cover 150 can encompass an outer cross-sectional dimension of a capture region 120 defined, at least in part, by each of (i) the first wire 130 and (ii) the second wire 140, as described further herein. The wires can be textured and/or contain features that allow a lens to be grasped, to help break up the lens, and to grip the lens while it is being moved.

Figure 1B:
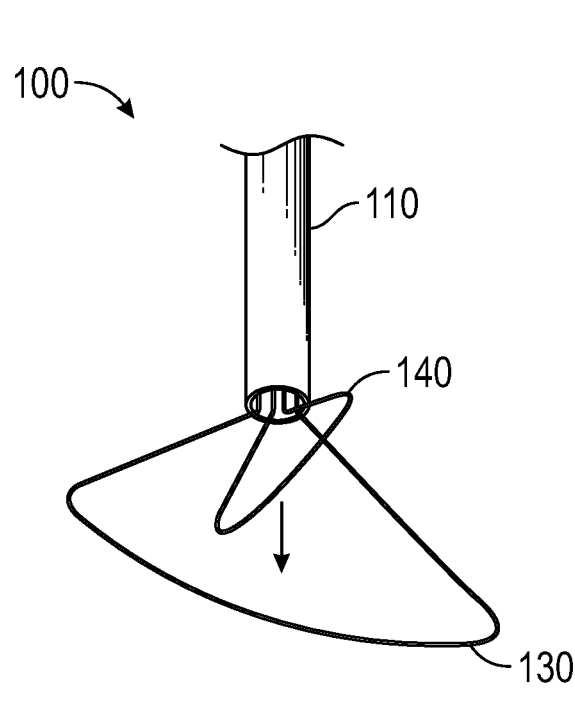
FIG. 1B shows a perspective view of the extraction device of FIG. 1A, in accordance with one or more embodiments of the present disclosure.
Figure 1C:
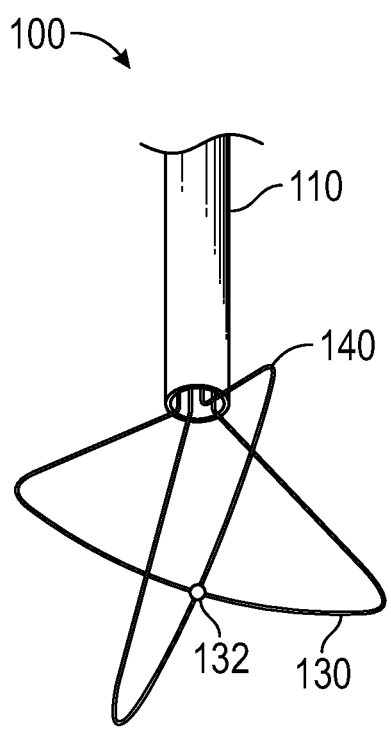
FIG. 1C shows a perspective view of the extraction device of FIG. 1A, in accordance with one or more embodiments of the present disclosure.

The first wire 130 can form a first arc portion (e.g., loop) distal to the distal end of the delivery shaft 110, and the second wire 140 can form a second arc portion (e.g., loop) distal to the distal end of the delivery shaft 110. Each of the first wire 130 and the second wire 140 can be separately retractable relative to the delivery shaft 110. As shown in FIGS. 1B and 1C, the first wire 130 can be deployed from the lumen of the delivery shaft 110 before the second wire 140 is deployed. The second wire 140 can be deployed until it reaches a distalmost end 132 of the first wire 130. The distalmost end of the second wire 140 can remain proximal to the distalmost end 132 of the first wire 130. Additionally, the second wire 140 can be retracted into the lumen of the delivery shaft 110 before the first wire 130 is retracted. According to some embodiments, the separate wires can be connected to each other and can be advanced and/or retracted at the same time. According to some embodiments, the wires can also rotate in the same direction and/or in multiple directions prior to and/or during advancement and/or retraction. According to some embodiments, one or more wires can be contained within another wire. For instance, a larger diameter wire can have a groove for receiving a smaller wire. A third wire is connected to a cover, such as a net or bag. Once the lens is encapsulated in the cover, the smaller second wire is actuated and moves along the groove of the first wire to dissect the lens.

The first wire 130 and the second wire 140 can be rings of metal (e.g., nitinol), plastic, and/or a shape memory material. The capture region 120 may also include other materials, such as a suture or polymer that acts to encircle the lens once deployed from the lumen. The rings can be closed by retraction to cut a lens of a patient into smaller pieces. Alternatively, or in combination, other mechanisms could be employed to dissect the lens, including scissors, forceps, or blades. Such tools can dissect the lens as the lens is held in position or move (e.g., rotate) the lens against a mechanism to cut the lens. Alternatively, or in combination, any number of wires can be provided. For example, wires in addition to the first wire 130 and the second wire 140 can be provided in a nested formation, such that each wire is deployed within a region bounded by an adjacent wire.

Figure 1D:
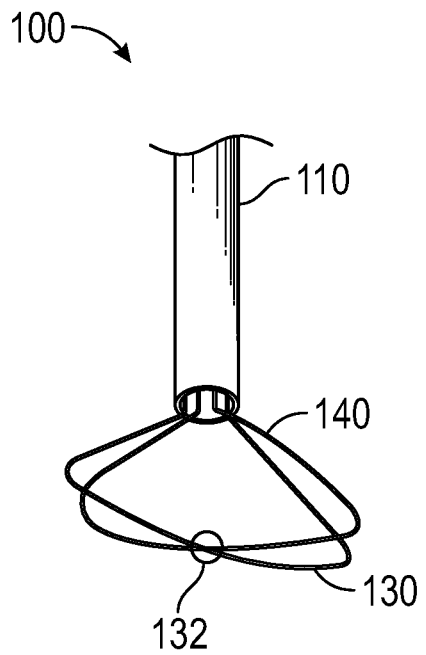
FIG. 1D shows a perspective view of the extraction device of FIG. 1A, in accordance with one or more embodiments of the present disclosure.
Figure 1E:
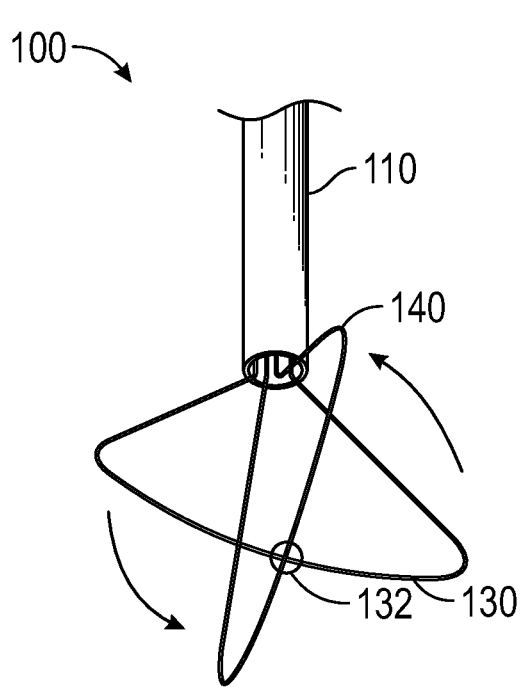
FIG. 1E shows a perspective view of the extraction device of FIG. 1A, in accordance with one or more embodiments of the present disclosure.

According to some embodiments, for example as shown in FIGS. 1D and 1E, the first wire 130 and the second wire 140 can be rotated relative to each other before, during, or after deployment from the delivery shaft 110. As shown in FIG. 1D, the first wire 130 and the second wire 140 can be positioned to be substantially flat. As shown in FIG. 1E, the first wire 130 and the second wire 140 can be positioned to have an enlarged region of enclosure within the first wire 130 and the second wire 140. For example, the first wire 130 can reside within a plane that is substantially perpendicular to a plane within which the second wire 140 resides.

Figure 1F:
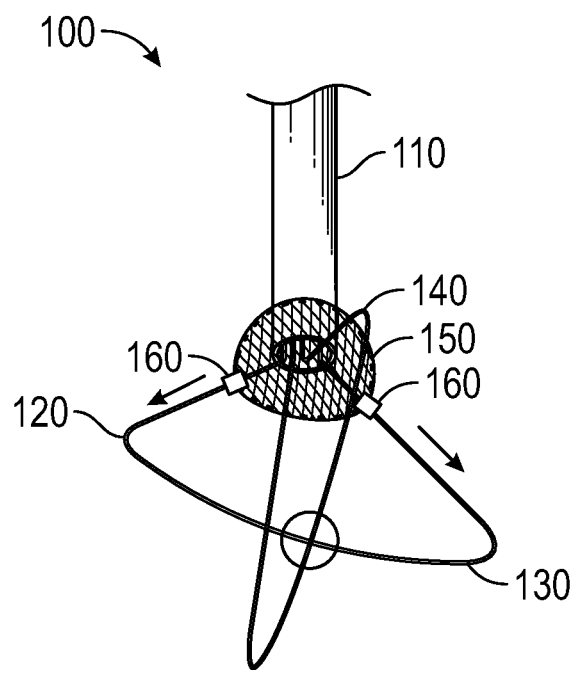
FIG. 1F shows a perspective view of the extraction device of FIG. 1A, in accordance with one or more embodiments of the present disclosure.
Figure 1G:
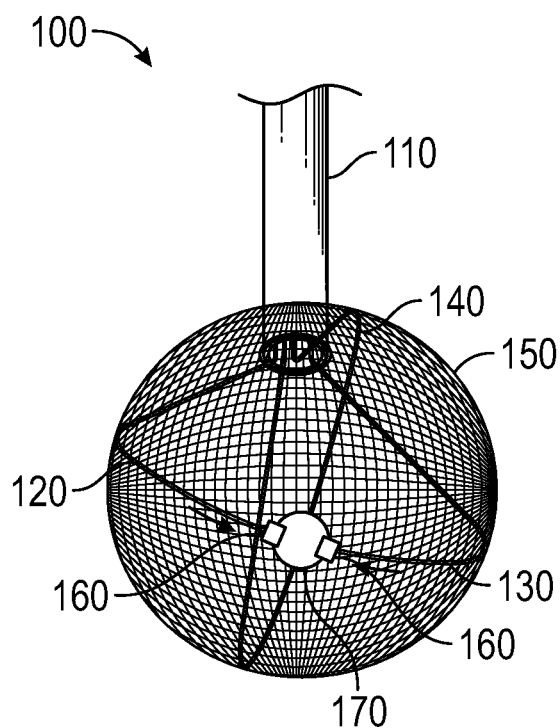
FIG. 1G shows a perspective view of the extraction device of FIG. 1A, in accordance with one or more embodiments of the present disclosure.

According to some embodiments, for example as shown in FIGS. 1F and 1G, the cover 150 can be moved about the capture region 120. One or more guides 160 can be moveable along the arc portion of the first wire 130 toward the distalmost end 132 of the first wire 130. The guides 160 can deploy the cover 150 about the capture region 120 as they move along the first wire 130 from a first position (see FIG. 1F) to a second position (see FIG. 1G), more distal than the first position. While in the second position, the cover 150 encompasses an outer cross-sectional dimension of each of (i) the first wire 130 and (ii) the second wire 140. The cover can extend such that an aperture 170 remains at the distalmost end 132 of the first wire 130. The guides 160 can partially or completely wrap around a wire 130, 140 and/or be able to travel along or within a groove of a wire 130, 140. The guides 160 can be actuated (e.g., advanced and/or retracted) by one or more push rods (not shown) that connect to the guides 160 and have a portion thereof that is accessible to the user. The push rods can extend through the delivery shaft 110. The push rods can be actuated based on mechanical activation (e.g., trigger or rack and pinion control) and/or electrical activation (e.g., motor).

The cover 150 can include polyethylene or similar compliant polymer. The cover 150 can include polyethylene and nitinol, PTFE and nitinol, a flexible polymer and/or nitinol, a substantially inflexible material and/or nitinol, a substantially inflexible material and/or a material that acts as a platform for the inflexible or flexible material membranes so that the membrane may be advanced efficiently over the capture region 120. Additional structures that can accompany a cover are discussed in greater detail herein. The cover 150 can be a molded piece of elastomeric material that is everted. The cover 150 can have a natural tendency to return to its original shape. A device that is controllable by a user can be brought into contact with the cover 150 to urge the cover 150 into a shape for which the cover 150 has a bias.

According to some embodiments, the capture region 120 can be introduced prior to the cover 150 and the cover 150 is deployed second over the capture region 120 which has already been positioned to hold the natural lens. According to some embodiments, the cover 150 can be introduced prior to the capture region 120 and the capture region 120 is deployed second over the cover 150 which has already been positioned to hold the natural lens. The cover 150 can be deployed to capture a lens before, during, or after the lens has been cut and/or dissected (e.g., hydrodissected from the lens capsule and/or divided into pieces) by a tool (e.g., the wires 130, 140 of the capture region 120). The cover 150 can be deployed from a proximal end of the capture region 120 and a distal direction or from a distal end of the capture region 120 in a proximal direction.

The capture region 120 and/or the cover 150 can be retracted in stages or in one movement into the lumen of the introducer. According to some embodiments, the material that forms the lumen used to introduce the capture region 120 and cover 150 is composed of flexible material that may expand when the capture region 120 and cover 150 are retracted and then returns to previous form.

According to some embodiments, the capture region 120 and cover 150 are maneuvered in and out of the eye with a screw type mechanism to control linear motion. According to some embodiments, the capture region 120 and cover 150 are maneuvered in and out of the eye with a hydraulic system to control linear motion. According to some embodiments, the capture region 120 and cover 150 are maneuvered in and out of the eye with a mechanical mechanism to control linear motion, such as a pneumatic control.

According to some embodiments, the capture region 120 and cover 150 are maneuvered in and out of the eye after the lens has been completely removed from the natural bag and positioned at the iris plane or above.

According to some embodiments, the capture region 120 and cover 150 are maneuvered to feed the lens into a cutting membrane that is present at the lumen of the device so as to cause further segmentation of the lens prior to retracting into the lumen. According to some embodiments, the capture region 120 and cover 150 are maneuvered to feed the lens using a twisting action so as to cause further segmentation of the lens prior to retracting into the lumen. According to some embodiments, a third structure is introduced that contains a second lumen that "punches a hole" within the body of the contained lens material so as to core out the central nucleus prior to being retracted into the lumen of the main device. According to some embodiments, the device lumen is connected to an inflow and outflow lumen that allows for fluid to enter and exit the eye and to maintain the anterior chamber. According to some embodiments, the device lumen is connected to an inflow and outflow lumen that allows for lens material to enter and exit the eye and to maintain the anterior chamber.

According to some embodiments, the cover 150 surrounds the lens which has been dissected out of the lens bag and a cover 150 that contains a second lumen "punches a hole" within the body of the contained lens material so as to core out the central nucleus prior to being retracted into the lumen of the main device (no capture region 120 is used).

According to some embodiments, the extraction device is devoid of electronic components. According to some embodiments, the extraction device is operated using finger and hand controls. According to some embodiments, the extraction device is operated with foot pedal controls.

According to some embodiments, the capture region 120 is used independently to segment the lens into smaller pieces and a second device, commonly known as phacoemulsification hand piece or irrigation/aspiration hand piece, is used to remove the segmented lens pieces.

According to some embodiments, the capture region 120 and/or the cover 150 are manufactured from materials that are substantially transparent to optical coherence tomography imaging so as to not interfere or substantially not interfere with intraoperative OCT imaging. According to some embodiments, the structures of the extraction device are colored so the operator may easily differentiate between the parts.

According to some embodiments, the entire extraction device is disposable. According to some embodiments, some parts of the extraction device are disposable. For example, the capture region 120 and the cover 150 are designed so that removing them for cleaning will disallow further adjoining with the lumen shaft.

According to some embodiments, the extraction device, including capture region 120 and/or secondary component are designed to contain a plurality of holes that are 50 microns to 1 mm in size. The holes are designed to allow for segmentation of the lens into pieces equal to or smaller than 1 mm once the distal components are retracted back into the lumen. The segmented pieces, which remain in the anterior chamber, are then removed from the eye by an irrigation/aspiration extraction device.

According to some embodiments, the capture region 120 is discontinuous, with only partial surrounding of the lens prior to manipulation of the lens.

Figure 2A:
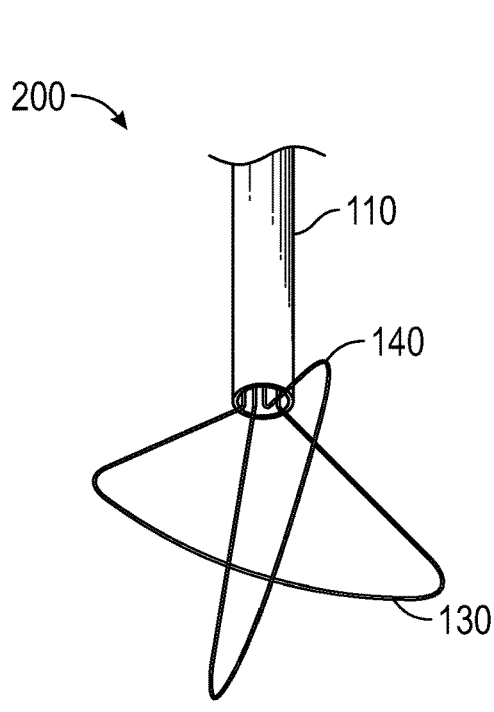
FIG. 2A shows a perspective view of an extraction device, in accordance with one or more embodiments of the present disclosure.
Figure 2B:
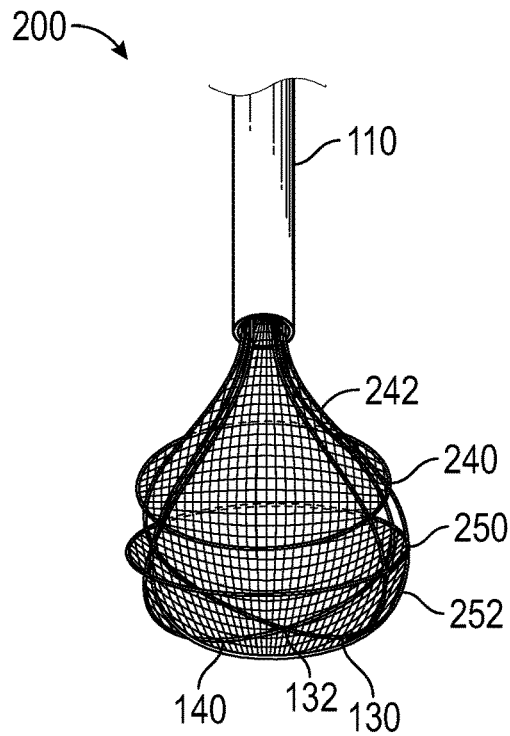
FIG. 2B shows a perspective view of the extraction device of FIG. 2A, in accordance with one or more embodiments of the present disclosure.

According to some embodiments, for example as shown in FIGS. 2A and 2B, an extraction device 200 can include a first ring 240 extending about the first wire 130 and the second wire 140 and a first cover 242 extending from the first ring 240 to the delivery shaft 110. The extraction device 200 can also include a second ring 250 extending about the first wire 130 and the second wire 140 and a second cover 252 extending from the second ring 250 to the distalmost end 132 of the first wire 130. The first cover 242 and the second cover 252 can enclose a space for capturing debris. The first ring 240 and the second ring 250 can be adjacent to each other or spaced apart. The first ring 240 and the second ring 250 can be actuated (e.g., advanced and/or retracted) by one or more push rods (not shown) that connect to the first ring 240 and the second ring 250 and have a portion thereof that is accessible to the user. The push rods can extend through the delivery shaft 110. The push rods can be actuated based on mechanical activation (e.g., trigger or rack and pinion control) and/or electrical activation (e.g., motor).

Figure 3A:
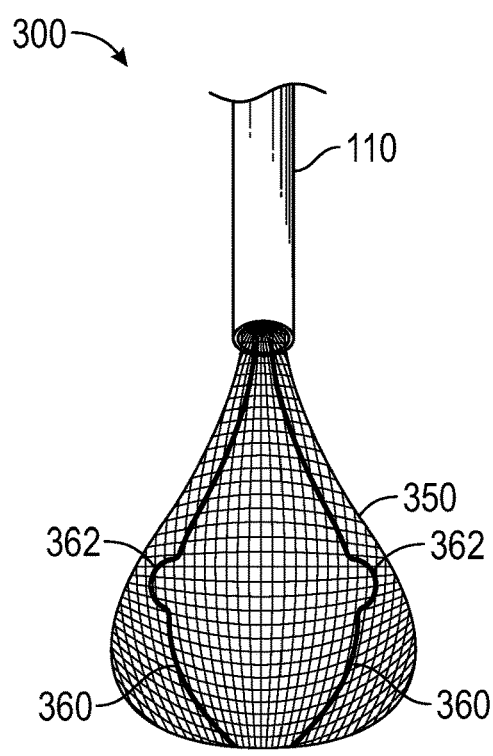
FIG. 3A shows a perspective view of an extraction device, in accordance with one or more embodiments of the present disclosure.
Figure 3B:
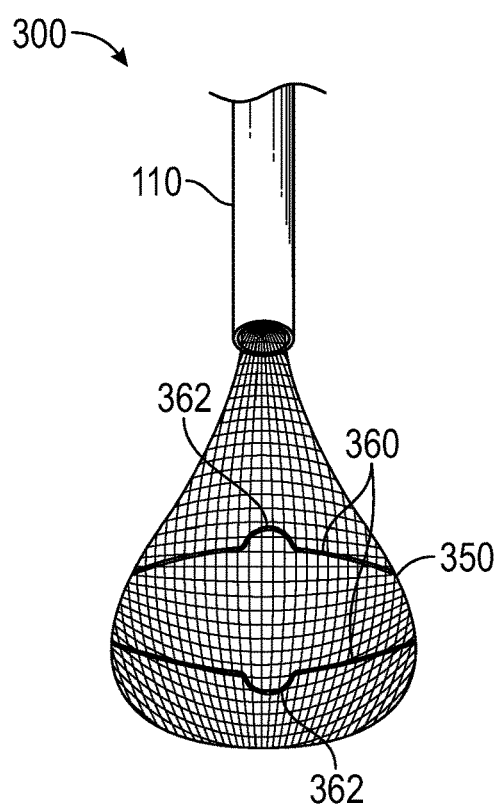
FIG. 3B shows a perspective view of an extraction device, in accordance with one or more embodiments of the present disclosure.

According to some embodiments, for example as shown in FIGS. 3A and 3B, an extraction device 300 can include a cover 350 that is advanceable and retractable over and around a target region. The extraction device 300 can further include one or more support bands 360 positioned on, within, or against the cover 350. The support bands 360 can provide a degree of rigidity to the cover 350, to urge the cover 350 to conform to a particular shape. The support bands 360 can be biased to a particular shape. For example, the support bands 360 can be a shape memory alloy. The support bands 360 can extend along a portion or an entirety of a length or width of the cover 350. As shown in FIG. 3A, the support bands 360 can extend in a generally longitudinal direction. As shown in FIG. 3B, the support bands 360 can extend in a generally circumferential direction. Each of the support bands 360 can include one or more bends 362 to facilitate bending along the length of the support band 360. The support bands 360 can be advanced and retracted with the cover 350, independent of any other wires (e.g., wires 130, 140, not shown in FIGS. 3A and 3B).

Figure 4:
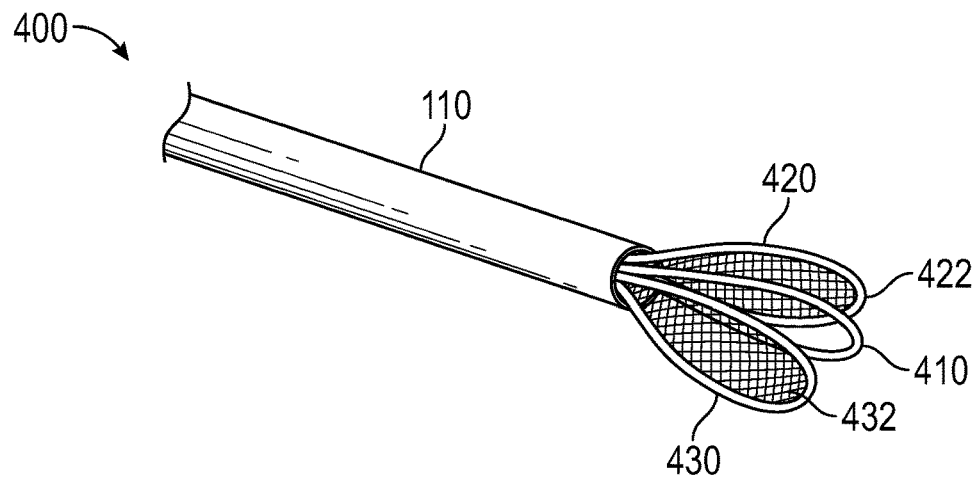
FIG. 4 shows a perspective view of an extraction device, in accordance with one or more embodiments of the present disclosure.

According to some embodiments, for example as shown in FIG. 4, an extraction device 400 can include a delivery shaft 110 having a lumen and a distal end and a dissection tool 410 distal to the distal end of the delivery shaft 110. The dissection tool 410 can be a wire loop or any other mechanism for dissecting a lens. The dissection tool 410 can be aligned along a central axis of the delivery shaft 110. A first capture portion 420 can be positioned on a first side of an axis of the delivery shaft 110. The first capture portion 420 can include a first cover 422. A second capture portion 430 can be positioned on a second side of an axis of the delivery shaft 110. The second capture portion 430 can include a second cover 432. The first capture portion 420 and the second capture portion 430 are configured to move toward the axis upon actuation and define an enclosed space between the first cover 422 and the second cover 432. The first capture portion 420 and the second capture portion 430 can be actuated, for example, by at least partial retraction into the delivery shaft 110. The dissection tool 410 can be used to dissect the lens after actuation of the first capture portion 420 and the second capture portion 430. Alternatively, or in combination, the dissection tool 410 can be retracted into the delivery shaft 110 prior to actuation of the first capture portion 420 and the second capture portion 430. The first cover 422 and the second cover 432 can be an elastomer.

Figure 5A:
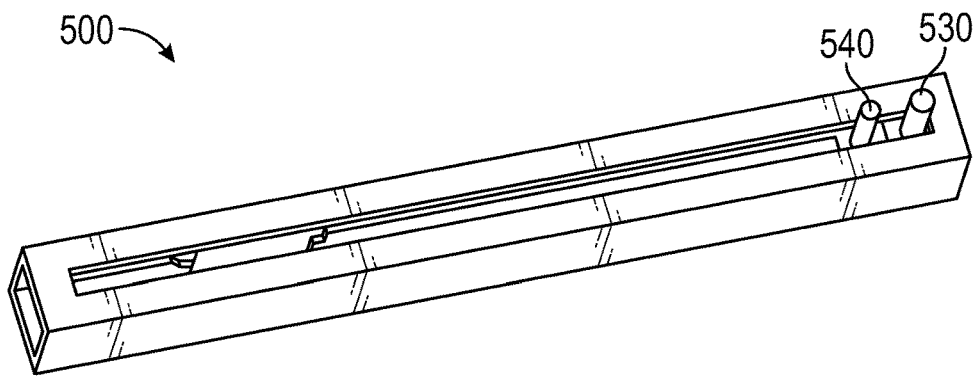
FIG. 5A shows a perspective view of an interface tool, in accordance with one or more embodiments of the present disclosure.
Figure 5B:
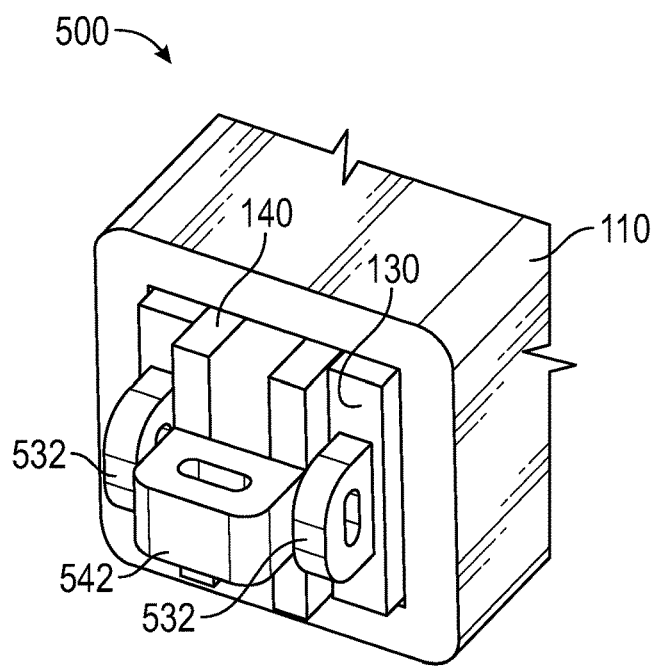
FIG. 5B shows a perspective view of the interface tool of FIG. 5A, in accordance with one or more embodiments of the present disclosure.

According to some embodiments, for example as shown in FIGS. 5A and 5B, deployment and retraction of components described herein can be achieved by an interface tool 500. The interface tool 500 can include a first control mechanism 530 and the second control mechanism 540. The first control mechanism 530 can connect, via a first interface 532, to the first wire 130 or another component described herein. The second control mechanism 540 can connect, via the second interface 542, to the second wire 140 or another component described herein. Actuation of the first control mechanism 530 and the second control mechanism 540 can separately controllably deploy, retract, and/or rotate components attached thereto. According to some embodiments, the cross section of the slide mechanism can be various shapes including circular (e.g., one tube within another which allows for rotational motion in addition to translational motion).

Figure 6A:
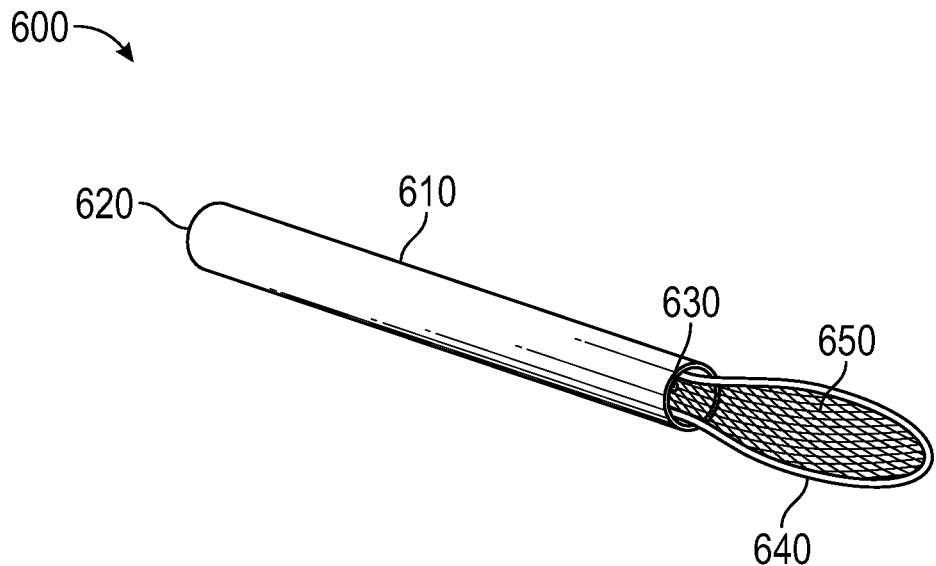
FIG. 6A shows a perspective view of an extraction device, in accordance with one or more embodiments of the present disclosure.
Figure 6B:
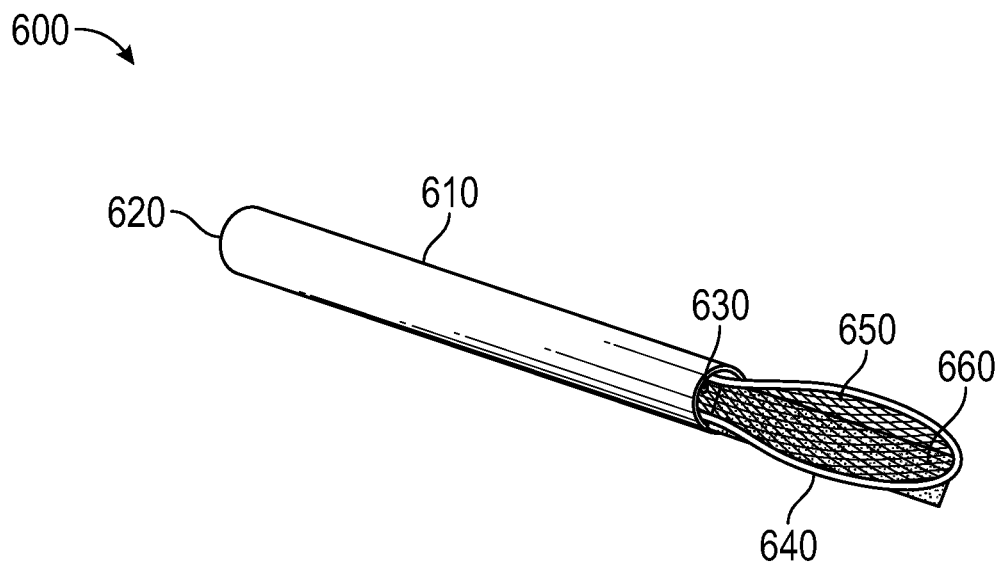
FIG. 6B shows a perspective view of the extraction device of FIG. 6A, in accordance with one or more embodiments of the present disclosure.

According to some embodiments, for example as shown in FIGS. 6A and 6B, an extraction device 600 can include a delivery shaft 610 having a lumen and a distal end. The extraction device 600 can further include an infusion port 620 for connecting a syringe or other fluid source to an irrigation port 630 at a distal end of the delivery shaft 610. The extraction device 600 can further include a loops 640 attached to the distal end of the delivery shaft 610. The loop 640 can be configured to be positioned under a lens to pull the lens out of the eye as irrigation and/or aspiration is provided from the irrigation port 630. A cover 650 can extend across an opening of the loop 640 and attach at a periphery of the loop 640. The extraction device 600 can further include a blade 660 that extends from an interior portion of the delivery shaft 610 to extend across at least a portion of an opening of the loop 640. The blade 660 can perform a cutting action upon the lens or other tissue encountered along its path. The blade 660 can be metal, silicone, or a rigid material. The blade 660 can be advanced until it reaches a distal end of the loop 640. The blade 660 can travel along a track defined by the loop 640. An interior space can be defined between the blade 660 and the cover 650 for capturing materials. The loop 640 and the blade 660 can be retracted into the lumen of the delivery shaft 610, along with any materials captured therein.

According to some embodiments, a method for using extraction devices described herein includes making an incision (e.g., an incision of less than 4 millimeters (mm)) to enter an anterior chamber of an eye. A capsulorhexis is performed. The lens is hydrodissected and/or hydrodelineated so that the lens changes position from being entirely within the natural capsular bag to being partially or completely displaced from the capsular bag. Viscoelastic may be used to further position the lens for optimum approach by an extraction device. The extraction device is introduced through the incision and advanced forward. An encircling structure (e.g., capture region 120) is introduced through the lumen of the device and advanced towards the lens. The encircling structure is positioned so that it surrounds the lens. Further deployment of the encircling structure may allow for multiple elements to expand and further encompass the lens. A second structure (e.g., cover 150) is advanced from the lumen of the device distally. The second structure covers the encircling structure from proximal to distal and substantially conforms to the encircling structure geometry. The encircling structure is retracted back into the lumen and may or may not twist as it is being retracted so that the lens is segmented into pieces smaller than the original whole lens. The encircling structure may or may not be advanced and retracted several times to further segment the lens. The second structure is then retracted in whole or in segments so that any remaining lens material within the structure is retracted into the lumen. The second structure can expand distally to allow for all the lens material to fit into the lumen. The entire device is removed from the anterior chamber of the eye. A second suction device is used to remove any remaining lens materials. The lens bag is reformed with viscoelastic to receive an artificial intraocular lens for reversal of aphakia and refractive correction.

Figure 7:
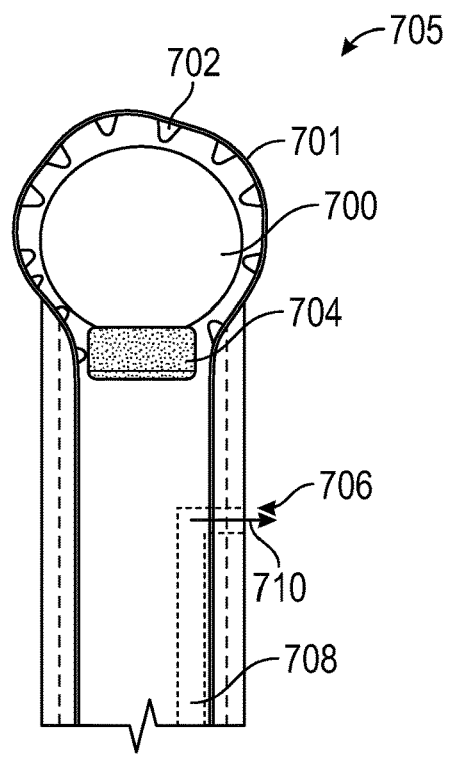
FIG. 7 shows a perspective view of an extraction device, in accordance with one or more embodiments of the present disclosure.

According to some embodiments, for example as shown in FIG. 7, nitinol wire(s) 701 of an extraction device 705 can grab the lens 700. The wires 701 can be surrounded by a mesh or other means to encapsulate the lens. The wires can contain teeth 702 or other means to firmly hold onto the lens 700. The wires 701 can spin the lens 700 in the plane that is shown if the distal part of the wire is pulled while the proximal part is advanced. This can be done using a wheel or other mechanism, or the wire can simply tension the lens against the lumen when it is retracted slightly. A recessed area contains a rotating element 704 that is abrasive or sharp to break the lens 700 into pieces. As the lens 700 is pulled into the recessed area by the wire 701, the abrasive rotating element 704 is actuated mechanically with gears or another mechanism to break up the lens. The lumen of the device has another port 706 and tube 708 within it that allows for fluid irrigation when connected to a pressurized fluid source. Fluid 710 can be aspirated by connecting the main lumen to a vacuum mechanism.

Figure 8:
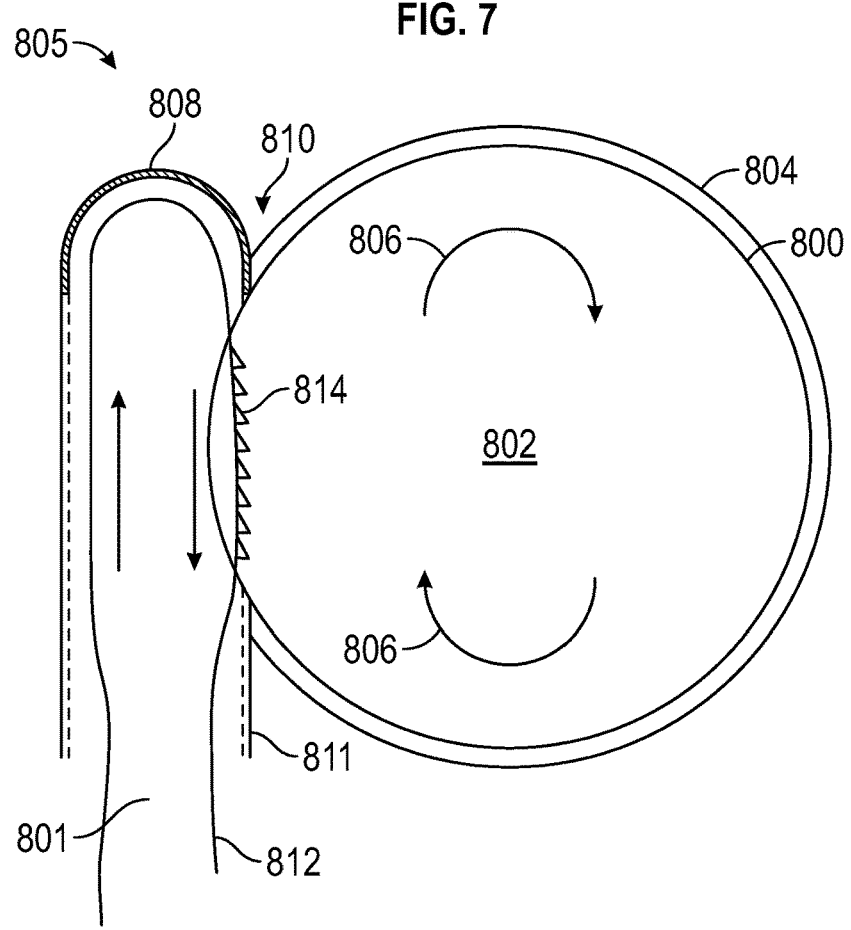
FIG. 8 shows a perspective view of an extraction device, in accordance with one or more embodiments of the present disclosure.

According to some embodiments, for example as shown in FIG. 8, one or more nitinol wires 800 of device 805 grabs the lens 802. The wires 800 can be surrounded by a mesh 804 or other means to encapsulate the lens. The wires can have features like the ones described for FIG. 1A. The wires can spin the lens as shown by the large arrows 806 or tension the lens against a recessed space within the lumen 801. Note that the end 808 of the lumen 801 is capped and the opening 810 is in the wall 811 of the tube. Within the lumen there is wire 812 with jagged cutting edges 814 (e.g., like a bandsaw). When the lens is tensioned against the bandsaw, the bandsaw can be mechanically actuated to break up the lens. This design can also have an irrigation and aspiration port.

Figure 9:
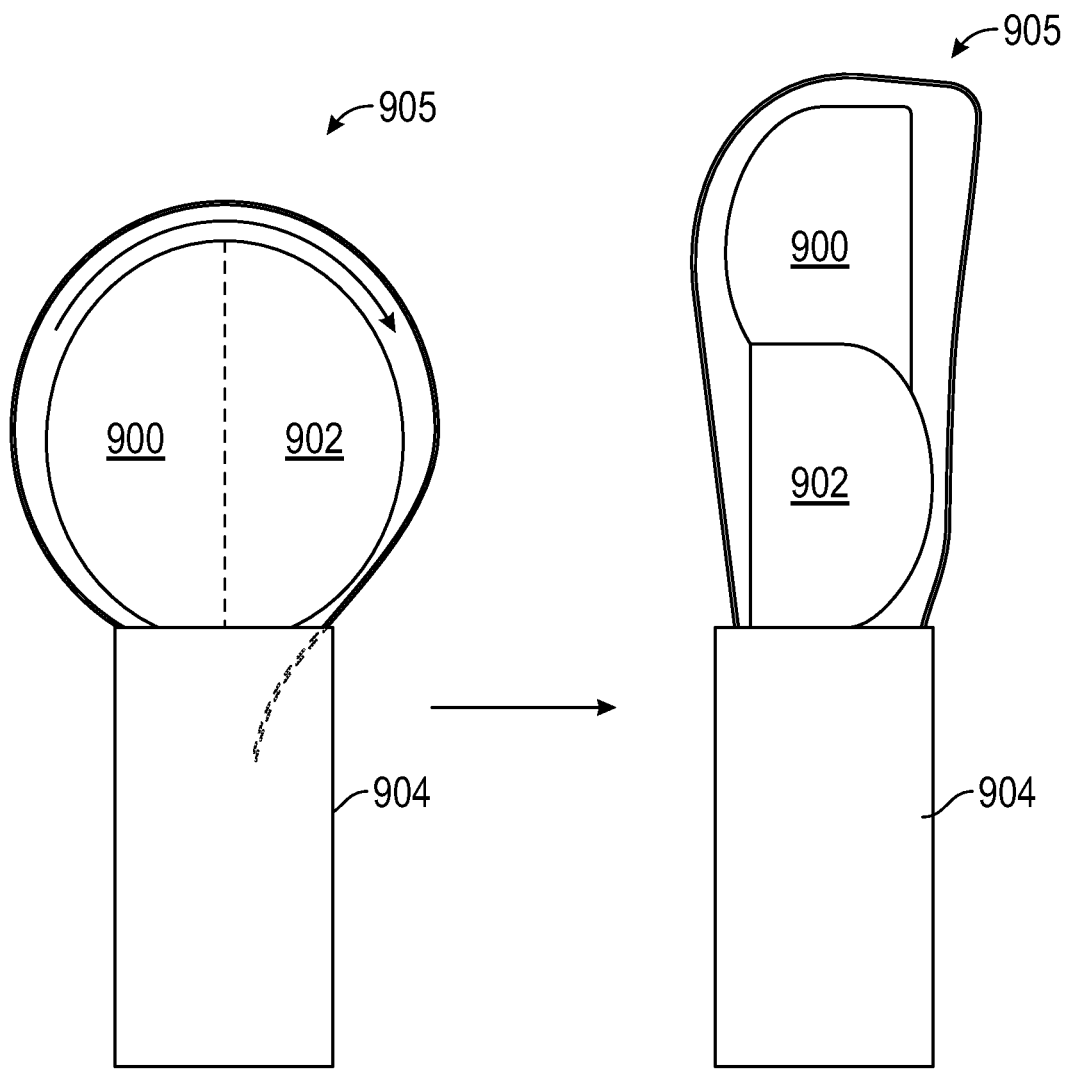
FIG. 9 shows a perspective view of an extraction device, in accordance with one or more embodiments of the present disclosure.

According to some embodiments, for example as shown in FIG. 9, first and second structures 900 and 902 of a device 905 can expand distally to allow for all the lens material to fit into the lumen. In this way, lens material can be squeezed and extended to be able to fit into the lumen 904 of the device.

Figure 10A:
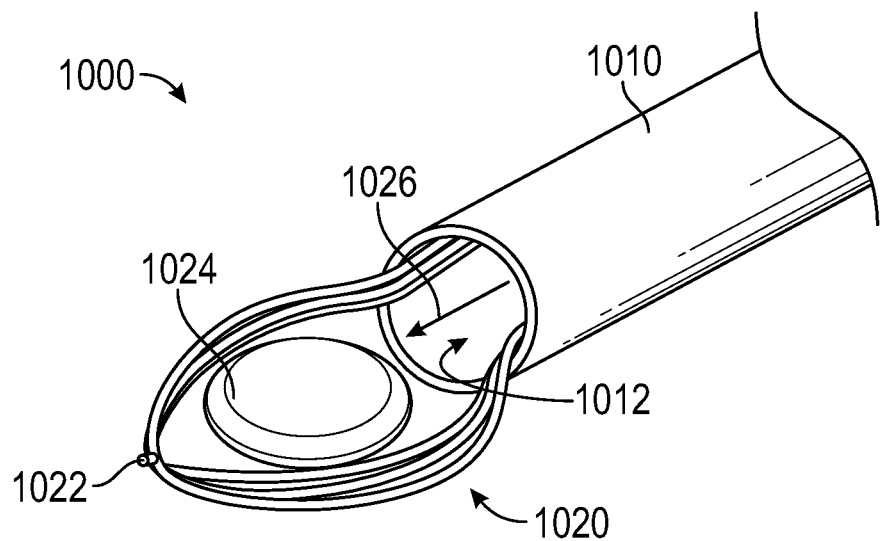
FIG. 10A shows a perspective view of an extraction device, in accordance with one or more embodiments of the present disclosure.

According to some embodiments, for example as shown in FIGS. 10A-10E, an extraction device 1000 can include a plurality of rings 1020 that extend in a direction 1026 from a lumen 1012 of a delivery shaft 1010 to encapsulate a sample or specimen 1024 (e.g., some or all of a lens). Rings 1020 may, for example, be concentric wire rings that are pivotally bound at a joint 1022 at a distalmost end. In the configuration of FIG. 10A, rings 1020 have been deployed out of the lumen 1012 (e.g., by a manually or automatically controlled mechanism such as a push rod as described above in connection with FIGS. 5A and 5B).

Figure 10B:
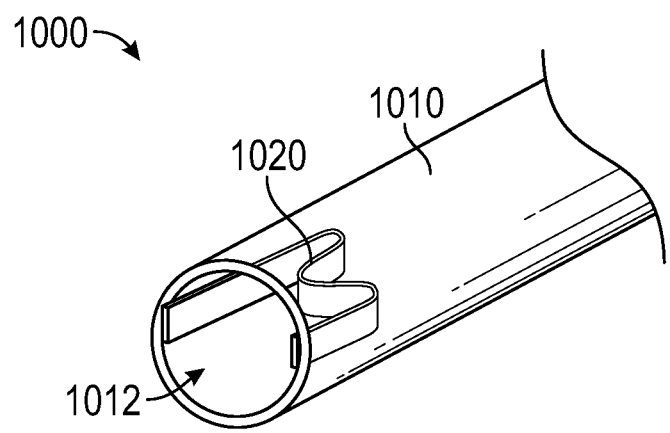
FIG. 10B shows a perspective view the extraction device of FIG. 10A, in accordance with one or more embodiments of the present disclosure.
Figure 10C:
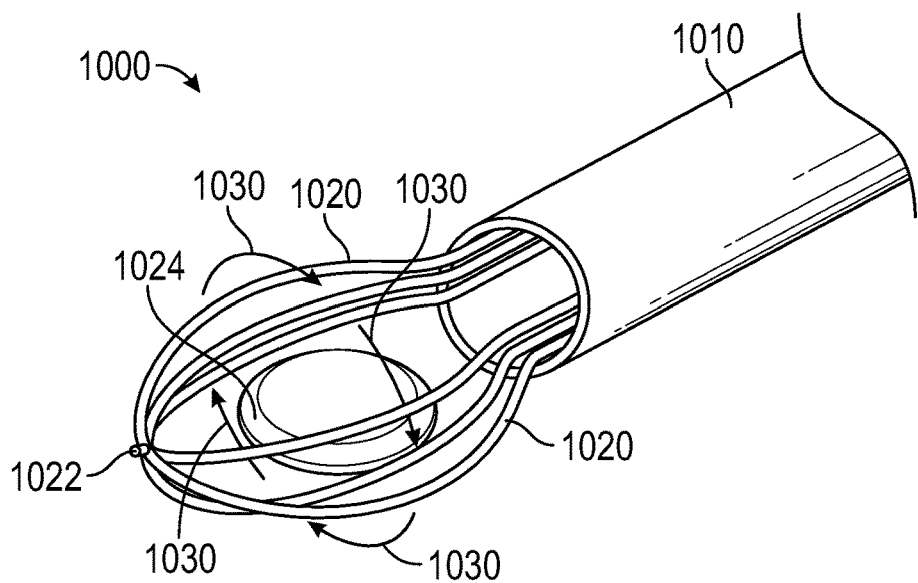
FIG. 10C shows a perspective view of the extraction device of FIG. 10A, in accordance with one or more embodiments of the present disclosure.
Figure 10D:
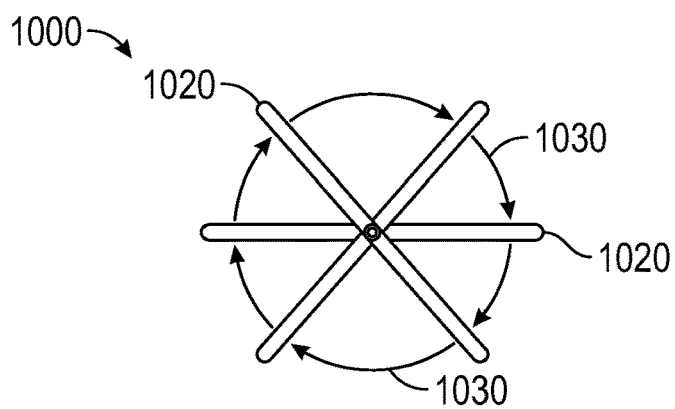
FIG. 10D shows an end view of the extraction device of FIG. 10A, in accordance with one or more embodiments of the present disclosure.
Figure 10E:
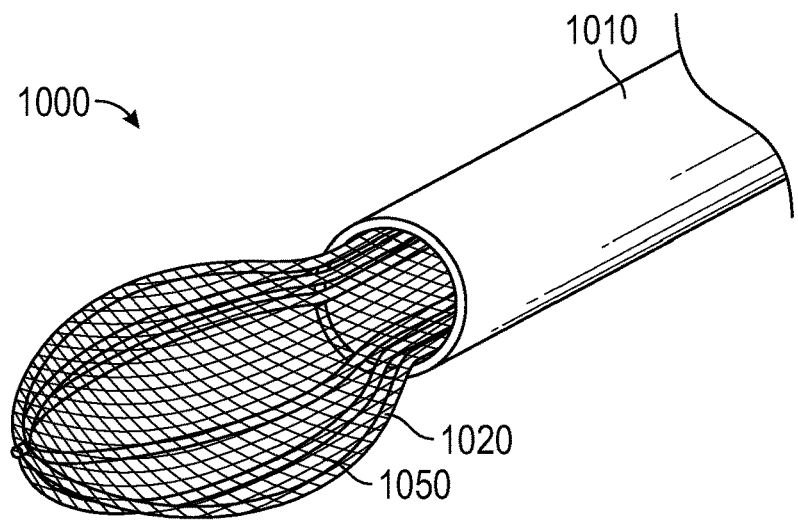
FIG. 10E shows a perspective view of the extraction device of FIG. 10A, in accordance with one or more embodiments of the present disclosure.

As shown in FIG. 10B, prior to deployment, rings 1020 may be folded within the distal end of lumen 1012. In this way, rings 1020 can be stored within shaft 1010 during insertion through an incision. As shown in FIG. 10C, rings 1020 may be rotated (e.g., in the direction of arrows 1030) relative to each other such that rings 1020 encapsulate and substantially surround sample 1024. FIG. 10D shows a top view of rings 1020 following rotation of the rings in directions as indicated by arrows 1030 to an encapsulated configuration.

Following encapsulation of the sample, a mesh cover or bag 1050 as discussed herein may be extended over rings 1020 (e.g., using guides similar to guides 160 above) to substantially surround and encapsulate the sample 1024 within bag 1050. In some embodiments, once sample 1024 is encapsulated within rings 1020 and bag 1050, rings 1020 may be pulled back into lumen 1012. As rings 1020 are withdrawn into lumen 1012, rings 1020 may cut sample 1024 into fragments to aid in withdrawing the sample into lumen 1012. After cutting of sample 1024 with rings 1020, bag (or cover) 1050 may be withdrawn into lumen 1012 to retrieve and extract the sample.

Figure 11A:
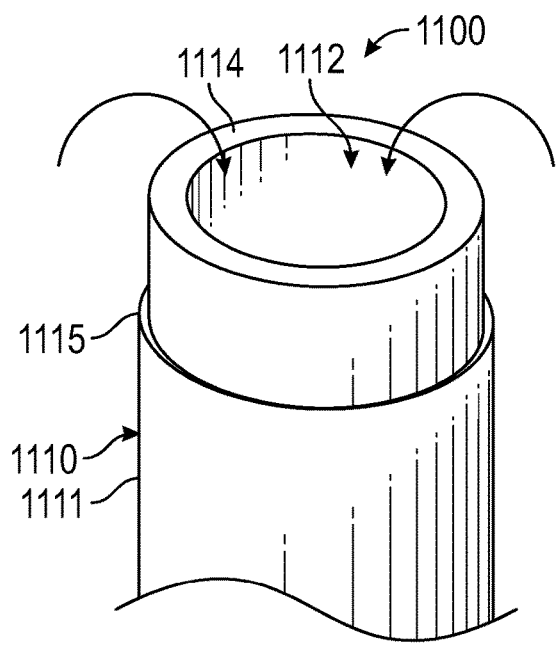
FIG. 11A shows a perspective view of an extraction device, in accordance with one or more embodiments of the present disclosure.
Figure 11B:
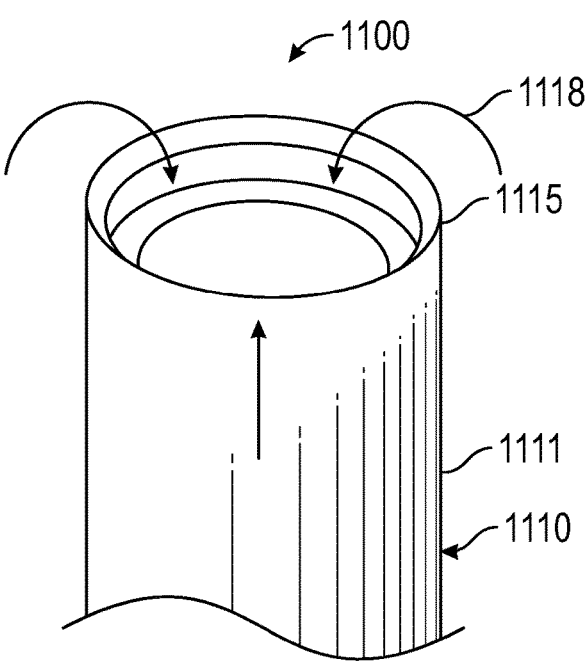
FIG. 11B shows a perspective view the extraction device of FIG. 11A, in accordance with one or more embodiments of the present disclosure.

According to some embodiments, for example as shown in FIGS. 11A and 11B, an extraction device 1100 can include a shaft 1110 having an inner cylindrical shaft structure 1114 with a lumen 1112 and an outer shaft structure 1111 with a sharp cutting edge 1115 at a distalmost end thereof. As shown in FIG. 11B, cutting edge 1115 of outer shaft structure 1111 can be extended beyond the distalmost end of inner shaft structure 1114 to excise tissue. Suction can be provided that draws tissue excised by cutting edge 1115 into lumen 1112 as indicated by arrows 1118.

Figure 12A:
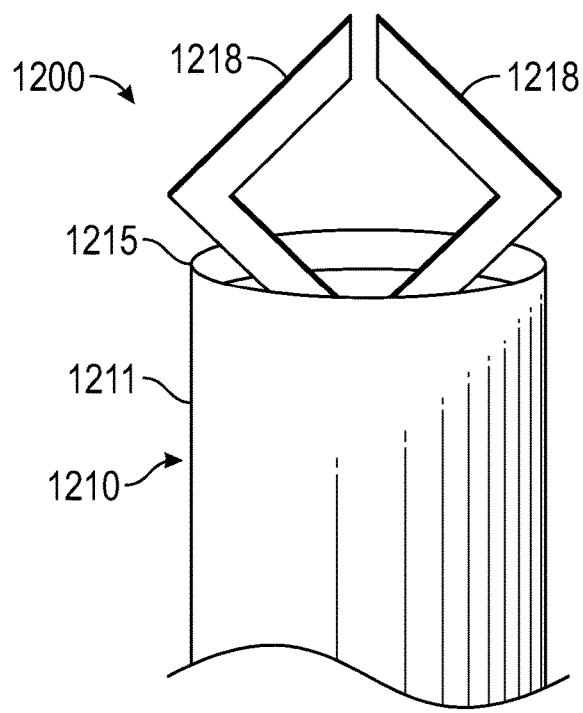
FIG. 12A shows a perspective view of an extraction device, in accordance with one or more embodiments of the present disclosure.
Figure 12B:
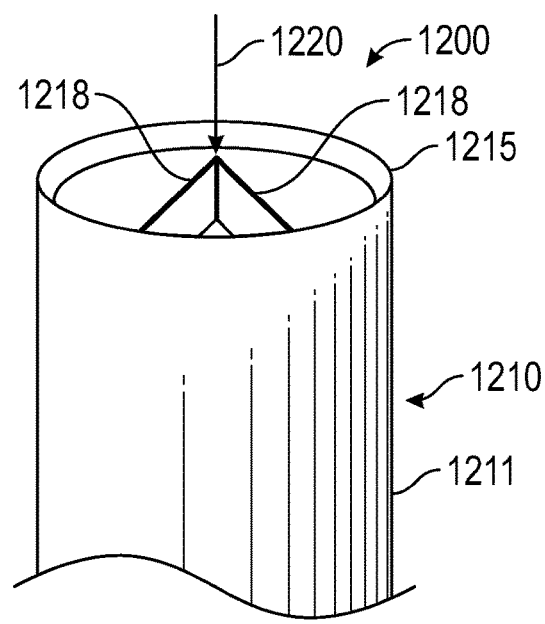
FIG. 12B shows a perspective view the extraction device of FIG. 12A, in accordance with one or more embodiments of the present disclosure.

According to some embodiments, for example as shown in FIGS. 12A and 12B, an extraction device 1200 can include a shaft 1210 including an outer shaft structure 1211 with a sharp cutting edge 1115 at a distalmost end thereof. As shown in FIG. 12A, gripping structures such as forceps 1218 may be extended from within shaft 1210 to grip tissue to be excised. As shown in FIG. 12B, as forceps 1218 are withdrawn into shaft 1210 in direction 1220, the tissue held by forceps 1218 can be cut free by cutting edge 1215. The forceps 1218 and/or suction can be provided that draws tissue excised by cutting edge 1215 into shaft 1210 for removal of the tissue.

Figure 13A:
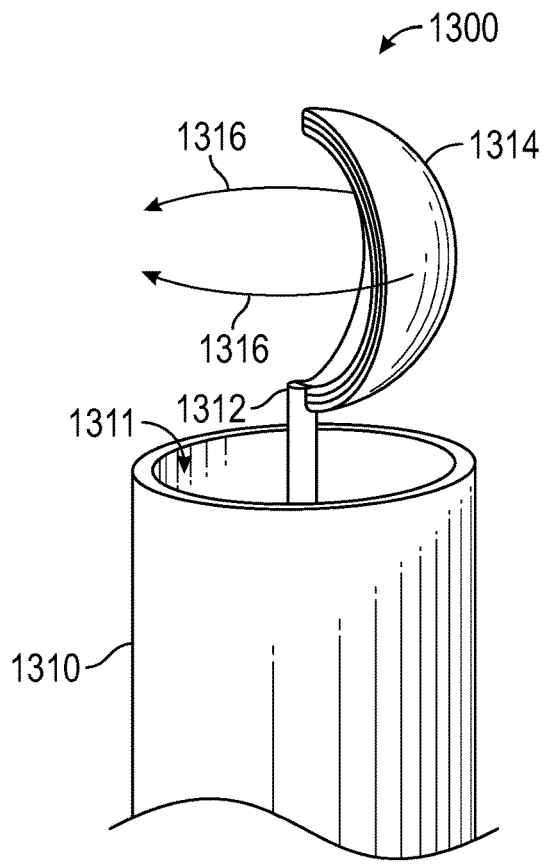
FIG. 13A shows a perspective view of an extraction device, in accordance with one or more embodiments of the present disclosure.
Figure 13B:
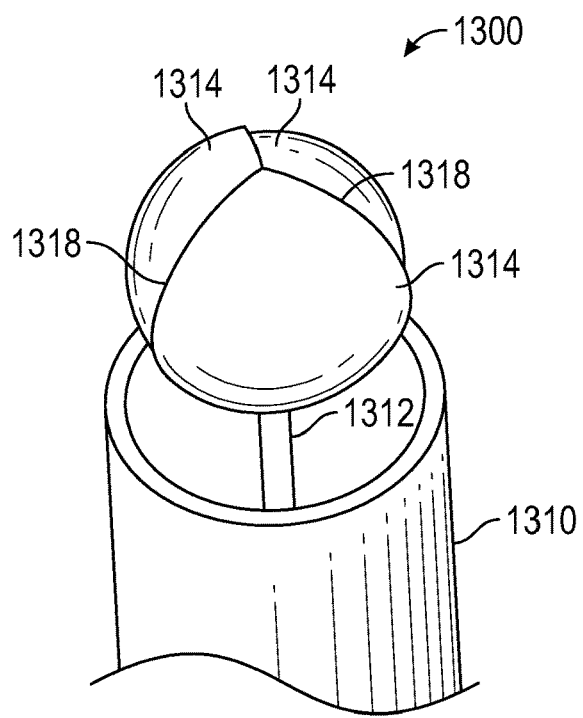
FIG. 13B shows a perspective view the extraction device of FIG. 13A, in accordance with one or more embodiments of the present disclosure.

According to some embodiments, for example as shown in FIGS. 13A and 13B, an extraction device 1300 can include a shaft 1310 having a lumen 1311 and an excision member that extends therefrom. The excision member may include a control shaft 1312 and one or more layered cutting and encapsulation leaves 1314. In the layered configuration of FIG. 13A, the excision member may have a concave scoop shape with a reduced profile for insertion through an incision. Layered cutting and encapsulation leaves 1314 may be reticulated relative to each other about an axis as indicated by arrows 1316 to create an enclosure for a lens or portion thereof as shown in the encapsulation configuration of FIG. 13B.

In some embodiments, one or more of leaves 1314 may have a cutting edge 1318 thereon that, when that leaf 1314 is rotated about the axis of, for example, shaft 1312, cuts through and excises the tissue to be encapsulated. In other embodiments, edges of leaves 1314 may be blunt edges that slide between the lens and its surrounding tissue to encapsulate substantially the entire lens prior to removal. In some embodiments, a cutting and/or suction mechanism can be applied within the encapsulated region formed by leaves 1314 (e.g., via an inner lumen of shaft 1312 into the encapsulated region to break up the encapsulated lens and suction out the broken up lens before re-stacking or re-layering leaves 1314 for withdrawal of device 1300.

Figure 14A:
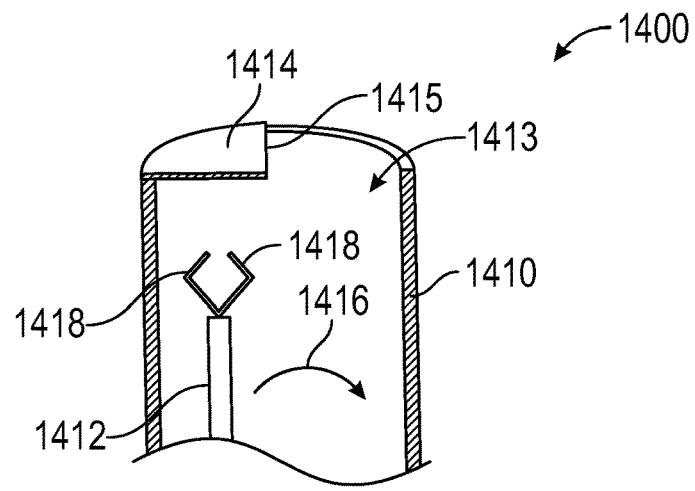
FIG. 14A shows a perspective view of an extraction device, in accordance with one or more embodiments of the present disclosure.
Figure 14B:
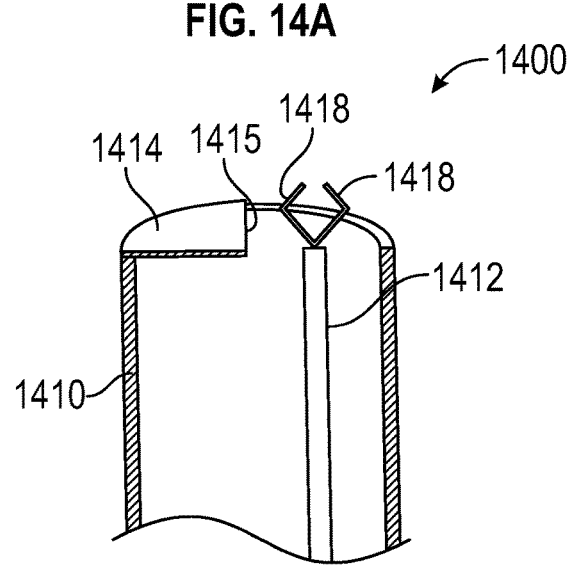
FIG. 14B shows a perspective view the extraction device of FIG. 14A, in accordance with one or more embodiments of the present disclosure.
Figure 14C:
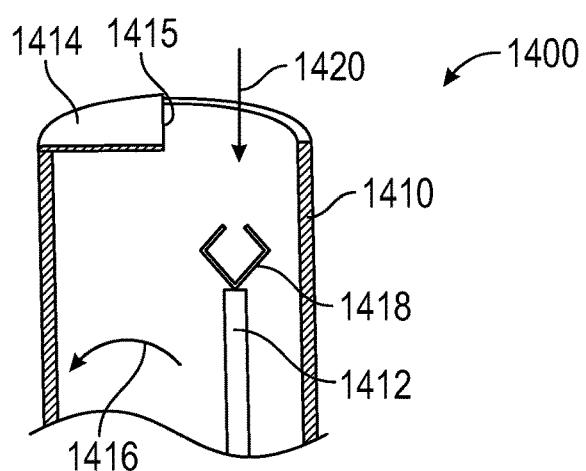
FIG. 14C shows a perspective view the extraction device of FIG. 14A, in accordance with one or more embodiments of the present disclosure.

According to some embodiments, for example as shown in FIGS. 14A-14C, an extraction device 1400 can include a shaft 1410 having a lumen 1413 with a partial lid structure 1414 for the lumen. Partial lid structure 1414 may include a sharp cutting edge 1415. In the example of FIG. 14A, partial lid 1414 extends perpendicularly to the axis of shaft 1410 to cover a portion of lumen 1413. However, this is merely illustrative, and partial lid 1414 (and cutting edge 1415) can be positioned at angles other than 90 degrees with respect to the axis of shaft 1410.

As shown in FIG. 14A, forceps 1418 may be movably disposed within lumen 1413 for grasping or gripping of tissue. In the embodiment of FIGS. 14A-14C, a twisting action may be performed to excise tissue using an axis that is off-center to the cutting edge 1415. For example, as shown in FIG. 14B, forceps 1418 may be extended out of lumen 1413 by inner shaft 1412 to grasp tissue to be excised. The tissue may be grabbed, suctioned, and/or drawn into lumen 1413 (as indicated by arrow 1420 of FIG. 4C) and moved relative to the cutting edge 1415 to cause an excision. The tissue can be moved by fixing the cutting edge and rotating forceps 1418 (e.g., as indicated by arrow 1416 of FIGS. 4A and 4C) and/or by rotating shaft 1410 to rotate cutting edge 1415 relative to the tissue that is held by forceps 1418 (e.g., to reduce the potential of lens movement or rotation during excision that can damage the capsule). Grasping, suctioning, and/or rotating of tissue relative to cutting edge 1415 can be repeated to excise portions of a lens or other tissue until all of the desired tissue is removed.

Figure 15A:
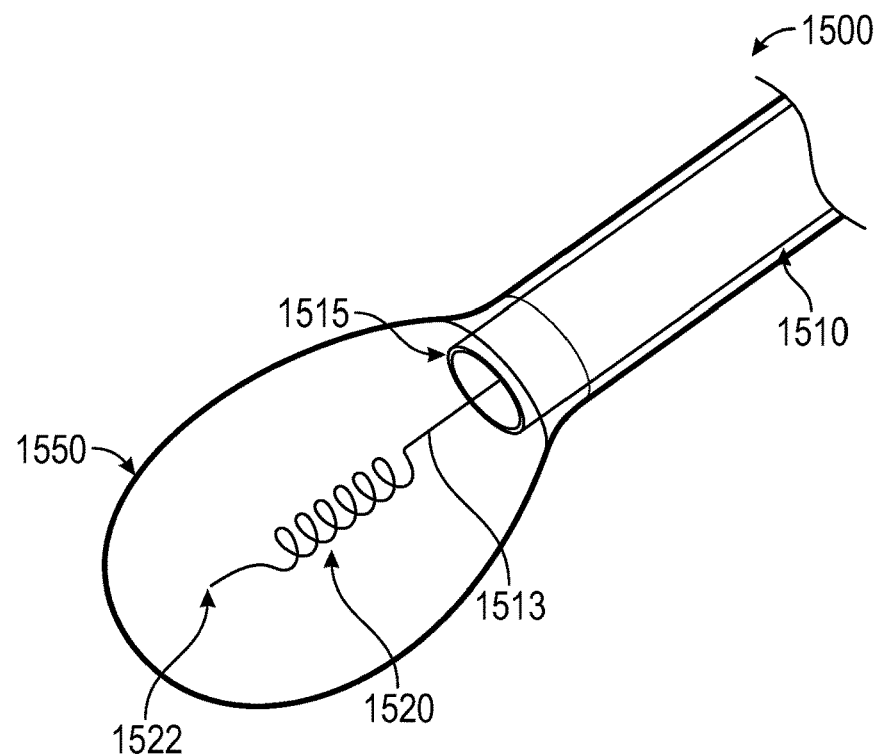
FIG. 15A shows a perspective view of an extraction device, in accordance with one or more embodiments of the present disclosure.
Figure 15B:
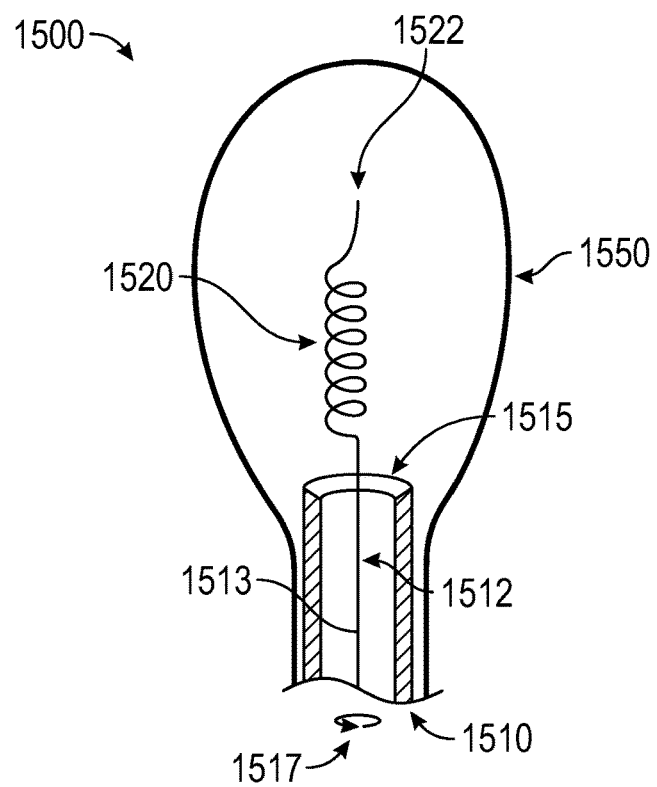
FIG. 15B shows a cross-sectional view the extraction device of FIG. 15A, in accordance with one or more embodiments of the present disclosure.

According to some embodiments, for example as shown in FIGS. 15A and 15B, an extraction device 1500 can include a shaft 1510 having a lumen 1512 and a wire 1513 having a helical wire section 1520. Wire 1513 may be extendible from within the lumen 1512 at the distalmost end thereof. Shaft 1510 may include a sharp cutting edge 1515 at the distalmost end thereof. Wire 1513 may have a sharp piercing tip 1522 so that helical wire section 1520 can be rotated into a sample in a manner similar to a corkscrew to penetrate and grip the sample to be removed.

As shown, a mesh cover or bag 1550 may be deployed from shaft 1510 (in a manner similar to the cover extension operations as discussed above in accordance with one or more embodiments) to encapsulate the sample to be removed. FIG. 15B shows a cross-sectional view of shaft 1510 showing how cutting edge 1515 may include an angled surface at the end of shaft 1510 relative to the axis of shaft 1510.

In the example of FIGS. 15A and 15B, shaft 1510, having cutting edge 1515, may be inserted into the anterior chamber of a patient's eye to deploy wire 1513 (e.g., a metallic wire as described herein) having piercing tip 1522 and a helical section 1520. As the wire 1513 is deployed, the wire tip 1522 pierces a specimen to be removed and may be rotated as indicated by arrow 1517 to envelop into the specimen. Bag 1550 (e.g., a silicone bag or other cover) may be deployed around the specimen and pulled back into shaft 1510. This extraction (e.g., the pull-back of bag 1550) may cause edge 1515 to cut through the specimen to allow the specimen to enter into lumen 1512.

According to some embodiments, for example as shown in FIGS. 16A-16E, an extraction device 1600 may include a shaft 1610 having an inner lumen from which a wire 1630 extends. Wire 1630 may be a deployable wire that is extendible from the distalmost end of shaft 1610 or may be permanently deployed. Wire 1630 may have a sliding side 1632 and a fixed side 1634.

FIGS. 16A and 16B show device 1600 with a tip 1601 in a fully closed state (FIG. 16A), and an open state (FIG. 16B). Device 1600 may be a device for cataract extraction which is configured to enter the eye of a patient through a small incision in a somewhat cylindrical shape as in the configuration of FIG. 16A. As shown, device 1600 may have a tubular shaft 1610 which houses the cataract capturing components (labeled as segments 1630A, 1630B, and 1630F). Segments 1630A, 1630B, and 1630F may be fully retractable into tubular shaft 1610 (e.g., to make entering the eye easier), or may remain outside tubular shaft 1610 as depicted in FIG. 16A. Segments 1630A, 1630B, and 1630F may be joined at a hinge point 1639.

Once in the eye, tip 1601 of device 1600 may be forced to change shape by sliding segment 1630A to make it deform into a bow shape. This deformation may open the mouth of a basket formed to scoop up the lens. Segment 1630F may be fixed from moving in relation to segment 1630A. In addition to opening the mouth of the basket by deforming segment 1630A, the length of the basket may extended by sliding segment 1630B (see, e.g., FIGS. 16C-16E) in the same manner as segment 1630A, but in a different direction (e.g., 90 degrees different) from that of segment 1630A, causing segment 1630B to deform into a long bow shape.

Figure 16C:
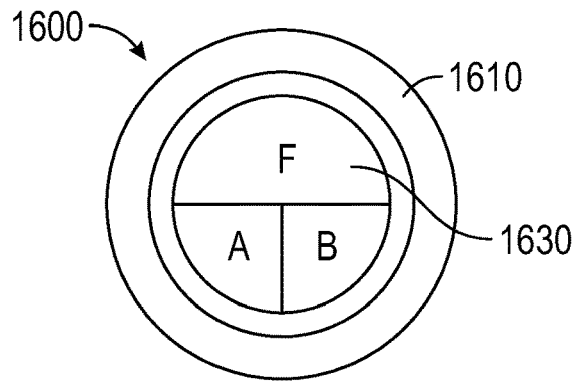
FIG. 16C shows a top view the extraction device of FIG. 16A, in accordance with one or more embodiments of the present disclosure.
Figure 16D:
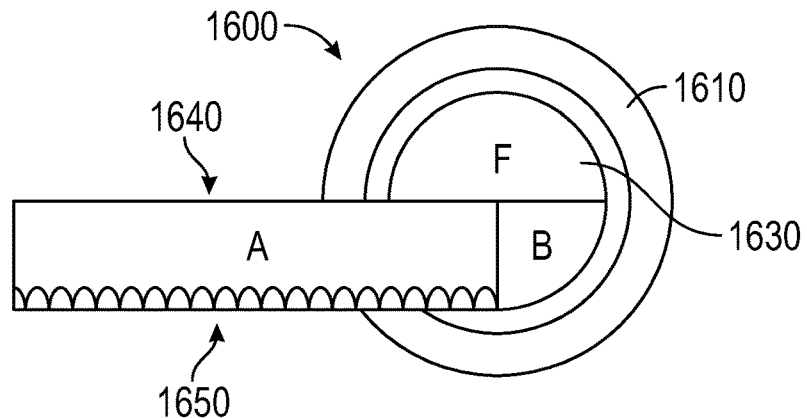
FIG. 16D shows a top view the extraction device of FIG. 16A, in accordance with one or more embodiments of the present disclosure.
Figure 16E:
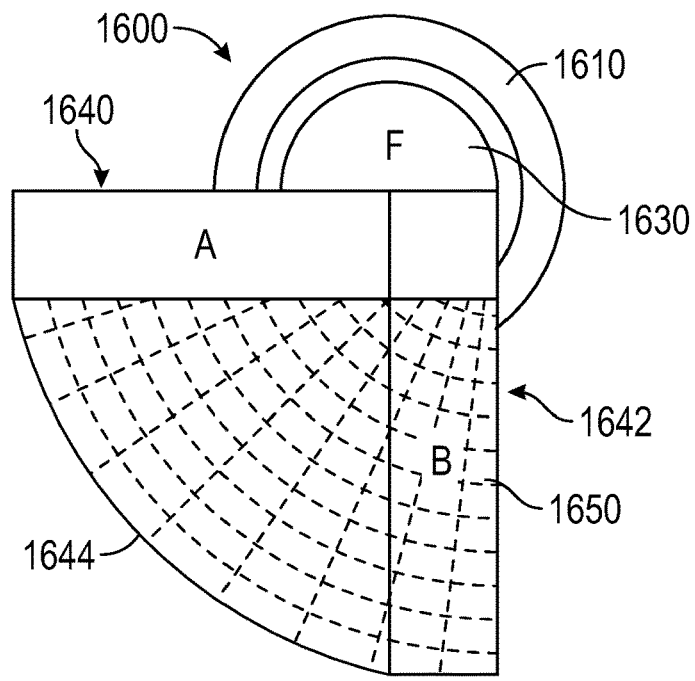
FIG. 16E shows a top view the extraction device of FIG. 16A, in accordance with one or more embodiments of the present disclosure.

As segment 1600B is deformed, segment 1600B may stretch open a bag or net-like cover structure 1650 as shown in FIGS. 16D and 16E. With segments 1630A and 1630B fully extended as in the configuration of FIG. 16E, device 1600 may look somewhat like a butterfly net, which can be used to capture the lens to be removed. After capturing the lens, the entire assembly may be pulled down into tubular shaft 1610 to crush the lens enough to reduce the size, such that it can be withdrawn through the small incision in the eye.

The top view of FIG. 16C shows device 1600 in a fully closed state, as seen in FIG. 16A from the side view. In the top view of FIG. 16D, segment 1630A has been forced to deform such that the mouth 1640 of the basket opens. The configuration of FIG. 16D corresponds to that of FIG. 16B which shows, from the side, the bowed shape of segment 1630A, and how segment 1630A was slid up the tubular shaft while segment 1600F was held fixed in position. In the configuration of FIG. 16E, segments 1630A and B have been forced to deform such that the length 1642 of the basket 1644 is formed and the bag or net structure 1650 was deployed.

Figure 17A:
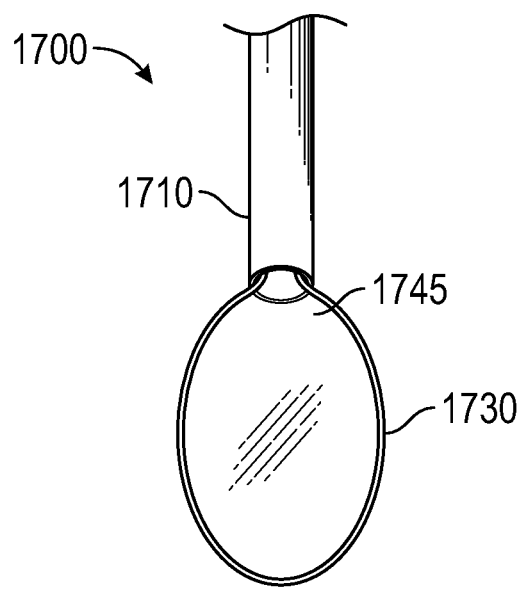
FIG. 17A shows a front view of an extraction device, in accordance with one or more embodiments of the present disclosure.
Figure 17B:
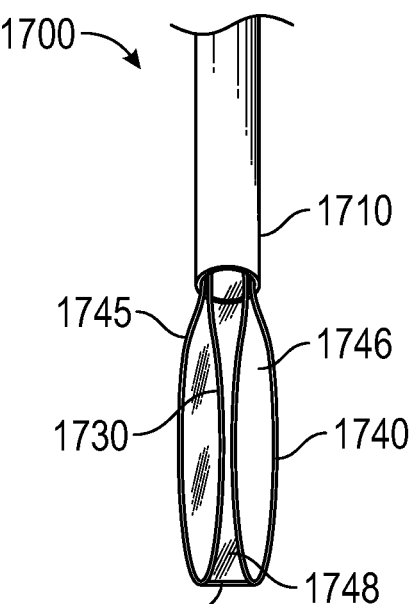
FIG. 17B shows a side angle view the extraction device of FIG. 17A, in accordance with one or more embodiments of the present disclosure.
Figure 18:
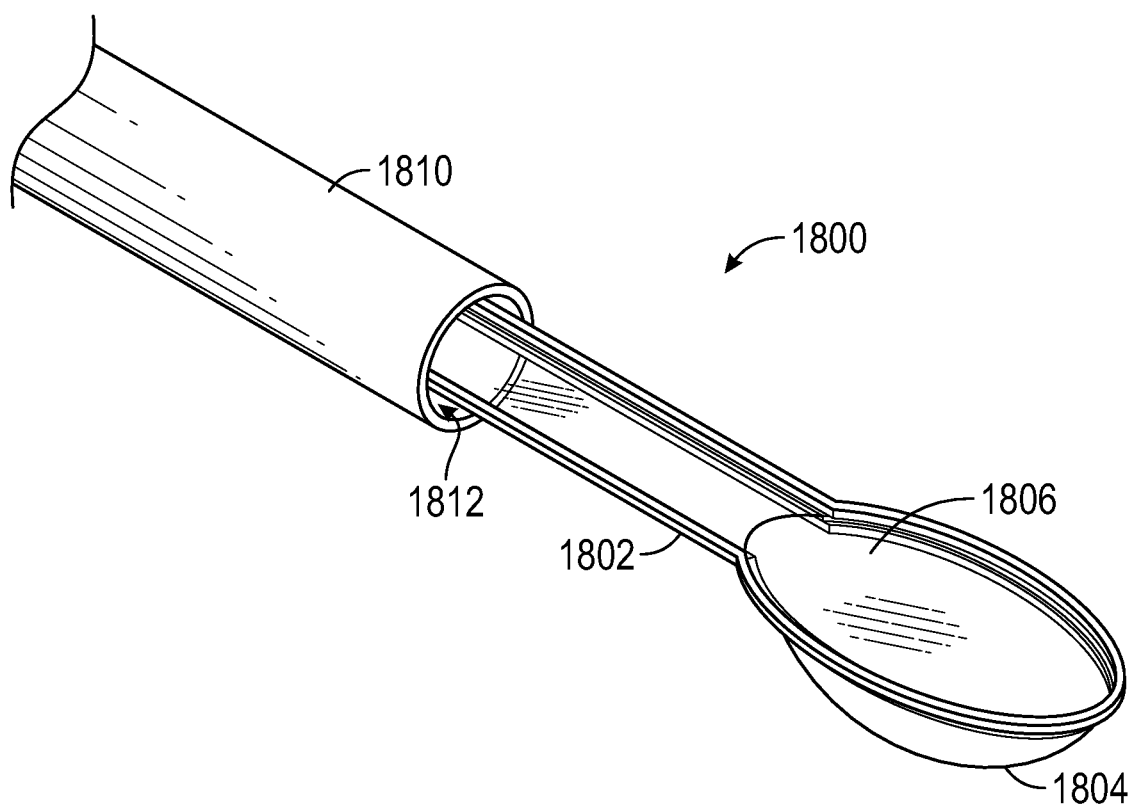
FIG. 18 shows a perspective view of an extraction device, in accordance with one or more embodiments of the present disclosure.
Figure 19:
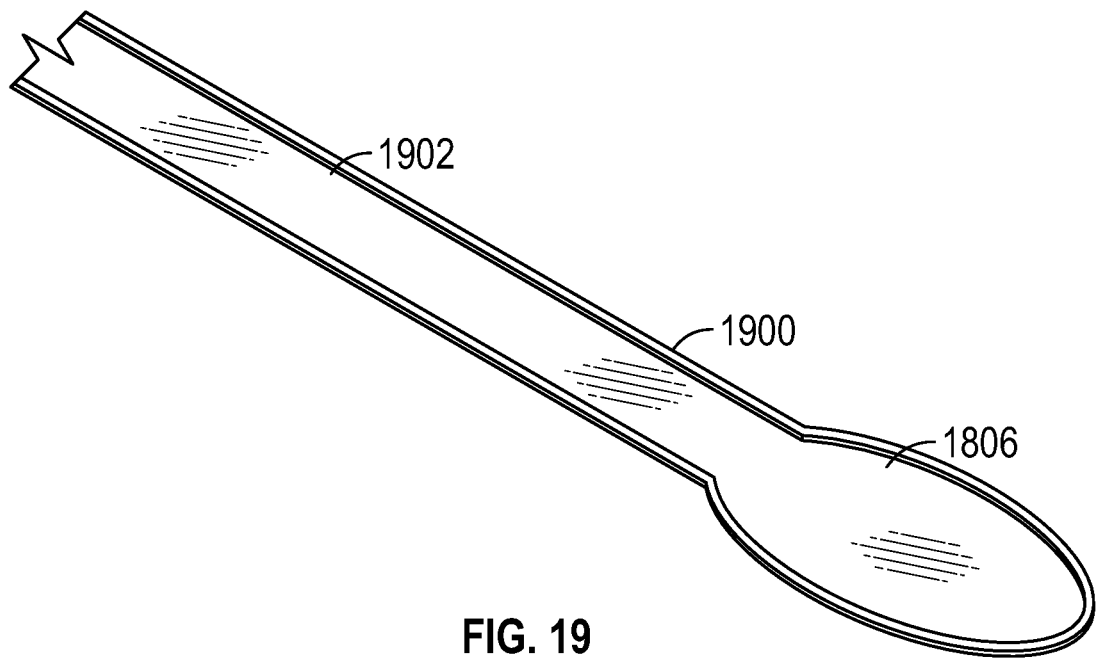
FIG. 19 shows a perspective view of a lid structure for the extraction device of FIG. 18, in accordance with one or more embodiments of the present disclosure.

According to some embodiments, for example as shown in FIGS. 17A and 17B, an extraction device 1700 may include a first ring 1730 and a second ring 1740 that are extendible from a shaft 1710. Ring 1730 (e.g., a metal ring such as a NiTi ring) may be provided with a film such as a PTFE film 1745 that spans the ring. Second ring 1740 (e.g., a metal ring such as a NiTi ring) may be an open ring having an opening 1746 that is free of any film.

In the embodiment of FIGS. 17A and 17B, shaft 1710 may form an inserter that can be inserted into an incision (e.g., a 2.75 mm incision). For example, in some embodiments, the internal diameter of shaft 1710 may be 2.2 mm and the outer diameter of shaft 1710 may be 2.4 mm. Rings 1730 and 1740 may be deployed from the inserter behind a hydrodissected lens. Rings 1730 and 1740 may be opened up and separated from each other slightly (e.g., to a distance of 2 mm apart). Rings 1730 and 1740 may be bridged by a film 1747 (e.g., PTFE film) with ring 1730 covered with, for example, PTFE 1745 and ring 1740 open (i.e., not covered by PTFE or other films). The lens may then be guided through the open ring 1740 to sit against the film 1745 that bridges the other ring 1730 (e.g., so that the natural lens is sitting in an open basket 1748 formed by rings 1730 and 1740 and films 1745 and 1747). Once the cataract/lens is in place in the basket 1748, the two rings can then be separated apart from each other by another 2 mm so that the entire lens is in the "basket" 1748. Once the cataract is in the basket 1748, a "lid" (not shown) to the basket may be slid over the open space 1746 in ring 1740. The lid (e.g., formed by an additional ring with, e.g., PTFE covering) can slide in on small slots within ring 1740 for a smooth and controlled deployment of the lid. In some embodiments, one or more additional rings (e.g., 50 micron rings) may be deployable into and/or out of the basket 1748 for further cutting of a sample/lens therein.

In the example of FIGS. 17A and 17B, film 1745 is shows as a substantially planar film. However, in some embodiments, a multi-ring scoop extraction device may be provided with a ring having a film that forms a basket shape. An example embodiment of a multi-ring scoop extraction device 1800 is shown in FIGS. 18-23.

According to some embodiments, for example as shown in FIGS. 18-23, an extraction device 1800 may include ring frames that are extendible from a lumen 1812 of a shaft 1810. In the example of FIGS. 18-23, extraction device 1800 includes a first (e.g., nitinol) frame 1802 that has a polymer or mesh bag 1804 attached thereto.

Device 1800 may also include an additional (e.g., nitinol) frame 2002 (see, e.g., FIGS. 20 and 21) that can be deployed into and out of lumen 1812 independently of the first frame 1802. Initially, frame 2002 may be deployed when the initial bag/frame 1804/1802 component is deployed so that second frame 2002 sits just below frame 1802 as shown in the cross-sectional views of FIGS. 20 and 22.

Device 1800 may also include a third frame 1900 (e.g., a nitinol frame) with a covering 1902 that forms a lid 1806 for basket 1804 when third frame 1900 is deployed. Covering 1902 may be a polymer or mesh covering or, in some embodiments, may contain relatively more rigid or solid material to provide additional strength and structure to frame 1900 for cutting of lens tissue as discussed in further detail hereinafter. In use, one or more of the following tasks may be performed.

In a first task, after a capsulorhexis has been performed and a lens of a patient's eye has been hydrodissected out of the natural position (e.g., so that the lens is sitting on the equator and partially in the iris plane), an introducer such as shaft 1810 may be inserted into the patient's eye (e.g., via an incision). In a second task, frame 1802 with bag 1804 and frame 2002 may be deployed into the anterior chamber of the eye. In a third task, the lens may be approached and guided partially into the bag 1804 so that, for example, half the lens is in this artificial bag 1804. In a fourth task, lid 1806 on frame 1900 may then be introduced such that lid 1806 and frame 1900 transect (e.g., bisect) the lens so that a portion (e.g., substantially half) of the lens is in encapsulated within a cavity defined by the bag 1804 and lid 1806 and a remaining portion (e.g., a remaining half) is outside of the cavity. In a fifth task, frame 2002 that was introduced into the eye along with frame 1802 may be withdrawn or retracted from within the cavity into the lumen 1812 of the introducer 1810 to further segment the portion of the lens that is sitting in the cavity between artificial bag 1804 and lid 1806. In a sixth task, the entire complex of all pieces in bag 1804 (e.g., in the cavity defined by bag 1804 and lid 1806) may then be retracted into the introducer 1810 to remove the portion of lens that is encapsulated therein. Introducer 1810 may then be removed from the eye and the segmented pieces are removed from the bag. The first through sixth tasks may be repeated for, for example, the other half lens that remains in the eye. Although the example tasks above have been described with a portion of the lens being encapsulated in the cavity defined by bag 1804 and lid 1806, in some scenarios, the entirety of a lens may be encapsulated within the cavity, transected by one or more frames 2002, and removed by withdrawing frames 1802 and 1900 into introducer 1810 (e.g., without transecting the lens with lid frame 1900 while extending the lid frame 1900).

Figure 20:
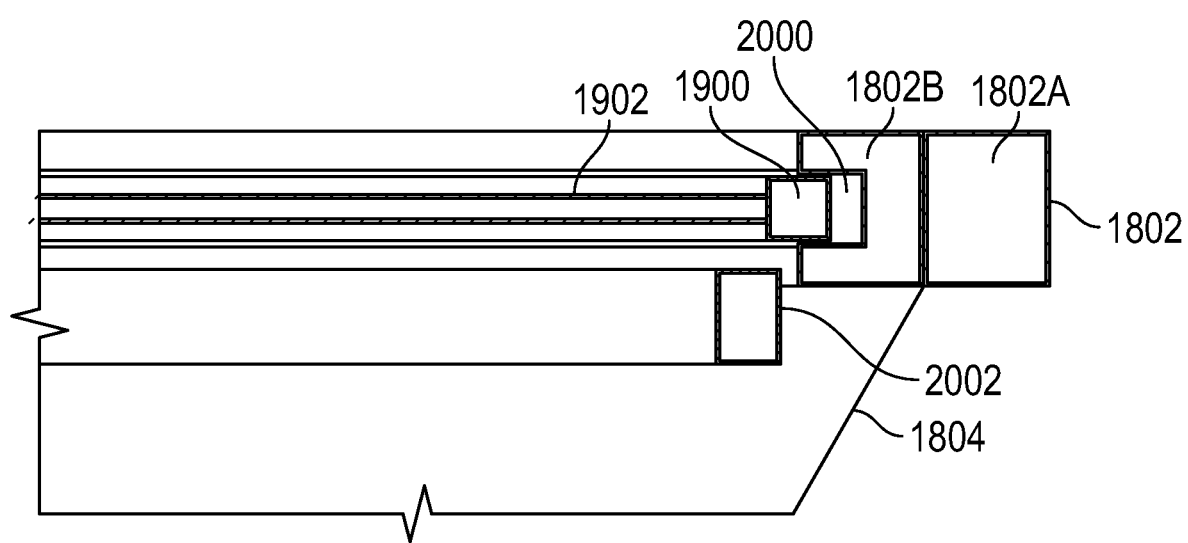
FIG. 20 shows a cross-sectional view of a portion of the extraction device of FIG. 18, in accordance with one or more embodiments of the present disclosure.
Figure 21:
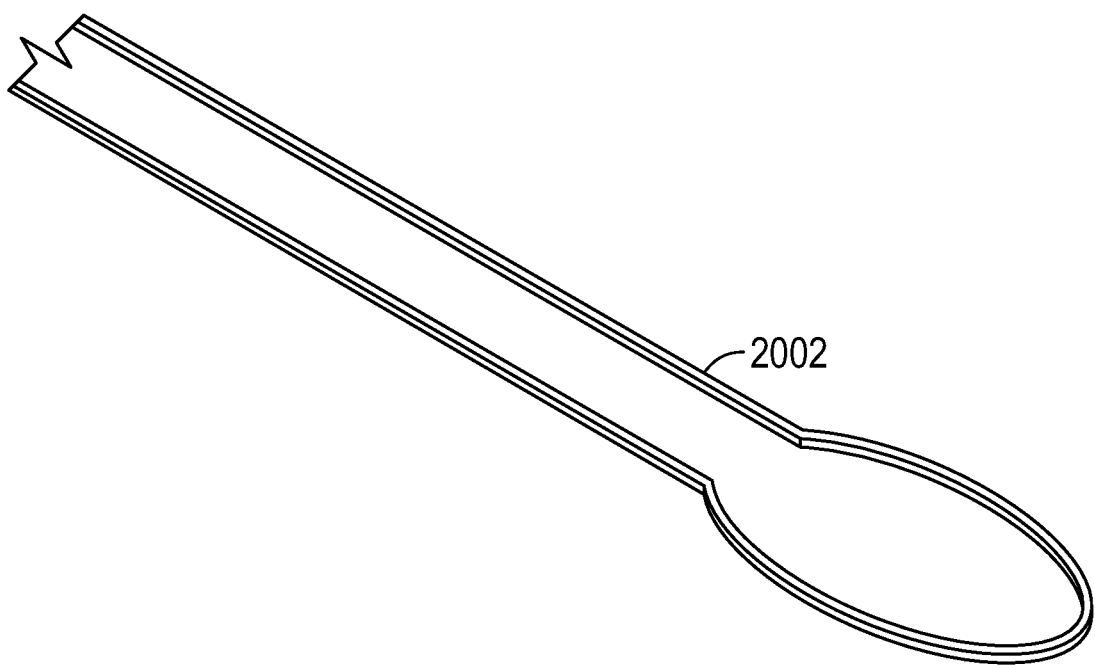
FIG. 21 shows a perspective view of a frame structure for the extraction device of FIG. 18, in accordance with one or more embodiments of the present disclosure.
Figure 22:
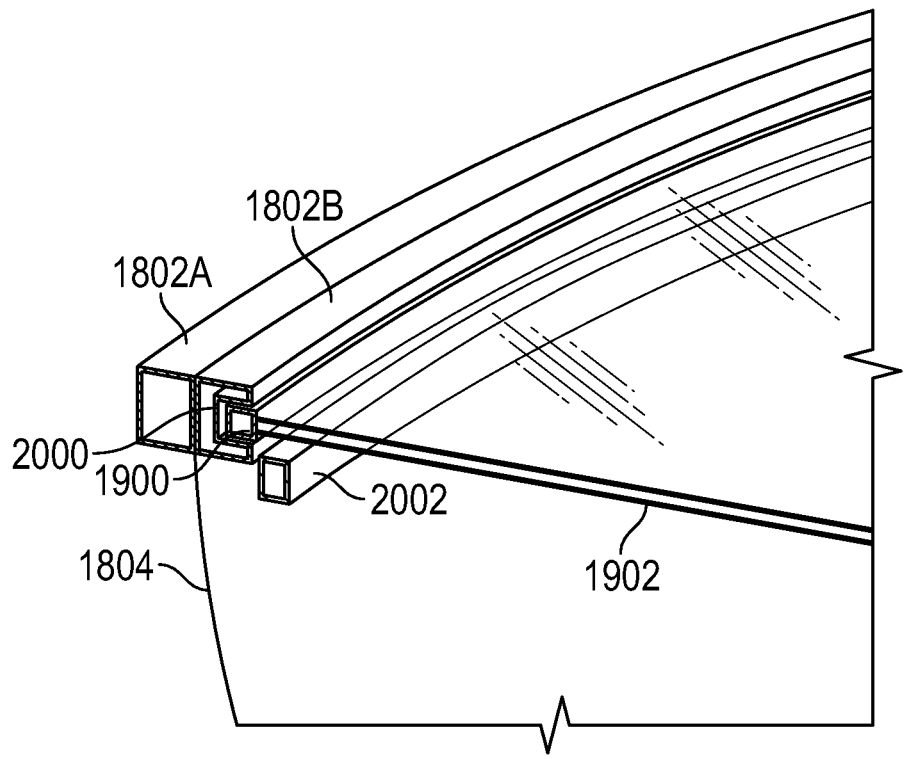
FIG. 22 shows a cross-sectional perspective view of a portion of the extraction device of FIG. 18, in accordance with one or more embodiments of the present disclosure.

As shown in the cross-sectional view of FIG. 20, lid frame 1900 may ride on an inside railing formed by a recess 2000 of the first frame 1802 (e.g., a recess in an inner portion 1802A of frame 1802 disposed interior to an outer frame portion 1802B) that contains the bag 1804. The leading end of the lid frame 1900 may be sharp so that frame 1900 can transect (e.g., bisect) the lens easily. In some embodiments, lid frame 1900 may be formed from two or more frame segments to facilitate advancement of the lid. For example, a segmented frame 1900 may be provided to allow for the lid frame 1900 to ride along the structure of the first frame 1802 with more precision (e.g., a bisected frame 1900 may ride on the rails of the first frame 1802 more easily than a monolithic frame).

Figure 23:
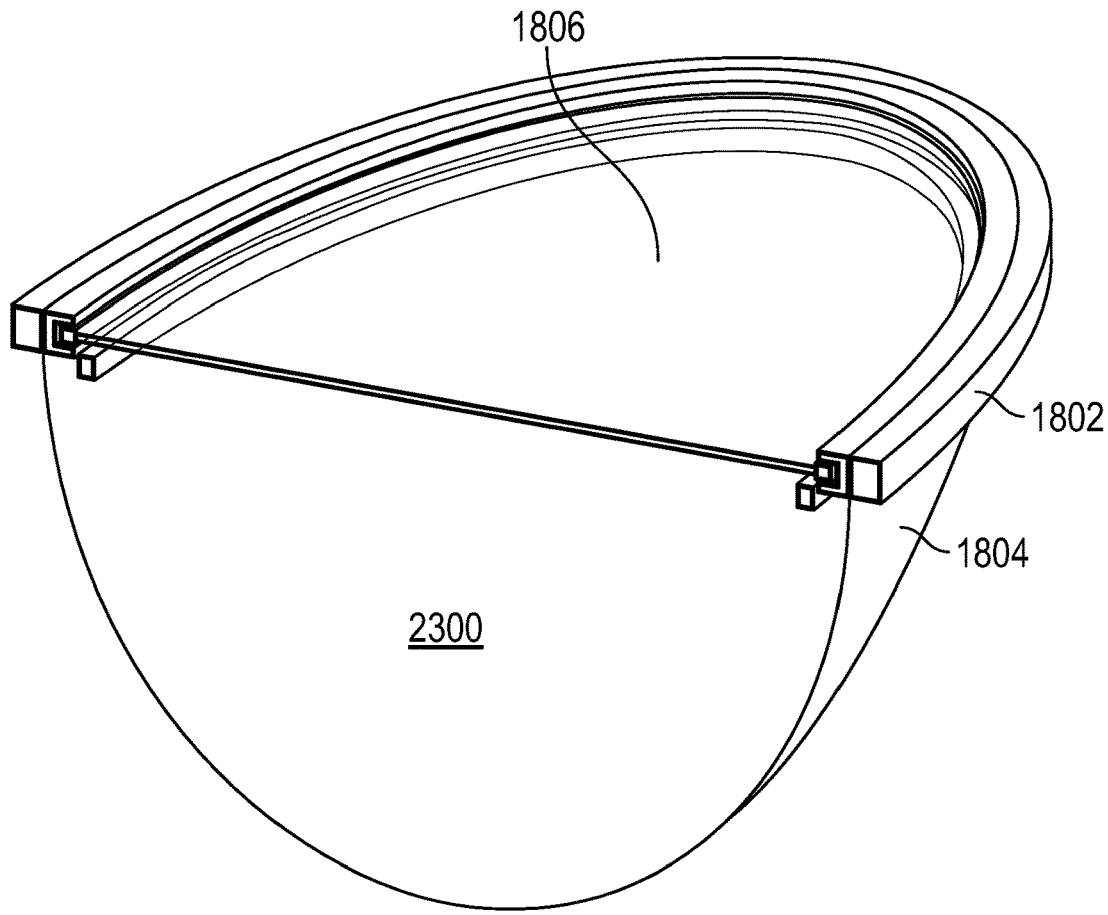
FIG. 23 shows a cross-sectional perspective view of a portion of the extraction device of FIG. 18, in accordance with one or more embodiments of the present disclosure.

In some embodiments, frame 2002 that is retracted after bagging the lens might be one of many such intermediate frames that are deployable and retractable such that the half lens that is bagged can be segmented multiple times with the multiple intermediate frames. For example, a plurality of frames 2002 may be stacked on top or next to each other for independent deployment and retraction for cutting actions. Although nitinol is often mentioned herein as an example material for frames and/or other components, frames 1802, 1900, and/or 2000 may be formed from nitinol or other metals or polymers in various embodiments. FIG. 23 shows a full cross-sectional perspective view of the cavity 2300 that is defined by and enclosed between bag 1804 and lid 1806 when deployed. Cavity 2300 may hold substantially half of a lens of a patient's eye as described herein for further dissection and removal.

Bag 1804 and/or lid 1806 can contain elastic or inelastic polymer or mesh materials. Shaft 1810 (sometimes referred to as an introducer or an injector) may be composed of metal, polymer or glass materials. The distal end of the introducer, in one or more embodiments, may contain flexible materials that expand when the bag is retracted back into the introducer. Shafts such as shaft 110 etc. described herein may be formed from sections of hypodermic tubing, sometimes referred to as a hypotube, according to some embodiments.

Although bag 1804 and lid 1806 are shown in various examples as continuous sheets of material attached to their respective frames, this is merely illustrative. In some implementations, bag 1804 and/or lid 1806 may be provided with one or more openings (not explicitly shown). The openings may be cutouts from a continuous sheet implemented bag or lid or may be openings in mesh sheets attached to the respective frames that form bag 1804 and/or lid 1806.

In configurations in which bag 1804 and/or lid 1806 are provided with one or more openings, after some or all of a lens of a patient's eye has been secured between bag 1804 and lid 1806 within the anterior chamber of the patient's eye, frames 1802 and/or 1900 may be withdrawn into delivery shaft 1810 such that parts of the secured lens (or portion thereof) are forced to exit the bag and/or lid through the openings into the anterior chamber as the bag and/or lid is being withdrawn into the distal end of the tube. In this way, bag 1804 and/or lid 1806 may be configured to act as a strainer for the lens (or portion thereof) that, upon withdrawal of frames 1802 and/or 1900 into the distal end of delivery shaft 1810, cause some or all of the lens come out through the openings as a ground or strained material that can be later removed (e.g., via suction) from the anterior chamber.

In configurations in which bag 1804 and/or lid 1806 are provided with one or more openings, a method of removing some or all of the lens of a patient's eye may include extending a first frame (e.g., frame 1802) having an attached flexible bag structure (e.g., bag 1804) with a plurality of openings from a distal end of a delivery shaft (e.g., shaft 1810) into an anterior chamber of an eye of a patient such that the flexible bag structure at least partially surrounds at least a portion of a lens of the eye of the patient; extending a second frame (e.g., frame 1900) having an attached lid structure (e.g., lid 1806) along the first frame to secure the at least the portion of the lens between the flexible bag structure and the lid structure; and withdrawing the first and second frames into the distal end of the delivery shaft to strain the at least the portion of the lens through the plurality of openings in the flexible bag structure into the anterior chamber.

The method may also include extending a third frame (e.g., frame 2002) into the eye of the patient together with the first frame; and, prior to withdrawing the first and second frames, withdrawing the third frame to transect the secured at least the portion of the lens, in one or more embodiments.

The method may also include suctioning the strained at least the portion of the lens from the anterior chamber, in one or more embodiments.

Figure 24:
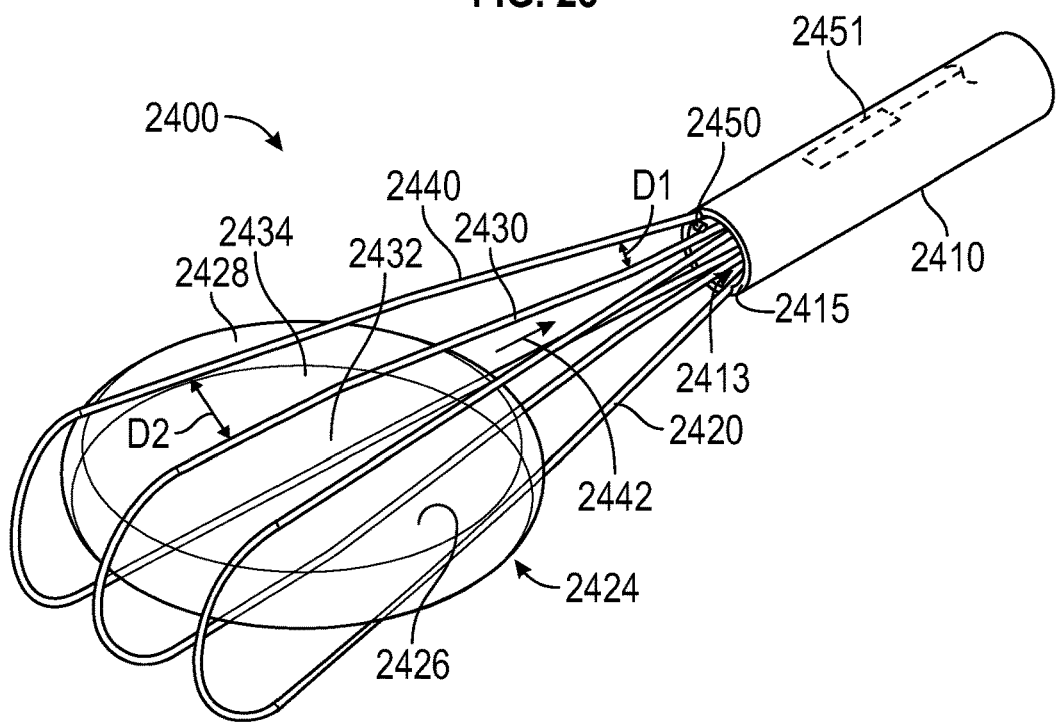
FIG. 24 shows a perspective view of a portion of an extraction device, in accordance with one or more embodiments of the present disclosure.

According to some embodiments, for example as shown in FIG. 24, an extraction device 2400 can include a delivery shaft 2410 having a lumen 2413 and a distal end 2415 from which one or more wires can extend. For example, as shown in FIG. 24, extraction device 2400 may be implemented as a three-wire snare having first wire 2420, second wire 2430, and third wire 2440. First wire 2420, second wire 2430, and third wire 2440 may each be a wire loop formed from metal (e.g., nitinol), plastic, and/or a shape memory material.

First wire 2420, second wire 2430, and third wire 2440 may be extended from distal end 2415 of delivery shaft 2410 and positioned to lasso or surround lens 2424 (e.g., within the eye following hydrodissection or hydrodelineation of the lens). Once first wire 2420, second wire 2430, and third wire 2440 are positioned around the lens as shown in FIG. 24, first wire 2420, second wire 2430, and third wire 2440 can be retracted back into lumen 2413 of delivery shaft 2410 (e.g., in direction 2442). As first wire 2420, second wire 2430, and third wire 2440 are retracted into lumen 2413, first wire 2420, second wire 2430, and third wire 2440 may be pulled through lens 2424 to split lens 2424 into four pieces 2426, 2428, 2430, and 2432. The four pieces 2426, 2428, 2432, and 2434 of lens 2424 may then each be removed from the eye (e.g., with a forceps that grabs and/or crushes the lens piece).

As shown in FIG. 24, when first wire 2420, second wire 2430, and third wire 2440 are in an extended position with respect to distal end 2415 of delivery shaft 2410, first wire 2420, second wire 2430, and third wire 2440 may be positioned such that the distance between each wire increases with increasing distance from distal end 2415 (e.g., from a first distance D1 near distal end 2215 of shaft 2410 to a second distance D2 that is greater than D1 near a distalmost end of the wire loops). First wire 2420, second wire 2430, and third wire 2440 may be positioned together within lumen 2413 and then separated during or after extension from lumen 2413.

For example, in one implementation, delivery shaft 2410 may include one or more features such as feature 2450 (e.g., an integral or attached extension from the inner surface of delivery shaft 2410 in lumen 2413) that causes first wire 2420, second wire 2430, and third wire 2440 to separate from each other as they are extended from distal end 2415 (e.g., as adjacent wires slide along opposing sides of feature 2450). Feature 2450 may be a protrusion extending from an inner surface of the delivery shaft in the lumen that causes the first, second, and third wire loops to separate upon extension from within the lumen.

As another example, after extension of first wire 2420, second wire 2430, and third wire 2440 together (e.g., in contact with each other in a substantially flattened configuration) from lumen 2413, one or more slidable separators 2451 may be actuated within or extended from lumen 2413 between adjacent wires to cause the adjacent wires to separate into the position shown in FIG. 24. Slidable separator 2451 may be moved between at least two of the first, second, and third wire loops to separate the at least two of the first, second, and third wire loops.

As another example, first wire 2420, second wire 2430, and third wire 2440 may be heat set wires such as nitinol heat set wires that are conditioned to separate after being extended a predetermined distance from within lumen 2413. For example, first, second, and third wire loops 2420, 2430, and 2430 may be heat set wire loops configured to self separate upon extension to a predetermined distance from the distal end of the delivery shaft.

Figure 25:
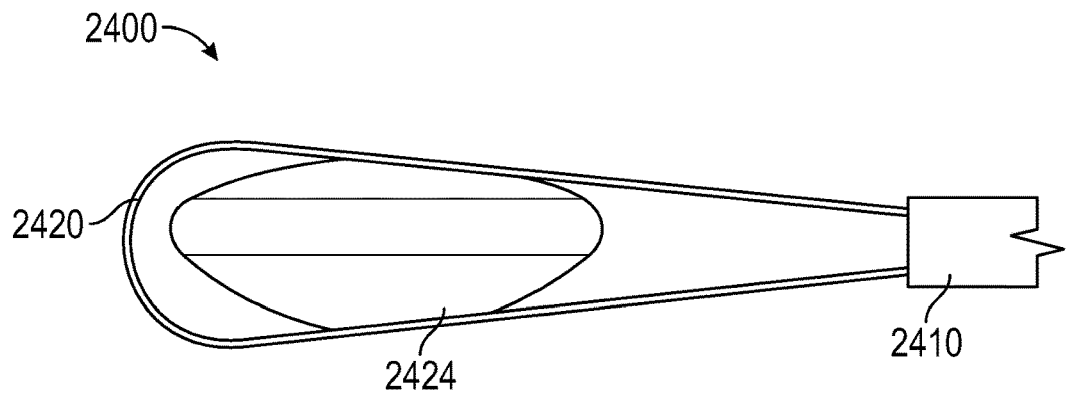
FIG. 25 shows a side view of a portion of the extraction device of FIG. 24, in accordance with one or more embodiments of the present disclosure.

In various implementations, first wire 2420, second wire 2430, and third wire 2440 may be extended from lumen 2413 at the same time or at different times (e.g., using a common extension mechanism or separate extension mechanisms to push the wires out of the lumen). FIG. 25 shows a side view of device 2400 with the wires extending around lens 2424. It should be appreciated that, although wires 2420, 2430, and 2440 have been referred to as a first wire, a second wire, and a third wire, this is merely for convenience and any of wires 2420, 2430, and 2440 can be referred to as a first wire, a second wire, or a third wire (or wire loop).

Figure 26:
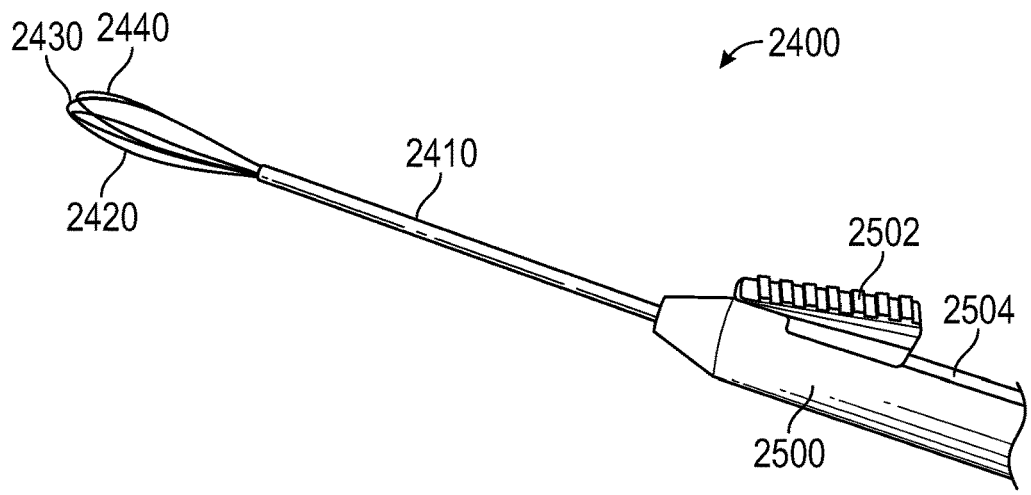
FIG. 26 shows a perspective view of a portion of the extraction device of FIG. 24 including a portion of a handle, in accordance with one or more embodiments of the present disclosure.

FIG. 26 shows a broader view of extraction device 2400 in which delivery shaft 2410 can be seen extending from a handle 2500 of device 2400. As shown, delivery shaft 2410 may be a substantially cylindrical tube attached at a proximal end to handle 2500. Handle 2500 may include a slider tab 2502, moveable by a user within a groove 2504, for deployment and retraction of wires 2420, 2430, and 2440 from delivery shaft 2410. In the configuration shown in FIG. 26, slider tab 2502 is in a forwardmost position and wires 2420, 2430, and 2440 are fully extended from shaft 2410. Slider tab 2502 may be coupled to wires 2420, 2430, and 2440 such that sliding slider tab 2502 away from shaft 2410 pulls wires 2420, 2430, and 2440 back into shaft 2410.

Although a single slider tab 2502 is shown in FIG. 26, it should be appreciated that two, three, or more sliders may be provided that slide in parallel within groove 2504 to move wires 2420, 2430, and 2440 and/or one or more separators or encapsulating bags individually or in groups. Actuation of sliders such as slider tab 2502 can control, together or separately, wires 2420, 2430, and 2440 and/or other components to deploy, retract, and/or rotate the wires and/or components attached thereto. According to some embodiments, the cross section of the slider mechanism within groove 2504 (and coupled to slider tab 2502) can be various shapes including circular (e.g., one tube within another which allows for rotational motion in addition to translational motion, see FIGS. 28 and 29 as examples).

One or more slider tabs such as slider tab 2502 may each be attached to one or both ends of the wire loops that form wires 2420, 2430, and 2440. For example, one end of each wire loop may be fixed within shaft 2410 and an opposing end attached to a slider tab so that extending the wire from lumen 2413 is performed by moving one side of the wire out of the lumen while the other side remains fixed. As another example, both ends of each wire loop may be attached to a slider tab so that extending the wire from lumen 2413 is performed by moving the entire loop. Wires 2420, 2430, and 2440 may be manipulated around lens 2424 together, prior to separation, or may be sequentially manipulated around lens 2424 after separation.

Figure 27:
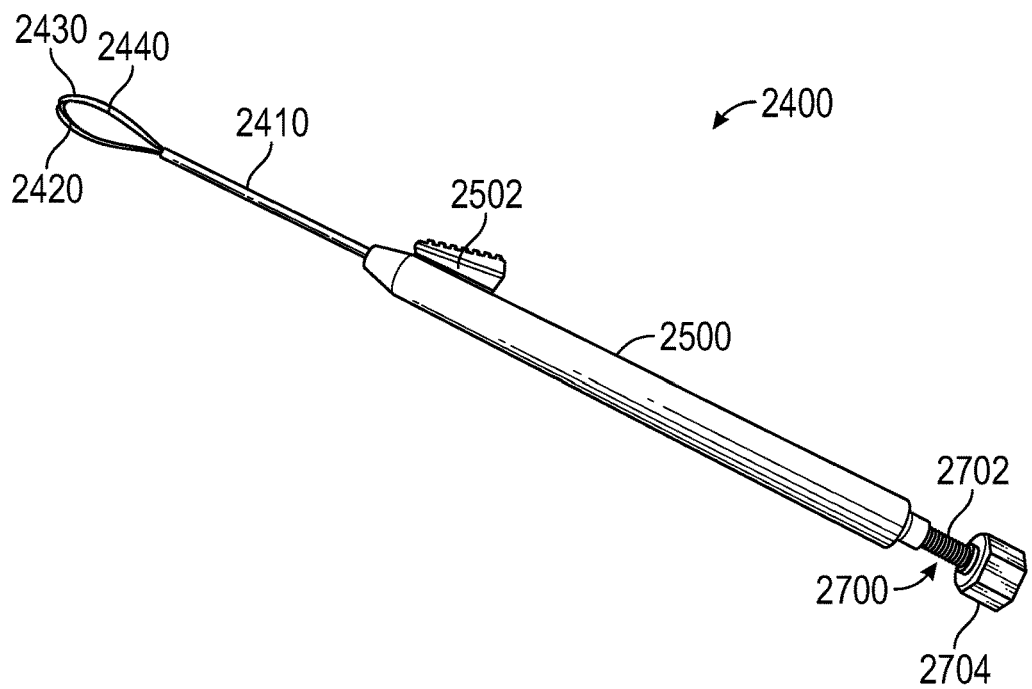
FIG. 27 shows a perspective the extraction device of FIG. 24, in accordance with one or more embodiments of the present disclosure.

FIG. 27 shows a perspective view of extraction device 2400 in which a control mechanism 2700 is provided at an end of handle 2500 opposite to the end at which delivery shaft 2410 is attached. In the example of FIG. 27, control mechanism 2700 includes a handle 2704 coupled to a threaded shaft 2702. In this implementation, handle 2704 may be rotated to move shaft 2410 (coupled to delivery shaft 2410 within handle 2500) to control the distance to which shaft 2410 extends from handle 2500. In some implementations, control mechanism 2700 may also allow for wires 2420, 2430, and 2440 to be removed from shaft 2410 and handle 2500 so that another tool such as a forceps can be inserted to remove cut portions of lens 2424 from the patient's eye via lumen 2413. In other implementations, a forceps may be included within delivery shaft 2410 and separately operable from wires 2420, 2430, and 2440. In still other implementations, forceps separate from extraction device 2400 may be used to extract lens pieces from the eye after the lens has been cut by wires 2420, 2430, and 2440. In other implementations, as discussed in further details hereinafter, additional elements such as a mesh or stent, and an encapsulation bag may be used in combination with wire loops 2420, 2430, and 2440 for extraction of lens pieces.

Figure 28:
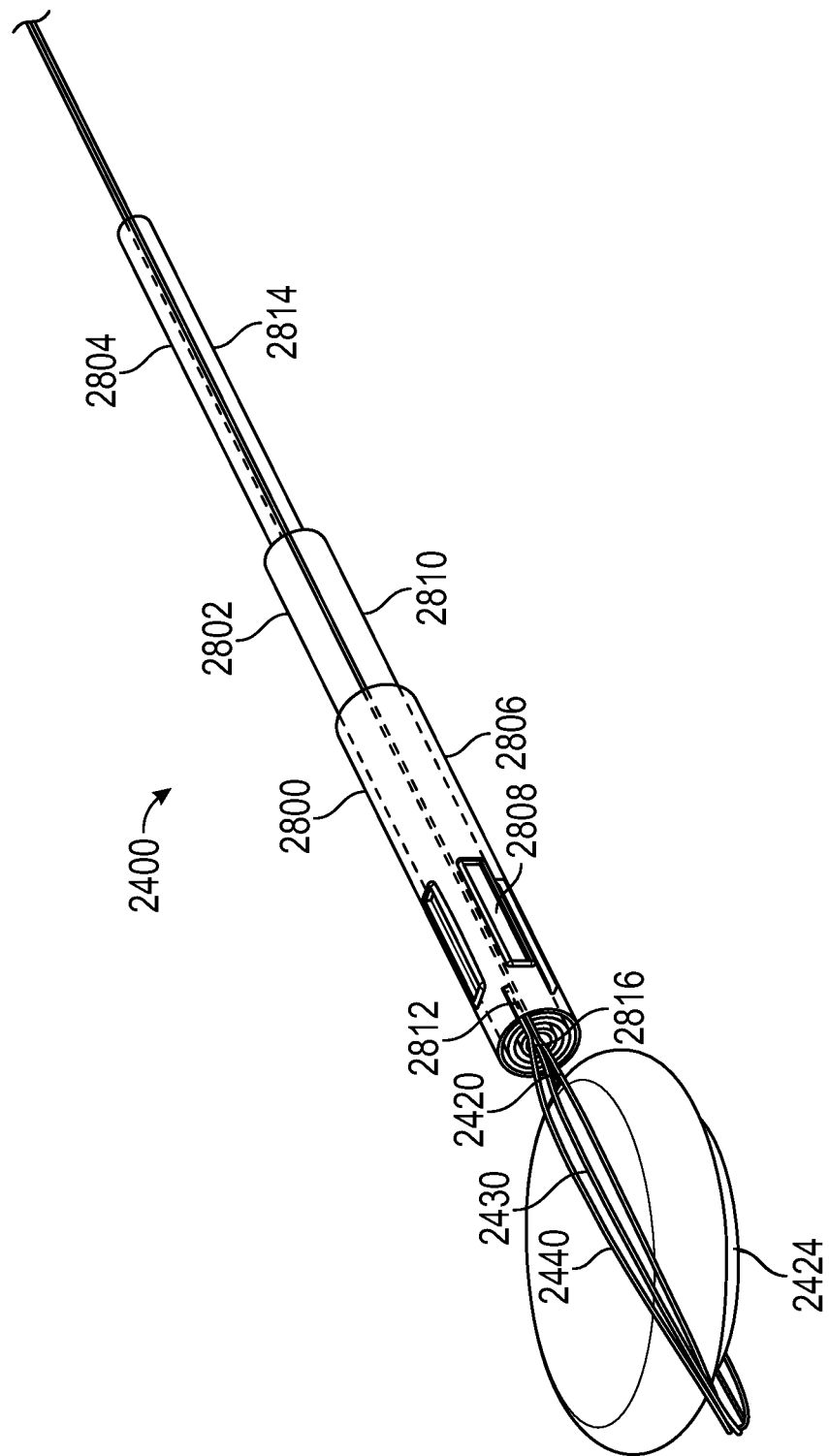
FIG. 28 shows a perspective view of a portion of an extraction device having three wire loops, in accordance with one or more embodiments of the present disclosure.
Figure 29:
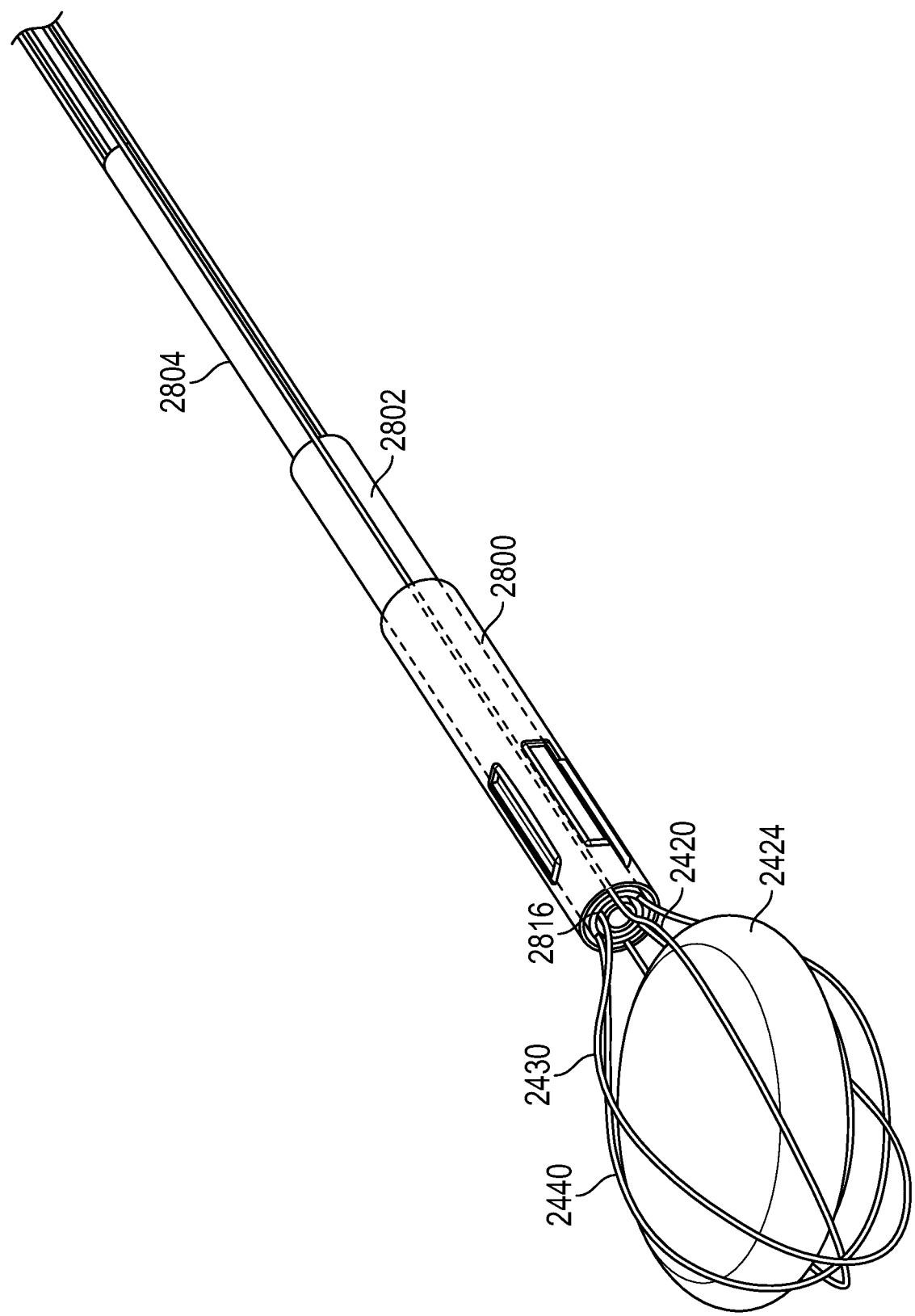
FIG. 29 shows a perspective view of the portion of the extraction device of FIG. 28 with the wire loops in a rotated configuration, in accordance with one or more embodiments of the present disclosure.

It should be appreciated that, although wires 2420, 2430, and 2440 are shown to be linearly separated in the implementation shown in FIGS. 24-27, this is merely illustrative and other implementations of wires 2420, 2430, and 2440 are possible. For example, FIGS. 28 and 29 show an implementation of extraction device 2400 in which wires 2420, 2430, and 2440 are rotatable relative to one another to surround and dissect lens 2424. FIGS. 28 and 29 show extraction device 2400 without delivery shaft 2410 for clarity.

As shown in FIG. 28, wires 2420, 2430, and 2440 may be extended around lens 2424 together in a flattened, substantially planar common loop. In the implementation of FIGS. 28 and 29, device 2400 is provided with wire-guide structures 2800, 2802, and 2804 (e.g., substantially cylindrical nested wire guide structures that are slidable and/or rotatable within delivery shaft 2410) configured to rotate wires 2420, 2430, and 2440 relative to each other to substantially surround lens 2424 (e.g., as in the configuration of FIG. 29).

Wire-guide structure 2800 may include a cylindrical main body 2806 (e.g., a portion of shaft 2410) and one or more protrusions 2808 (e.g., on the inner surface of shaft 2410 or on an outer surface of structure 2810) that guide the position of wire 2420. For example, a portion of wire 2420 may be positioned between two of protrusions 2808 and between the outer surface of cylindrical main body 2810 and the inner surface of delivery shaft 2410 so that the position of wire 2420 can be controlled by protrusions 2808.

Wire-guide structure 2802 may include a cylindrical main body 2810 that is at least partially nested within cylindrical main body 2806 of wire-guide structure 2800. Wire-guide structure 2802 may include a notch 2812 that allows wire 2440 to pass into an internal recess within wire-guide structure 2802 so that the rotational position of wire 2440 can be controlled by rotation of wire-guide structure 2802 (e.g., relative to wire-guide structures 2800 and 2804).

Wire-guide structure 2804 may include a cylindrical main body 2814 that is at least partially nested within cylindrical main body 2810 of wire-guide structure 2802. Wire-guide structure 2804 may include a notch 2816 that allows wire 2430 to pass into an internal recess within wire-guide structure 2804 so that the rotational position of wire 2430 can be controlled by rotation of wire-guide structure 2804 (e.g., relative to wire-guide structures 2800 and 2802).

In the implementations of FIGS. 28 and 29, first, second, and third wire loops 2420, 2440, and 2430 are configured to separate by a rotation of second and third wire loops 2440 and 2430 relative to first wire loop 2420. Wire-guide structures 2800, 2802, and 2804 may include first, second, and third nested wire-guide structures and configured to control a rotational position of first, second, and third wire loops 2420, 2440, and 2430. First wire-guide structure 2800 may include a cylindrical main body 2806 (e.g., a portion of shaft 2410) and a plurality of protrusions 2808 on an outer surface of the cylindrical main body 2810 or on an inner surface of shaft 2410. Second wire-guide structure 2802 may include a cylindrical main body 2810 at least partially nested within the cylindrical main body 2806 of first wire-guide structure 2800 (e.g., within shaft 2410) and at least one slot 2812 for the second wire loop 2440. Third wire-guide structure 2804 may include a cylindrical main body 2814 at least partially nested within the cylindrical main body 2810 of the second wire-guide structure and at least one slot 2816 for the third wire loop 2430. Second and third wire-guide structures 2802 and 2804 are rotatable relative to first wire-guide structure 2800. First, second, and third wire-guide structures 2800, 2802, and 2804 are slidable within delivery shaft 2410 for extension and retraction of the first, second, and third wire loops 2420, 2440, and 2430.

As shown in FIG. 29, after wires 2420, 2430, and 2440 have been deployed as a flat, somewhat circular, group of multiple wire loops (see, FIG. 28) wire-guide structures 2802 and 2804 may be rotated relative to wire-guide structure 2800 so that one or more wire loops 2420, 2430, and 2440 are rotated to surround the lens. Once in the configuration shown in FIG. 29, wires 2420, 2430, and 2440 can be retracted into delivery shaft 2410 to dissect the lens into multiple pieces as the wires are retracted. The dissected lens pieces can then be removed from the eye using forceps.

It should be appreciated that, although three wires are shown in the implementations of FIGS. 24-29, more or less than three wires may be provided that can be extended, separated, rotated, and/or retracted to divide lens 2424 into a desired number and size of pieces when the wires are retracted into lumen 2413. For example, FIGS. 30 and 31 show an implementation of extraction device 2400 in which two wires 2420 and 2430 are provided with interconnecting wires 3000 and 3002 that couple wires 2420 and 2430 at various locations around the respective wire loops. In the implementation of FIGS. 30 and 31, two relatively shorter interconnecting wires 3000 extend between wire loops 2420 and 2430 near a distal end of the loops and two relatively longer interconnecting wires 3002 extend between wire loops 2420 and 2430 nearer the distal end of delivery shaft 2410. By rotating wire loops 2420 and 2430 relative to one another, interconnecting wires 3000 and 3002 may be extended from a relaxed shape (as shown in FIG. 30) to a more straight and tensioned shape (as shown in FIG. 31), and thereby form a net-like structure which may surround lens 2424. First and second wire loops 2420 and 2430 in the implementation of FIGS. 30 and 31 are configured to separate by a rotation of first and/or second wire loops.

Wire-guide structures such as wire-guide structures 2800 and 2802 may be provided within delivery shaft 2410 to control the relative rotation of wire loops 2420 and 2430. Once in the configuration shown in FIG. 29, wires 2420 and 2430 and interconnecting wires 3000 and 3002 can be retracted into delivery shaft 2410 to dissect the lens into multiple pieces as the wires are retracted and wires 2420 and 2430 and interconnecting wires 3000 and 3002 cut through lens 2424. The dissected lens pieces can then be removed from the eye using forceps or other structures such as a wire mesh or stent and/or an encapsulation bag.

It should be appreciated that, although wires 2420 and 2430 are rotated in the implementation of FIGS. 30 and 31, it should be appreciated that one or more wire loops with interconnecting wires may be provided that separate to surround and dissect lens 2424. For example, FIGS. 32 and 33 show an implementation of extraction device 2400 in which two linearly separable wires 2420 and 2430 are provided with interconnecting wires 3000 that couple wires 2420 and 2430 at various locations around the respective wire loops. In the implementation of FIGS. 32 and 33, interconnecting wires 3000 of substantially equal length extend between wire loops 2420 and 2430 at various locations around the loops. By separating wire loops 2420 and 2430 after extension, interconnecting wires 3000 may be extended from a relaxed shape (as shown in FIG. 32) to a more straight and tensioned shape (as shown in FIG. 33), and thereby form a net-like structure which may surround lens 2424. First and second wire loops 2420 and 2430 in the configuration of FIGS. 31 and 32 may be configured to linearly separate to a separated configuration in which first wire loop 2420 is substantially parallel to second wire loop 2430 or in which wire loops 2420 and 2430 are separated by an increasing distance with increasing distance from shaft 2410 (see, e.g., FIG. 24).

Once in the configuration shown in FIG. 33, wires 2420 and 2430 and interconnecting wires 3000 can be retracted into delivery shaft 2410 to dissect the lens into multiple pieces as the wires are retracted and wires 2420 and 2430 and interconnecting wires 3000 cut through lens 2424. The dissected lens pieces can then be removed from the eye using forceps or other components such as a wire mesh and/or an encapsulation bag.

Figure 34:
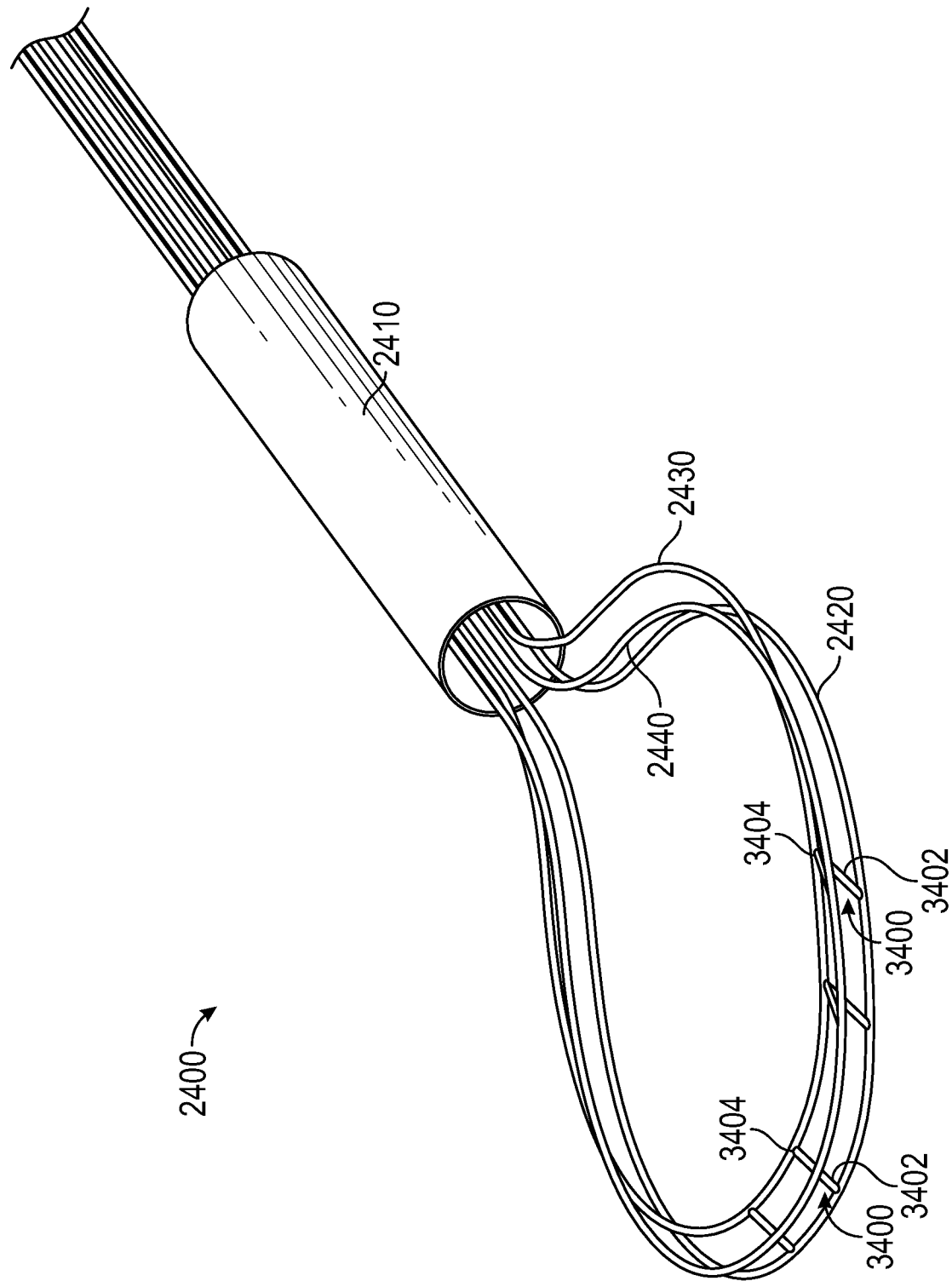
FIG. 34 shows a perspective view of a portion of another extraction device having three interconnected wire loops in a flattened configuration, in accordance with one or more embodiments of the present disclosure.
Figure 35:
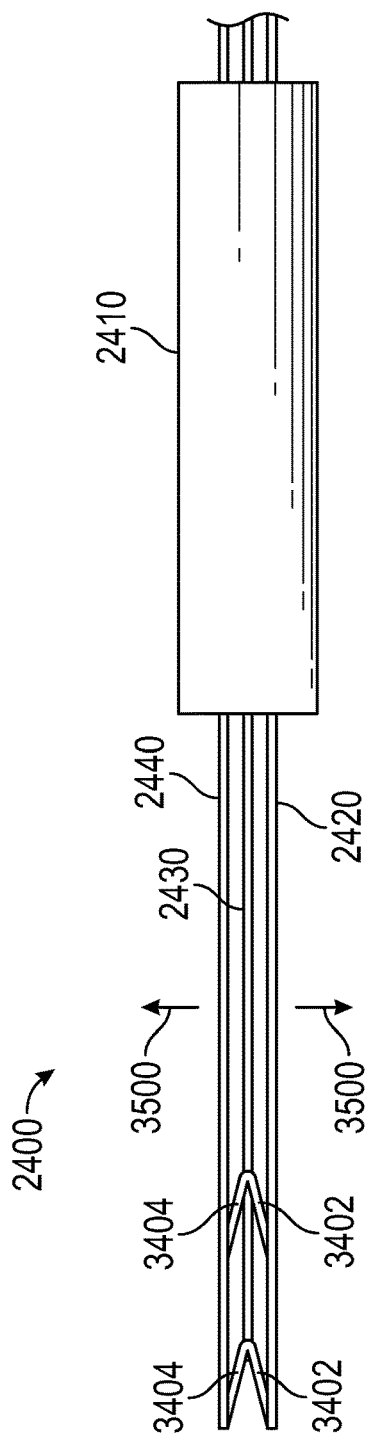
FIG. 35 shows a side view of the portion of the extraction device of FIG. 34, in accordance with one or more embodiments of the present disclosure.

As another example, FIGS. 34 and 35 show an implementation of extraction device 2400 in which three linearly separable wires 2420, 2430, and 2440 are provided with interconnecting wires 3400 that couple wires 2420, 2430, and 2440 at various locations around the respective wire loops. In the implementation of FIGS. 34 and 35, interconnecting wires 3400 of substantially equal length extend between wire loops 2420, 2430, and 2440 at various locations around the loops. Each interconnecting wire includes a first portion 3402 that extends from wire 2420 to wire 2430 and a second portion 3404 that extends from wire 2430 to wire 2440. In the example of FIGS. 34, and 35, portions 3402 and 3404 are located at the same location on the loops. However, portions 3402 and 3404 may be located at different locations around the loops in some implementations.

FIG. 35 shows a side view of the implementation of device 2400 of FIG. 34 in which it can be seen that, prior to separation of wire loops 2420, 2430, and 2440, middle loop 2430 is initially deployed from delivery shaft 2410 with a smaller diameter than the top and bottom loops 2420 and 2430, which causes the group of loops 2420, 2430, and 2440 to lay flat by tensioning the interconnecting wires 3400, and thus pulling the top and bottom loops 2420 and 2440 toward the middle loop 2430. Middle loop 2430 can then be pushed outward from delivery shaft 2410, such that the diameter of middle loop 2430 is increased to the same diameter as that of top and bottom loops 2420 and 2430, causing interconnecting wires 3400 to straighten, pushing wire loops 2420 and 2440 apart (e.g., as indicated by arrows 3500). In the flattened configuration of FIGS. 34 and 35, wire loops 2420, 2430, and 2440 can be moved to surround lens 2424. Wire loops 2420, 2430, and 2440 can then be expanded or separated by extending middle loop 2430 as described, such that interconnecting wires 3400 stand roughly perpendicular to the main loops 2420, 2430, and 2440. Wire loops 2420, 2430, and 2440 can then be retracted into delivery shaft 2410 to cut the lens into multiple pieces as wires 2420, 2430, and 2440 and interconnecting wires 3400 pass through the lens. The dissected lens pieces can then be removed from the eye using forceps or other components such as a wire mesh and/or an encapsulation bag.

Figure 36:
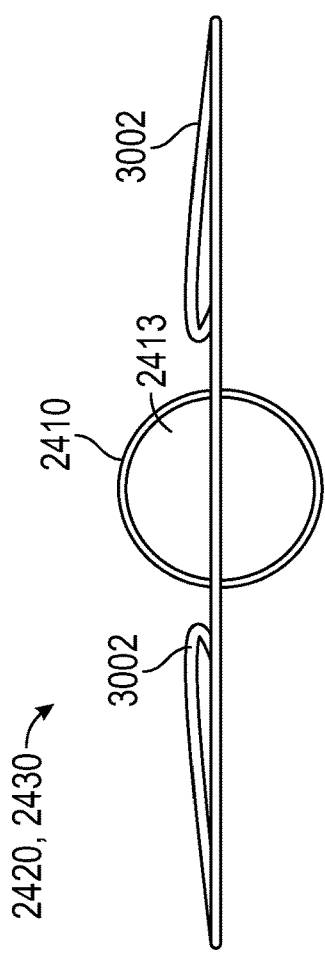
FIG. 36 shows a face-on view of the extraction device of FIG. 30, in accordance with one or more embodiments of the present disclosure.
Figure 37:
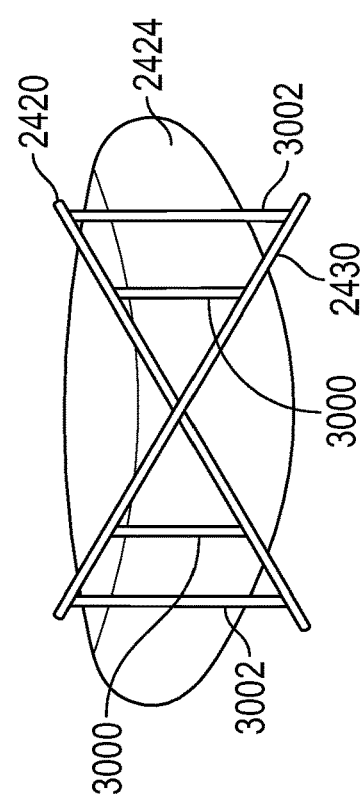
FIG. 37 shows a face-on view of the extraction device of FIG. 31, in accordance with one or more embodiments of the present disclosure.
Figure 38:
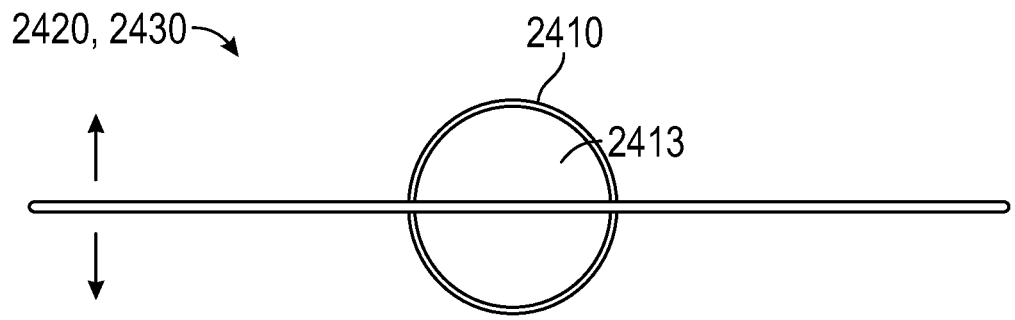
FIG. 38 shows a face-on view of the extraction device of FIG. 32, in accordance with one or more embodiments of the present disclosure.
Figure 39:
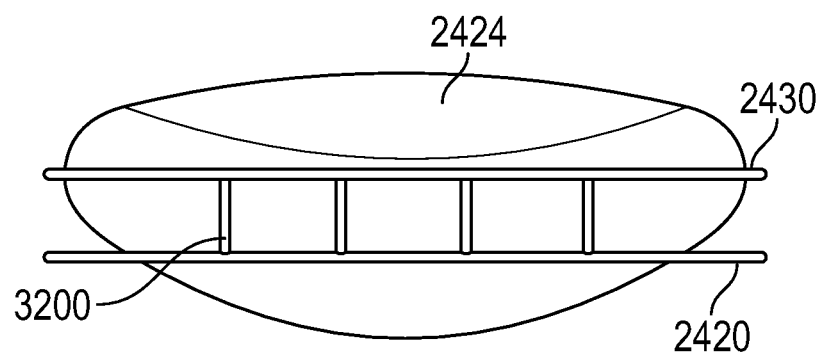
FIG. 39 shows a face-on view of the extraction device of FIG. 33, in accordance with one or more embodiments of the present disclosure.
Figure 40:
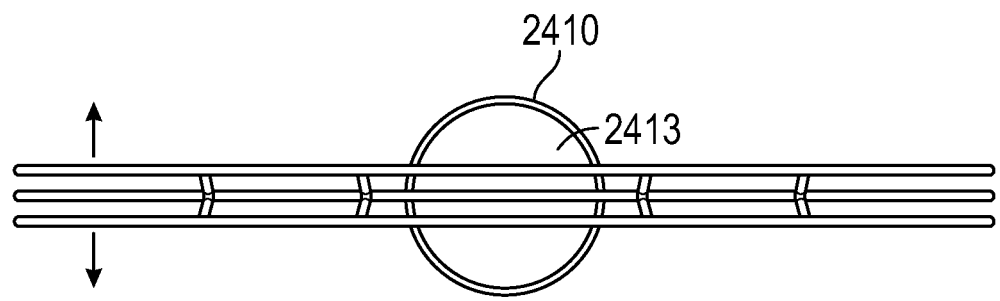
FIG. 40 shows a face-on view of the extraction device of FIG. 34, in accordance with one or more embodiments of the present disclosure.

For further clarity, face-on views of various implementations of extraction device 2400 (e.g. views facing the distalmost end of device 2400 along the central longitudinal axis of device 2400) are shown in FIGS. 36-40. More specifically, FIGS. 36 and 37 show face-on views of device 2400 in the implementation of FIGS. 30 and 31, FIGS. 38 and 39 show face-on views of device 2400 in the implementation of FIGS. 32 and 33, and FIG. 40 shows a face-on view of device 2400 in the implementation of FIGS. 34 and 35.

FIG. 36 shows a face-on view of device 2400 in the implementation and in the flattened configuration of FIG. 30, and shows how interconnecting wires 3002 may be curved slightly out of a plane defined by non-rotated wires 2420 and 2430 in the flattened configuration. FIG. 37 shows a face-on view of device 2400 in the implementation and rotated configuration of FIG. 31 and shows how interconnecting wires 3000 and 3002 may be straightened by rotated wires 2420 and 2430 that form an x-pattern in the rotated configuration.

FIG. 38 shows a face-on view of device 2400 in the implementation and flattened-configuration of FIG. 32. By separating wires 2420 and 2430 as indicated by arrows 3800, interconnecting wires 3200 may be straightened so that, as shown in FIG. 39, wires 2420 and 2430 may be substantially parallel with substantially perpendicular interconnecting wires 3200 interposed between.

FIG. 40 shows a face-on view of device 2400 in the implementation and flattened-configuration of FIGS. 34 and 35. By separating wires 2420, 2430, and 2440 (e.g., by extending middle wire 2430 as described above in connection with FIGS. 34 and 35) as indicated by arrows 4000, interconnecting wires 3400 may be straightened wires 2420, 2430, and 2440 may be substantially parallel with substantially perpendicular interconnecting wires 3400 interposed between.

The various implementations of extraction device 2400 described in connection with FIGS. 24-40 may be used to dissect lens 2424 into pieces (e.g., roughly equal sized pieces in the example of FIGS. 34, 35, and 40) that individually are sized to fit down delivery shaft 2410 for extraction. However, it should also be appreciated that extraction device 2400 may include one or more other components, in addition to one, two, three, or more cutting wires, such as a wire mesh or stent (e.g., to further dissect the cut lens pieces) and/or an encapsulation bag, extendible over the wires and/or the stent to encapsulate the cut/dissected lens for extraction through delivery shaft 2410. In some implementations, the wire mesh or stent can be used in place of, or in addition to, the cutting wires as described in connection with the implementations shown FIGS. 24-40.

Figure 41:
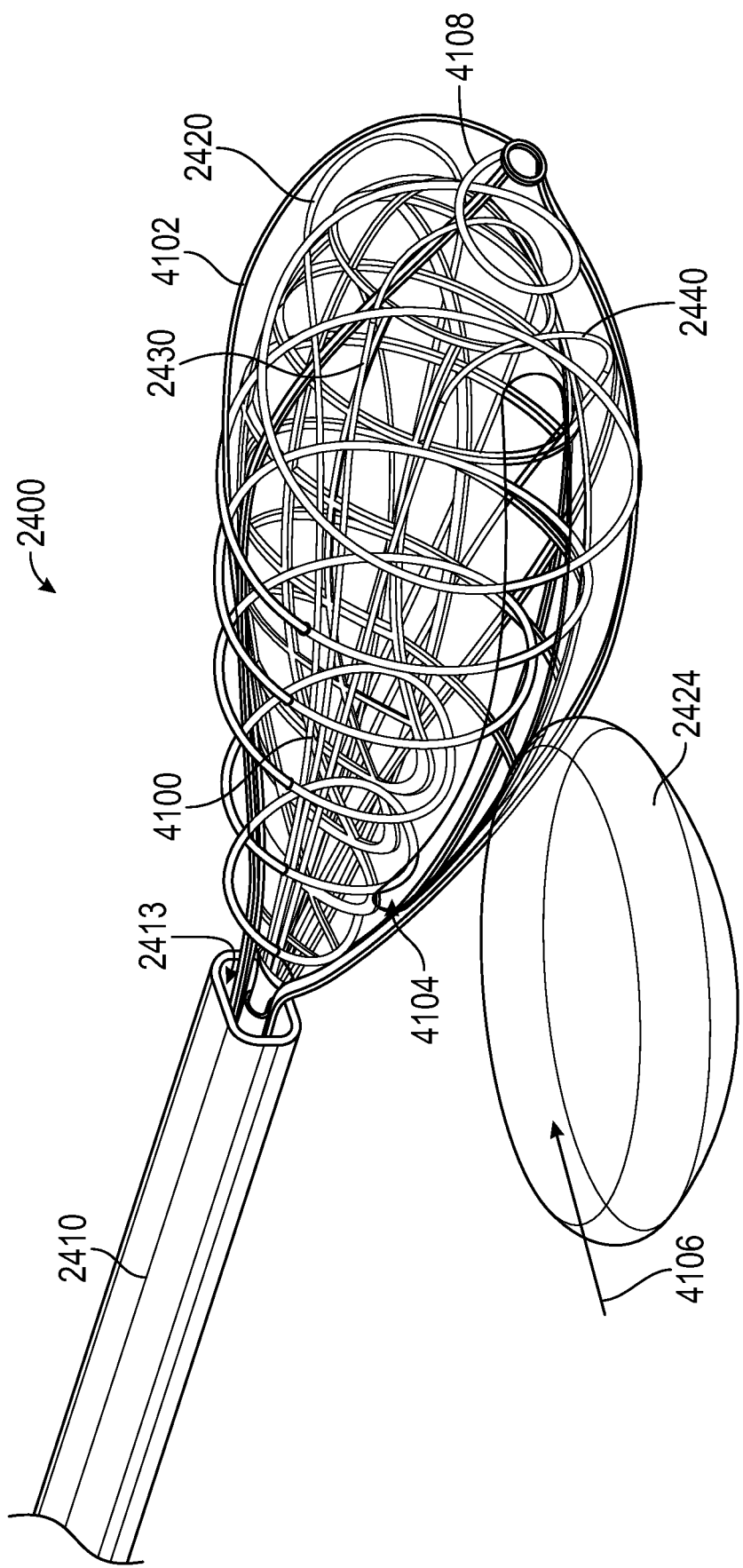
FIG. 41 shows a perspective view of a portion of an extraction device having wire loops, a stent, and an encapsulation bag, in accordance with one or more embodiments of the present disclosure.

FIG. 41 shows an exemplary implementation of extraction device 2400 in which a stent 4100 and an encapsulation bag 4102 are provided in addition to wire loops 2420, 2430, and 2440. As shown in FIG. 41, after extension of wires 2420, 2430, and 2440, a wire mesh or stent such as stent 4100 may be extended around wire loops 2420, 2430, and 2440. Encapsulation bag 4102 may be extended around stent 4100 (e.g., as described above in connection with various implementations). An opening 4104 may be provided (e.g., an opening formed by coaligned openings in bag 4102 and stent 4100) through which lens 2424 can be inserted into a cavity formed and defined by stent 4100 and bag 4102. For example, by moving extraction device 2400 toward lens 2424 so that lens 2424 (while remaining substantially stationary within the patient's eye) is moved in direction 4106 relative to device 2400, lens 2424 can be inserted through opening 4104 into the cavity and substantially surrounded by wires 2420, 2430, and 2440, stent 4100, and bag 4102.

Figure 42:
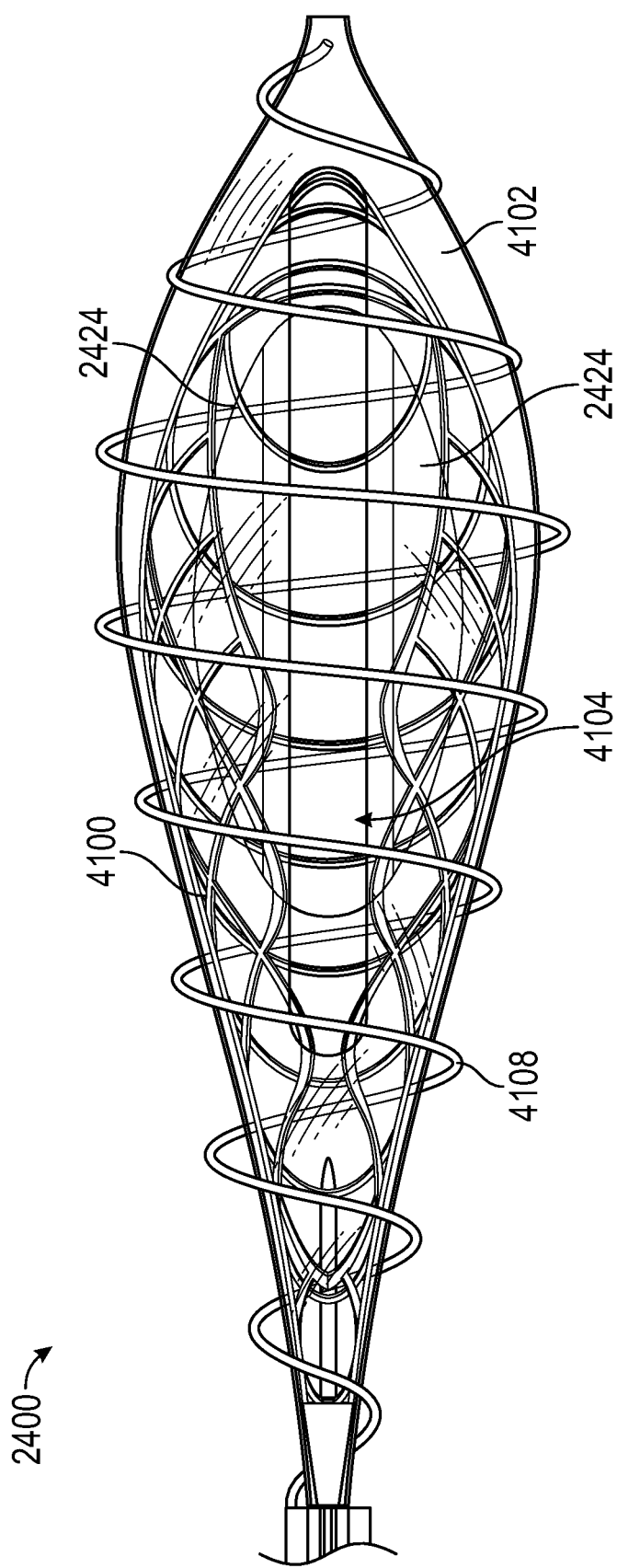
FIG. 42 shows a side view of the extraction device of FIG. 41, in accordance with one or more embodiments of the present disclosure.

FIG. 42 shows a side view of extraction device 2400 in the configuration of FIG. 41 after insertion of lens 2424 into the cavity formed by wires 2420, 2430, and 2440, stent 4100, and bag 4102. Following insertion of the lens into the cavity formed by wires 2420, 2430, and 2440, stent 4100, and bag 4102, wires 2420, 2430, and 2440 may be retracted into lumen 2413 to cut lens 2424 (e.g., as described above in connection with FIGS. 24 and 25), and then stent 4100 may be retracted to further cut and/or cube the lens into smaller, softer pieces.

Device 2400 may also include a spiral compaction wire 4108 wrapped in spiral windings around bag 4102. After wires 2420, 2430, and 2440 and stent 4100 have been retracted to cut and cube lens 2424 within bag 4102, spiral compaction wire 4108 may be retracted to further compact the pieces of lens 2424 within encapsulation bag 4102 for extraction from the eye (e.g., by extracting bag 4102 and wire 4108 into lumen 2413 or by withdrawing device 2400 from the eye without extracting bag 4102 back into lumen 2413).

Figure 43:
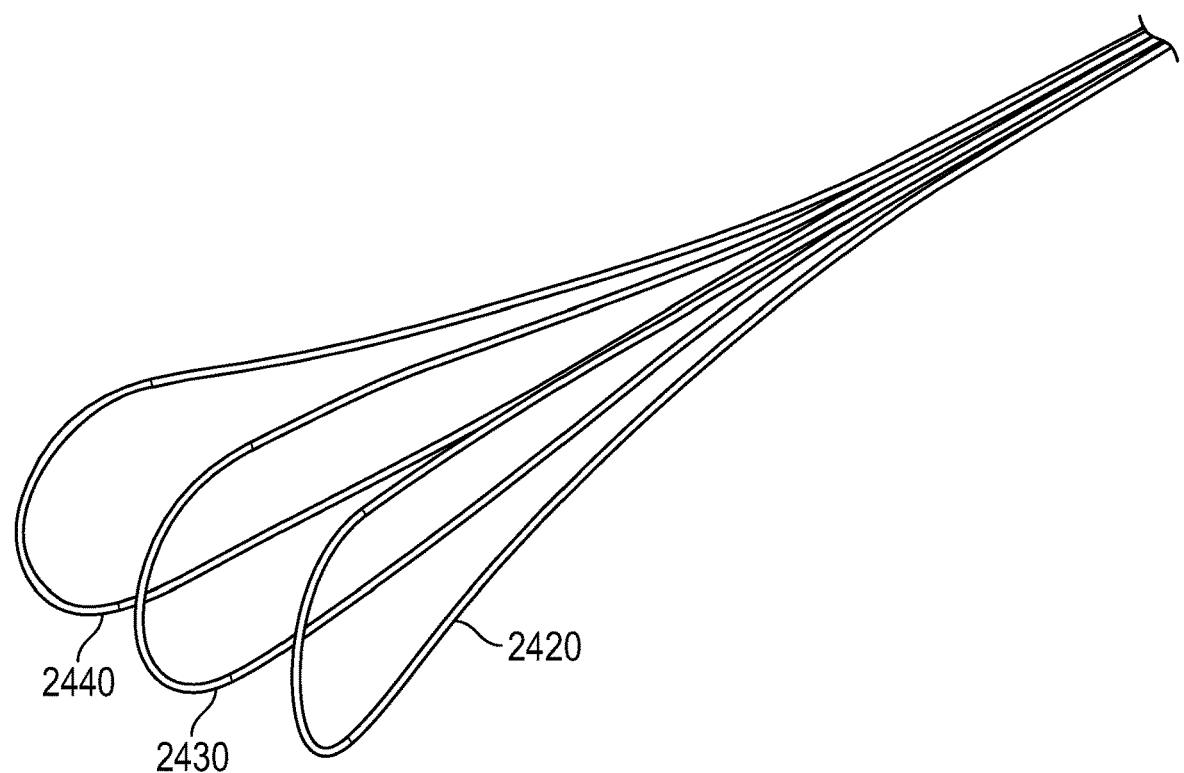
FIG. 43 shows a perspective view of the wire loops of the extraction device of FIG. 41, in accordance with one or more embodiments of the present disclosure.
Figure 44:
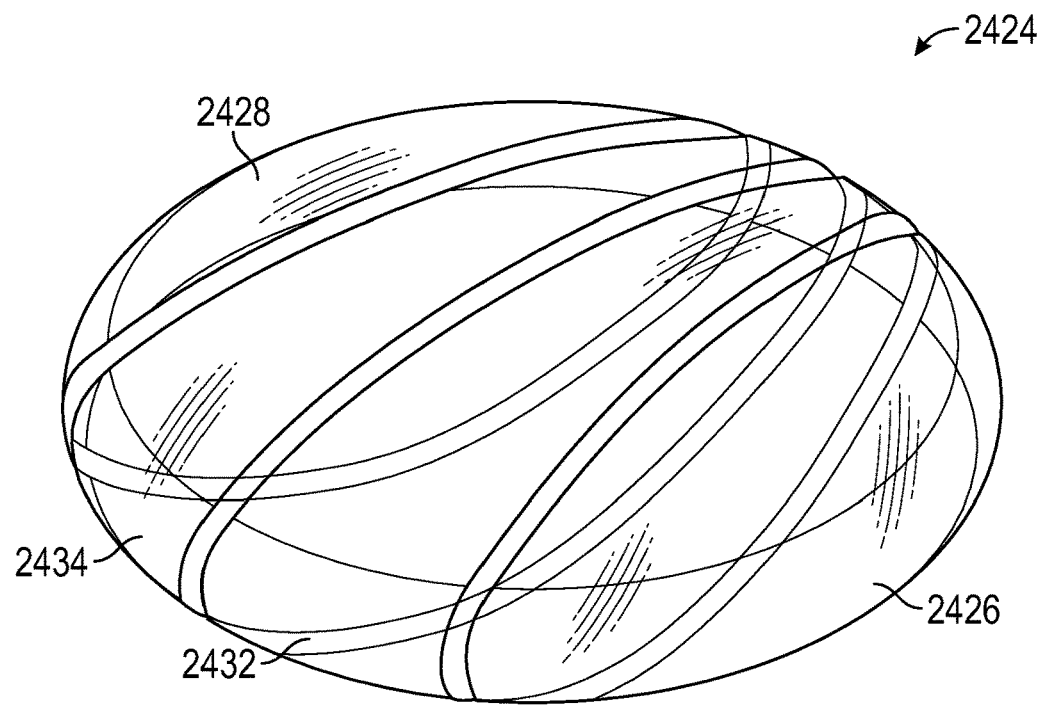
FIG. 44 shows a perspective view of a lens cut by the wire loops of FIG. 43, in accordance with one or more embodiments of the present disclosure.

FIG. 43 shows wires 2420, 2430, and 2440 of device 2400 of FIG. 41 with other components of device 2400 removed for clarity. Wires 2420, 2430, and 2440 may be formed, for example, from nitinol, may have a cross-sectional width of, for example, 0.004", and may be extended and/or withdrawn from lumen 2413 as described above in connection with, for example FIGS. 24-27. FIG. 44 shows an illustrative example of a lens 2424 that has been cut into pieces 2426, 2428, 2432, and 2434 by retraction of wires 2420, 2430, and 2440 through lens 2424 into lumen 2413.

Figure 45:
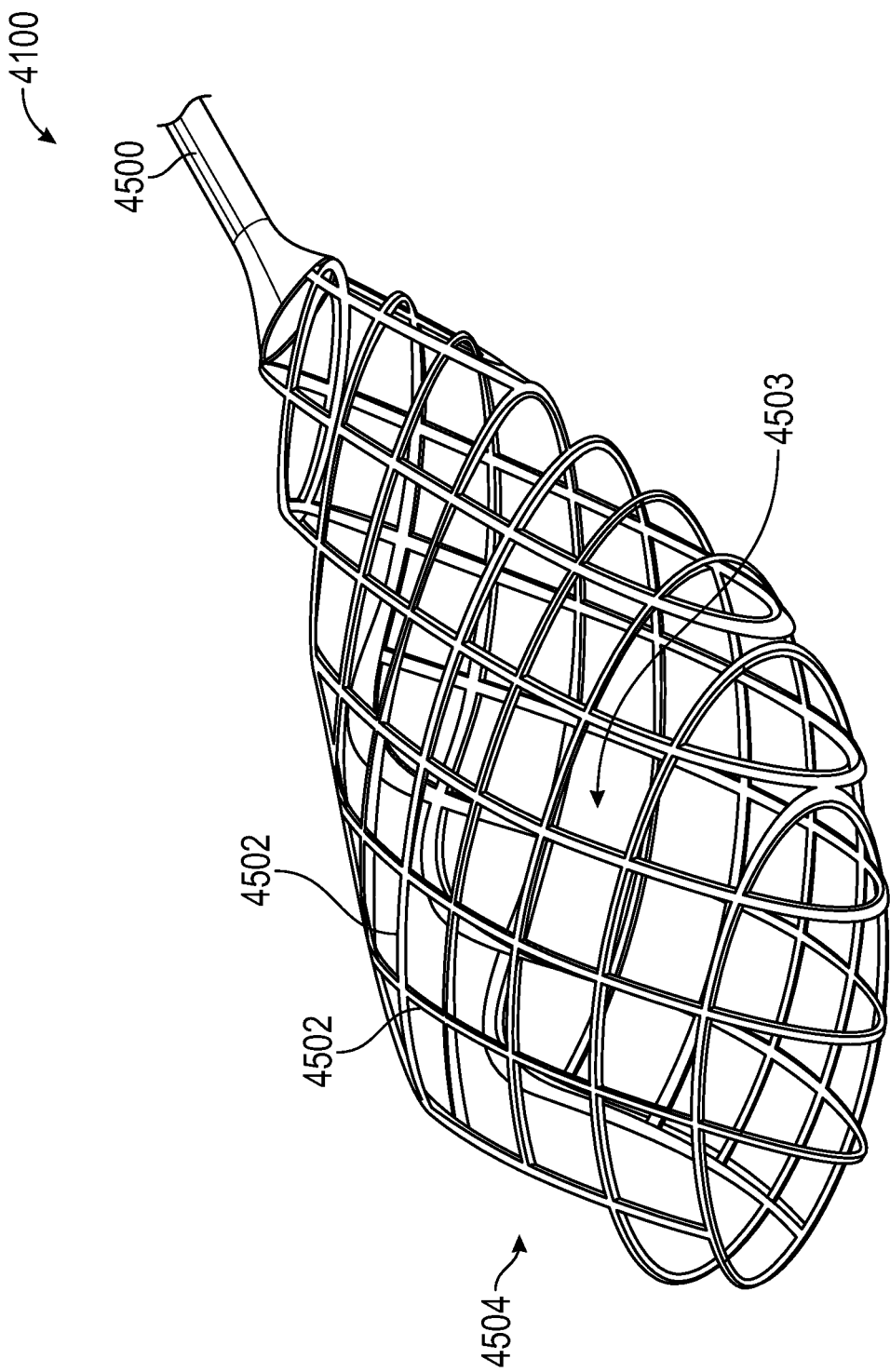
FIG. 45 shows a perspective view of the stent of the extraction device of FIG. 41, in accordance with one or more embodiments of the present disclosure.
Figure 46:
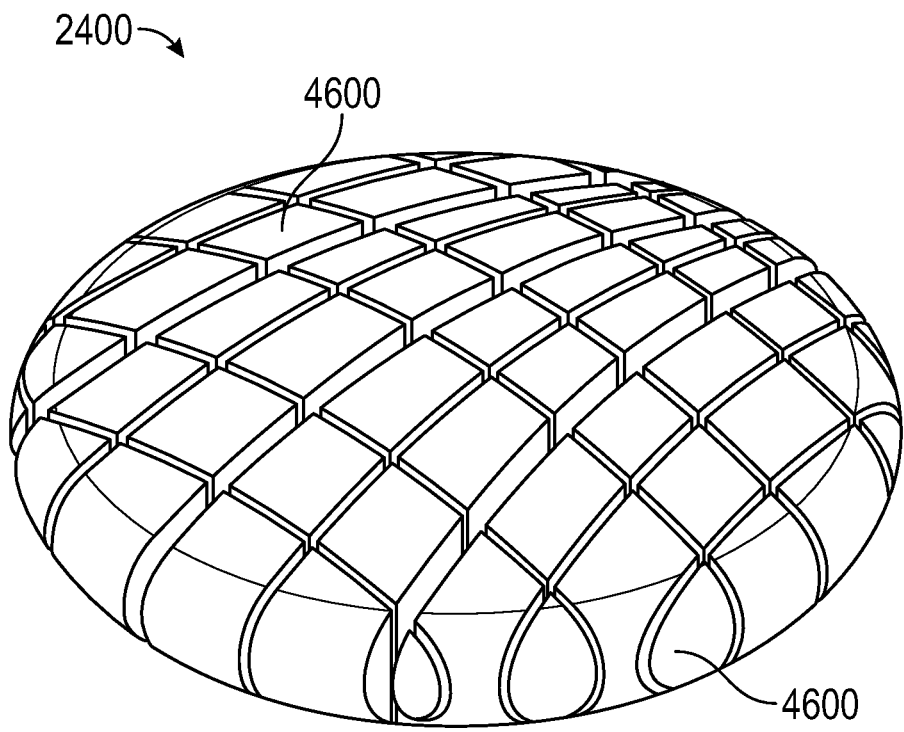
FIG. 46 shows a perspective view of a lens cubed by the stent of FIG. 45, in accordance with one or more embodiments of the present disclosure.

FIG. 45 shows stent 4100 of device 2400 of FIG. 41 with other components of device 2400 removed for clarity. Stent 4100 may include a plurality of intersecting wire elements 4502 extending from a shaft 4500 that form and define a cavity 4503. Stent 4100 may be formed from a wire mesh braid or may be a laser-cut structure. Intersecting wire elements 4502 may be formed from metal and/or plastic and may have a cross-sectional width of between 0.001" and 0.005" (e.g., 0.003 inches) in some implementations. Intersecting wire elements 4502 may be configured to return to a natural expanded shape, as shown in FIG. 45, when extended from within lumen 2413 (e.g., from a compressed shape within lumen 2413) to form a cavity 4503, accessible by lens 2424 through an opening 4504. FIG. 46 shows an illustrative example of a lens 2424 in which pieces 2426, 2428, 2432, and 2434 have been cut/cubed into smaller pieces 4600 by retraction and resulting compression of stent 4100 through lens 2424 into lumen 2413.

Figure 47:
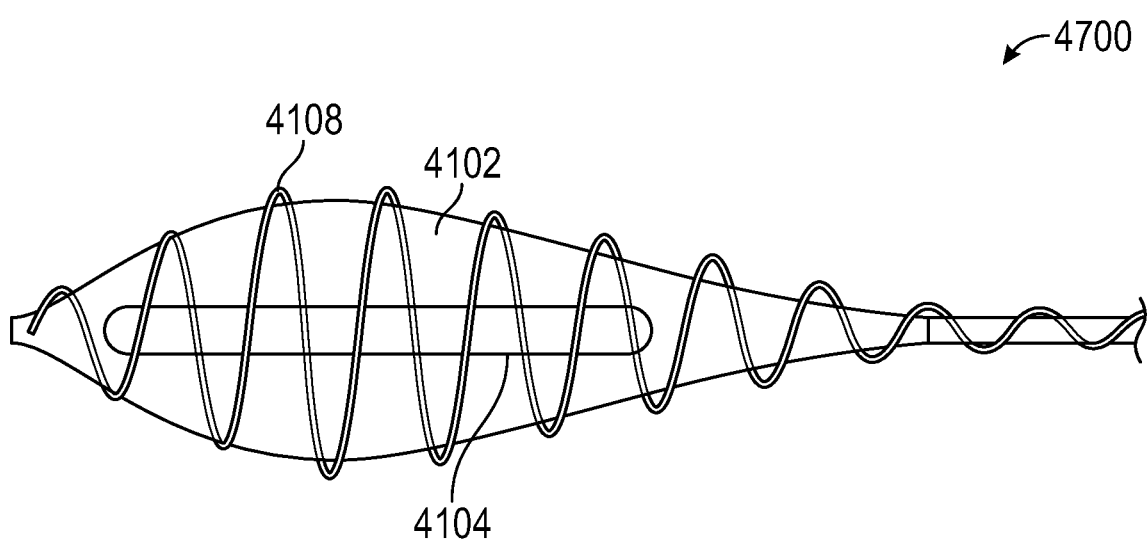
FIG. 47 shows a perspective view of the encapsulation bag of the extraction device of FIG. 41, in accordance with one or more embodiments of the present disclosure.
Figure 48:
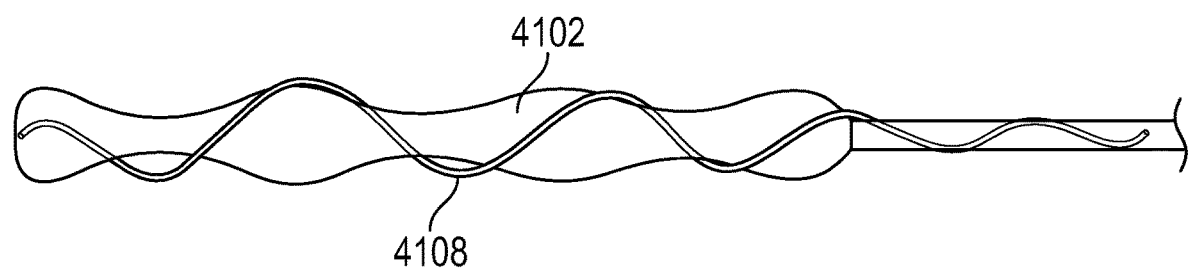
FIG. 48 shows a perspective view of the encapsulation bag of the extraction device of FIG. 41 in a collapsed configuration, in accordance with one or more embodiments of the present disclosure.

FIG. 47 shows encapsulation bag 4102 and spiral compaction wire 4108 of device 2400 of FIG. 41 with other components of device 2400 removed for clarity. Encapsulation bag 4102 may be formed from an elastic material such as an expanded polytetrafluoroethylene (ePTFE) material. Encapsulation bag 4102 may include an opening 4704. Opening 4704 may be configured to be coaligned with opening 4504 of stent 4100, when stent 4100 and bag 4102 are in an extended configuration, to form opening 4104 of FIG. 41. Spiral compaction wire 4108 may be formed from a metal such as nitinol and may have a cross-sectional width of, for example, between, 0.001" and 0.005" (e.g., 0.003"). Spiral compaction wire 4108 may be extracted to radially compress encapsulation bag 4102, in a circular motion, into the configuration of FIG. 48, to collect and compress pieces 4600 of lens 2424 for extraction from the eye. Encapsulation bag 4102 can be removed from the patient's eye by retraction into lumen 2413 or by extraction of the entire device 2400 from the eye without pulling bag 4102 back into lumen 2413.

Figure 49:
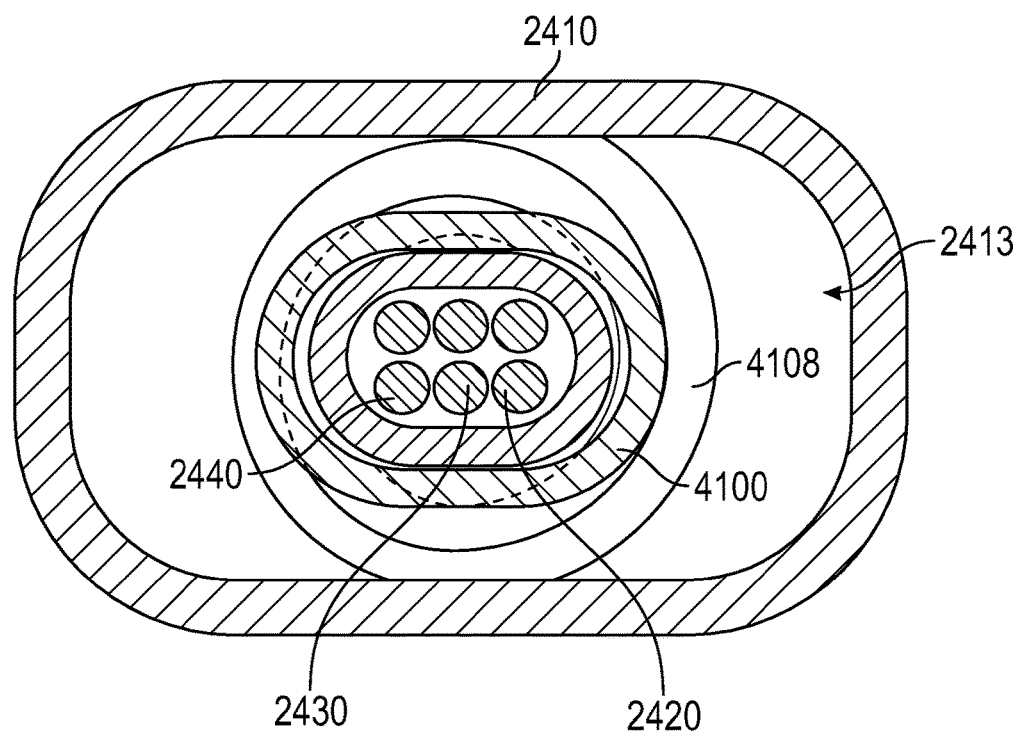
FIG. 49 shows a cross-sectional view of the extraction device of FIG. 41, in accordance with one or more embodiments of the present disclosure.

FIG. 49 shows a cross-sectional view of delivery shaft 2410 with wires 2420, 2430, and 2440, stent 4100, and spiral compaction wire 4108 disposed within lumen 2413 (e.g., prior to extension from, or after retraction into lumen 2413). For clarity, encapsulation bag 4102 is not shown in FIG. 49, but would occupy the empty space visible in lumen 2413. As shown in FIG. 49, in some implementations delivery shaft 2410 may have a cross-sectional shape other than a circular cross-sectional shape (e.g., a rectangular cross-sectional shape with rounded corners). After retraction of wires 2420, 2430, and 2440 and stent 4100 through lens 2424 into lumen 2413, some pieces of lens 2424 may also occupy some of the space within lumen 2413 (e.g., by being pulled into delivery shaft 2410 during the retraction).

Figure 50:
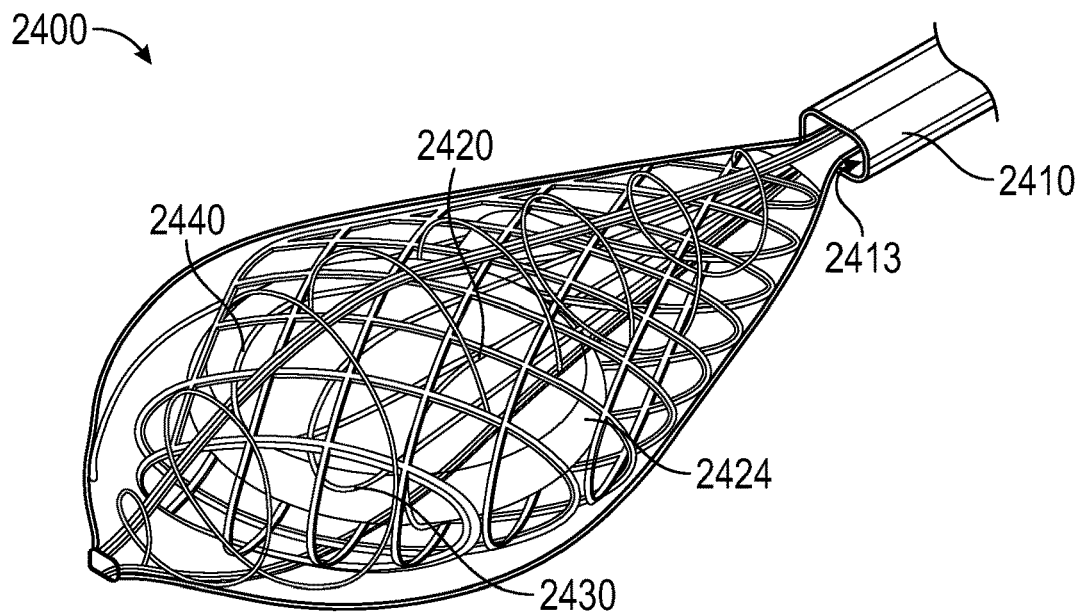
FIG. 50 shows a perspective view of the extraction device of FIG. 41 during cutting of the lens by the wire loops, in accordance with one or more embodiments of the present disclosure.
Figure 51:
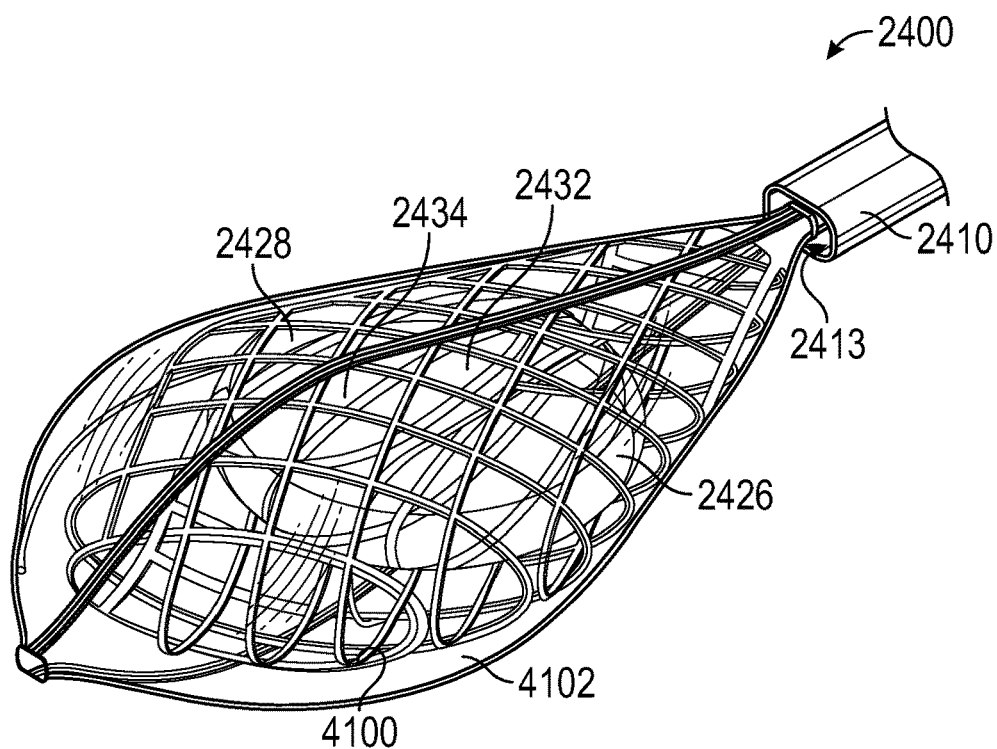
FIG. 51 shows a perspective view of the extraction device of FIG. 41 after cutting of the lens by the wire loops, in accordance with one or more embodiments of the present disclosure.
Figure 52:
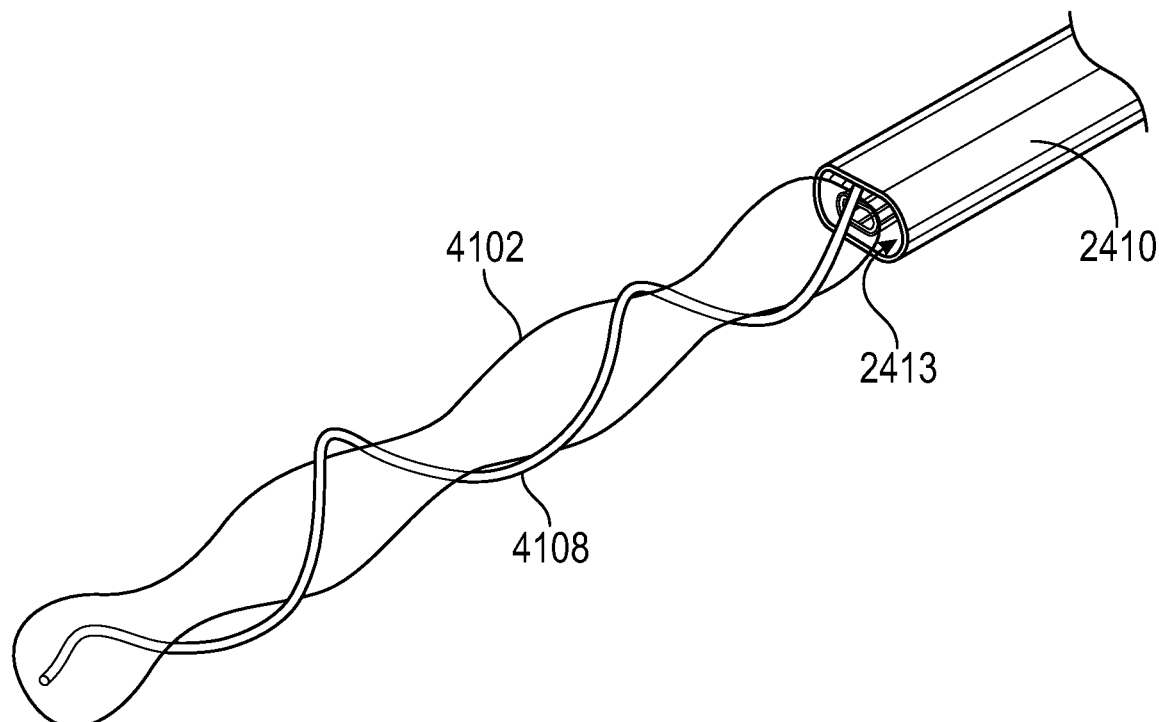
FIG. 52 shows a perspective view of the extraction device of FIG. 41 after cubing of the lens by the stent and after collapsing of the encapsulation bag, in accordance with one or more embodiments of the present disclosure.

FIGS. 50-52 illustrate extraction device 2400 of FIG. 41 at various stages during cataract extraction operations. In the example of FIG. 50, lens 2424 is disposed within the cavity formed by wires 2420, 2430, and 2440, stent 4100, and encapsulation bag 4102 and wires 2420, 2430, and 2440 have been partially retracted into lumen 2413 and have partially passed into lens 2424. In the example of FIG. 51, lens 2424 has been cut into pieces 2426, 2428, 2432, and 2434 and wires 2420, 2430, and 2440 have been retracted into lumen 2413. Stent 4100 and bag 4102 remain surrounding lens 2424. In the example of FIG. 52, stent 4100 has been retracted into lumen 2413 and spiral compaction wire has been retracted to radially compress bag 4102 to encapsulate, capture, and contain any remaining pieces of lens 2424. In the configuration of FIG. 52, bag 4102 can be retracted into lumen 2413 or device 2400 can be entirely removed from the patient's eye without retracting bag 4102.

One or more features of any one of the extraction devices 100, 200, 300, 400, 600, 705, 805, 905, 1000, 1100, 1200, 1300, 1400, 1500, 1600, 1700, 1800, and 2400 can be combined with one or more features of any other one of the extraction devices 100, 200, 300, 400, 600, 705, 805, 905, 1000, 1100, 1200, 1300, 1400, 1500, 1600, 1700, 1800, and 2400. One or more features of any one of the covers and/or bags discussed herein can apply to any other one of the covers and/or bags and the deployment mechanisms such as guides associated therewith.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. An extraction device, comprising:
a delivery shaft having a lumen and a distal end;
a first wire forming a first arc and being positionable distal to the distal end of the delivery shaft while ends of the first arc are at a distalmost end of the delivery shaft; and
a second wire forming a second arc and being positionable distal to the distal end of the delivery shaft while ends of the second arc are at the distalmost end of the delivery shaft,
wherein a distalmost extent of the first wire is distal to a distalmost extent of the second wire, wherein the first wire and the second wire are separately retractable relative to the delivery shaft.

Concept 2. The extraction device of Concept 1 or any other Concept, further comprising:
a first guide and a second guide moveable along the first wire toward the distalmost extent of the first wire from a first position to a second position more distal than the first position; and
a cover attached to the first guide and the second guide, wherein, while in the second position, the cover encompasses an outer cross-sectional dimension of each of (i) the first wire and (ii) the second wire.

Concept 3. The extraction device of Concept 1 or any other Concept, further comprising:
a first ring extending about the first wire and the second wire;
a first cover extending from the first ring to the delivery shaft;
a second ring extending about the first wire and the second wire; and
a second cover extending from the second ring to the distalmost end of the first wire.

Concept 4. An extraction device, comprising:
a delivery shaft having a lumen and a distal end;
a dissection tool distal to the distal end of the delivery shaft;
a first capture portion positionable on a first side of an axis of the delivery shaft and comprising a first cover; and
a second capture portion positionable on a second side of the axis, opposite the first side, and comprising a second cover,
wherein the first capture portion and the second capture portion are configured to move toward the axis upon actuation and define an enclosed space between the first cover and the second cover.

Concept 5. An extraction device, comprising:
a delivery shaft having a distal end;
an irrigation port at the distal end;
a loop having a fluid permeable cover; and
a blade being moveable from a retracted position to an actuated position across at least a portion of the loop.

Concept 6. An extraction device, comprising:
a delivery shaft having:
an inner cylindrical shaft structure with a distal end; and
an outer cylindrical shaft structure having a distal end with a sharp cutting edge, wherein the sharp cutting edge of the outer cylindrical shaft structure is deployable beyond the distal end of the inner cylindrical shaft structure.

Concept 7. An extraction device, comprising:
a delivery shaft having a distal end with a sharp cutting edge; and
a gripping apparatus that is extendible from within a lumen of the delivery shaft and operable to grip and pull tissue against the sharp cutting edge.

Concept 8. An extraction device, comprising:
a delivery shaft having a distal end; and
an excision member that is extendible from within a lumen of the delivery shaft, wherein the excision member comprises a control shaft and a plurality of layered cutting and encapsulation leaves.

Concept 9. The extraction device of Concept 8 or any other Concept, wherein, the layered cutting and encapsulation leaves are configured to be reticulated relative to each other about an axis to create an enclosure for a lens or portion thereof.

Concept 10. An extraction device, comprising:
a delivery shaft having a distal end;
a first frame extendible from the distal end of the delivery shaft and having a flexible bag structure attached thereto; and
a second frame extendible from the distal end of the delivery shaft and having a lid structure attached thereto, wherein, in an extended configuration for the first frame and the second frame, the flexible bag structure and the lid structure are configured to define and enclose a cavity within which at least a portion of a lens of a patient's eye is encapsulated.

Concept 11. The extraction device of Concept 10 or any other Concept, wherein the second frame is configured, upon extension from the distal end of the delivery shaft, to transect the encapsulated at least the portion of the lens of the patient's eye.

Concept 12. The extraction device of Concept 11 or any other Concept, further comprising one or more additional frames, each extendible from the distal end of the delivery shaft with the first frame and retractable from within the cavity into the distal end of the delivery shaft to dissect the at least the portion of the lens of the patient's eye held therein.

Concept 13. A method, comprising:
extending a first frame, having an attached flexible bag structure, and a second frame into an eye of a patient such that the flexible bag structure at least partially surrounds at least a portion of a lens of the eye of the patient;
extending a third frame having an attached lid structure along the first frame to encapsulate the at least the portion of the lens between the flexible bag structure and the lid structure; and
withdrawing the second frame to transect the encapsulated at least the portion of the lens.

Concept 14. The method of Concept 13 or any other Concept, further comprising, prior to extending the first frame with the attached flexible bag structure and the second frame into the eye of the patient, performing a hydrodissection and/or a hydrodelineation procedure to change a position of the lens from being entirely within a natural capsular bag of the lens to being partially or completely displaced from the natural capsular bag.

Concept 15. The method of Concept 13 or any other Concept, further comprising withdrawing the first frame and the third frame from the eye of the patient to remove the transected, encapsulated at least the portion of the lens from the eye.

Concept 16. An extraction device, comprising:
a delivery shaft having a distal end;
a first frame extendible from the distal end of the delivery shaft and having a flexible bag structure attached thereto, wherein the flexible bag structure includes a plurality of openings; and
a second frame extendible from the distal end of the delivery shaft and having a lid structure attached thereto, wherein, in an extended configuration for the first frame and the second frame, the flexible bag structure and the lid structure are configured to secure at least a portion of a lens of a patient's eye therebetween.

Concept 17. The extraction device of Concept 16 or any other Concept, wherein, upon withdrawal of the first frame and the second frame into the distal end of the delivery shaft while the at least the portion of the lens is secured between the flexible bag structure and the lid structure, the flexible bag structure is configured to strain the at least the portion of the lens through the plurality of openings.

Concept 18. The extraction device of Concept 16 or any other Concept, wherein the second frame is configured, upon extension from the distal end of the delivery shaft, to transect the lens.

Concept 19. The extraction device of Concept 16 or any other Concept, further comprising one or more additional frames, each extendible from the distal end of the delivery shaft with the first frame and retractable into the distal end of the delivery shaft to dissect the at least the portion of the lens of the patient's eye held therein.

Concept 20. The extraction device of Concept 16 or any other Concept, wherein the lid structure comprises a plurality of openings.

Concept 21. A method, comprising:
extending a first frame having an attached flexible bag structure with a plurality of openings from a distal end of a delivery shaft into an anterior chamber of an eye of a patient such that the flexible bag structure at least partially surrounds at least a portion of a lens of the eye of the patient;
extending a second frame having an attached lid structure along the first frame to secure the at least the portion of the lens between the flexible bag structure and the lid structure; and
withdrawing the first and second frames into the distal end of the delivery shaft to strain the at least the portion of the lens through the plurality of openings in the flexible bag structure into the anterior chamber.

Concept 22. The method of Concept 21 or any other Concept, further comprising:
extending a third frame into the eye of the patient together with the first frame; and
prior to withdrawing the first and second frames, withdrawing the third frame to transect the secured at least the portion of the lens.

Concept 23. The method of Concept 22 or any other Concept, further comprising suctioning the strained at least the portion of the lens from the anterior chamber.

Concept 24. An extraction device, comprising:
a delivery shaft having a lumen and a distal end; and
first, second, and third wire loops extendible from within the lumen at the distal end, wherein the first, second, and third wire loops are configured to separate upon extension from within the lumen to at least partially surround a lens of a patient's eye, and wherein the separated first, second, and third wire loops are configured to be withdrawn into the lumen to pass through and dissect the lens.

Concept 25. The extraction device of Concept 24 or any other Concept, further comprising:
a handle, wherein a proximal end of the delivery shaft is attached to the handle; and
a slider tab in the handle and attached to the first, second, and third wire loops, wherein the slider tab is slidable to extend and withdraw the first, second, and third wire loops.

Concept 26. The extraction device of Concept 24 or any other Concept, wherein the second wire loop comprises a middle wire loop disposed between the first and third loops, and wherein the first, second, and third wire loops are configured to linearly separate in a direction substantially perpendicular to a plane defined by the middle wire loop.

Concept 27. The extraction device of Concept 26 or any other Concept, further comprising a plurality of interconnecting wires that extend from the first wire loop to the middle wire loop and from the middle wire loop to the third wire loop.

Concept 28. The extraction device of Concept 24 or any other Concept, wherein the first, second, and third wire loops are configured to separate by a rotation of the second and third wire loops relative to the first wire loop.

Concept 29. The extraction device of Concept 28 or any other Concept, further comprising first, second, and third nested wire-guide structures within the delivery shaft and configured to control a rotational position of the first, second, and third wire loops.

Concept 30. The extraction device of Concept 29 or any other Concept, wherein the first wire-guide structure comprises:
a cylindrical main body; and
a plurality of protrusions on an outer surface of the cylindrical main body.

Concept 31. The extraction device of Concept 30 or any other Concept, wherein the second wire-guide structure comprises:
a cylindrical main body at least partially nested within the cylindrical main body of the first wire-guide structure; and
at least one slot for the second wire loop.

Concept 32. The extraction device of Concept 31 or any other Concept, wherein the third wire-guide structure comprises:
a cylindrical main body at least partially nested within the cylindrical main body of the second wire-guide structure; and
at least one slot for the third wire loop.

Concept 33. The extraction device of Concept 32 or any other Concept, wherein the second and third wire-guide structures are rotatable relative to the first wire-guide structure.

Concept 34. The extraction device of Concept 33 or any other Concept, wherein the first, second, and third wire-guide structures are slidable within the delivery shaft for extension and retraction of the first, second, and third wire loops.

Concept 35. An extraction device, comprising:
a delivery shaft having a lumen and a distal end;
first and second wire loops extendible from within the lumen at the distal end; and a plurality of interconnecting wires that extend from the first wire loop to the second wire loop, wherein the first and second wire loops are configured to separate upon extension from within the lumen to at least partially surround a lens of a patient's eye, and wherein the separated first and second wire loops and the plurality of interconnecting wires are configured to be withdrawn into the lumen to pass through and dissect the lens.

Concept 36. The extraction device of Concept 35 or any other Concept, wherein the first and second wire loops are configured to linearly separate to a separated configuration in which the first wire loop is substantially parallel to the second wire loop.

Concept 37. The extraction device of Concept 35 or any other Concept, wherein the first and second wire loops are configured to separate by a rotation of the first or second wire loop.

Concept 38. The extraction device of Concept 37 or any other Concept, wherein the plurality of interconnecting wires comprises two relatively shorter interconnecting wires that extend between the first and second wire loops near a distal end of the loops and two relatively longer interconnecting wires that extend between the first and second wire loops nearer the distal end of the delivery shaft than the two relatively shorter interconnecting wires.

Concept 39. An extraction device, comprising:
a delivery shaft having a lumen and a distal end;
first, second, and third wire loops extendible from within the lumen at the distal end, wherein the first, second, and third wire loops are configured to separate upon extension from within the lumen and are maneuverable to at least partially surround a lens of a patient's eye;
a stent extendible from within the lumen around the extended first, second, and third wire loops; and
an encapsulation bag extendible from within the lumen around the extended stent and the extended first, second, and third wire loops.

Concept 40. The extraction device of Concept 39 or any other Concept, wherein the stent comprises an opening and the encapsulation bag comprises an opening configured to be coaligned with the opening in the stent in an extended configuration for the stent and the encapsulation bag.

Concept 41. The extraction device of Concept 39 or any other Concept, further comprising a spiral compaction wire configured to radially compress the encapsulation bag.

Concept 42. The extraction device of Concept 41 or any other Concept, wherein the first, second, and third wire loops are configured to be retracted into the lumen to pass through and cut the lens into pieces.

Concept 43. The extraction device of Concept 42 or any other Concept, wherein the stent is configured to be retracted into the lumen following retraction of the first, second, and third wire loops to cut the pieces into smaller pieces within the encapsulation bag.

Concept 44. The extraction device of Concept 43 or any other Concept, wherein the spiral compaction wire is configured to radially compress the encapsulation bag following retraction of the first, second, and third wire loops and the stent.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An extraction device, comprising:
a delivery shaft having a lumen and a distal end;
a first wire forming a first arc and being positionable distal to the distal end of the delivery shaft while ends of the first arc are at a distalmost end of the delivery shaft;
a second wire forming a second arc and being positionable distal to the distal end of the delivery shaft while ends of the second arc are at the distalmost end of the delivery shaft, wherein a distalmost extent of the first wire is distal to a distalmost extent of the second wire, wherein the first wire and the second wire are separately retractable relative to the delivery shaft;
a first guide and a second guide each moveable along the first wire toward the distalmost extent of the first wire from a first position to a second position more distal than the first position; and
a cover attached to the first guide and the second guide, wherein, while in the second position, the first wire resides within a first plane and the second wire resides within a second plane that is perpendicular to the first plane, and wherein the cover encompasses an outer cross-sectional dimension of a capture region defined by each of the first wire and the second wire.

2. The extraction device of claim 1, further comprising:
a first ring extending about the first wire and the second wire;
a first cover extending from the first ring to the delivery shaft;
a second ring extending about the first wire and the second wire; and
a second cover extending from the second ring to the distalmost end of the first wire.

3. The extraction device of claim 1, wherein, while in the second position, the cover comprises an aperture disposed at the distalmost end of the first wire.

4. The extraction device of claim 1, wherein, while in the second position, the first wire resides in a first plane and the second wire resides in a second plane, the first plane being perpendicular to the second plane.

5. The extraction device of claim 1, wherein the first wire has a larger diameter than the second wire, the first wire comprising a groove configured to receive the second wire.

6. The extraction device of claim 1, further comprising a third wire connected to the cover.

7. The extraction device of claim 1, wherein one of the first wire and the second wire comprises a shape memory material.

8. The extraction device of claim 1, wherein the first and second guides are configured to move along the first wire to deploy the cover from an undeployed state at the first position to the encompassing state in the second position.

9. The extraction device of claim 1, wherein the lumen of the shaft comprises a flexible material configured to expand when the cover is retracted into the shaft.

* * * * *